United States Patent
Gu et al.

(10) Patent No.: US 7,553,453 B2
(45) Date of Patent: *Jun. 30, 2009

(54) ASSAY IMPLEMENTATION IN A MICROFLUIDIC FORMAT

(75) Inventors: Yuandong Gu, Plymouth, MN (US); Aravind Padmanabhan, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/618,502

(22) Filed: Dec. 29, 2006

(65) Prior Publication Data
US 2007/0190525 A1 Aug. 16, 2007

Related U.S. Application Data

(60) Continuation-in-part of application No. 11/615,884, filed on Dec. 22, 2006, and a continuation-in-part of application No. 10/908,460, filed on May 12, 2005, and a continuation-in-part of application No. 10/908,461, filed on May 12, 2005, and a continuation-in-part of application No. 11/306,508, filed on Dec. 30, 2005, (Continued)

(51) Int. Cl.
*G01N 1/10* (2006.01)
*G01N 21/05* (2006.01)
*G01N 33/48* (2006.01)

(52) U.S. Cl. .............. 422/100; 422/73; 422/82.05; 422/82.08; 436/63; 436/164; 436/165; 436/172; 436/180; 435/7.1; 435/7.24; 435/29; 435/34; 435/287.2; 435/287.3; 435/288.7

(58) Field of Classification Search ............... 436/8, 436/10, 63, 66, 164, 165, 172, 174, 180; 422/61, 68.1, 73, 82.05, 82.08, 100; 435/5, 435/7.1, 7.22, 7.24, 7.25, 7.32, 29, 34, 287.2, 435/287.3, 288.3, 288.4, 288.7
See application file for complete search history.

(56) References Cited

U.S. PATENT DOCUMENTS

| 3,822,095 A | 7/1974 | Hirshfield |
| 3,928,094 A | 12/1975 | Angell |
| 3,976,862 A | 8/1976 | Curbelo |

(Continued)

FOREIGN PATENT DOCUMENTS

| DE | 10122321 | 4/2002 |
| EP | 0269076 | 6/1988 |

(Continued)

OTHER PUBLICATIONS

HemoCue Hb 201+, Operating Manual, pp. 1-41, prior to Dec. 2006.
Lamvik et al., Nonlabeled Secondary Antibodies Augment/Maintain the Binding of Primary, Specific Antibodies to Cell Membrande Antigens, Cytometery 45, pp. 187-193, 2001.

(Continued)

*Primary Examiner*—Maureen M Wallenhorst
(74) *Attorney, Agent, or Firm*—Kris T. Fredrick

(57) ABSTRACT

An assay implementation in a microfluidic format in a cartridge relating to a point-of-care instrument platform for monitoring and diagnosing infectious diseases (e.g., AIDS and malaria). The platform may also provide a complete blood count. The instrument platform may hold the cartridge and a portion of an optical system for fluorescent and scattered light related analyses of blood sample in a flow channel of the cartridge.

34 Claims, 33 Drawing Sheets

Related U.S. Application Data which is a continuation-in-part of application No. 10/950,898, filed on Sep. 27, 2004, and a continuation-in-part of application No. 10/938,265, filed on Sep. 9, 2004, which is a continuation-in-part of application No. 10/304,773, filed on Nov. 26, 2002, which is a continuation-in-part of application No. 11/306,508, which is a continuation-in-part of application No. 10/908,460, application No. 11/618,502, which is a continuation-in-part of application No. 11/306,508, which is a continuation-in-part of application No. 10/908,014, filed on Apr. 25, 2005, which is a continuation-in-part of application No. 10/304,773, filed on Nov. 26, 2002, which is a continuation-in-part of application No. 09/630,924, filed on Aug. 2, 2000, now Pat. No. 6,597,438, application No. 11/618,502, which is a continuation-in-part of application No. 11/306,508, which is a continuation-in-part of application No. 10/908,014, which is a continuation-in-part of application No. 10/980,685, filed on Nov. 3, 2004, now Pat. No. 6,968,862, which is a division of application No. 10/174,851, filed on Jun. 19, 2002, now Pat. No. 6,837,476, application No. 11/618,502, which is a continuation-in-part of application No. 11/306,508, which is a continuation-in-part of application No. 10/908,014, which is a continuation-in-part of application No. 10/340,231, filed on Jan. 10, 2003, now Pat. No. 6,889,567, which is a division of application No. 09/586,093, filed on Jun. 2, 2000, now Pat. No. 6,568,286, application No. 11/618,502, which is a continuation-in-part of application No. 11/306,508, which is a continuation-in-part of application No. 10/950,898, filed on Sep. 27, 2004, now Pat. No. 7,130,046, application No. 11/618,502, which is a continuation-in-part of application No. 11/306,508, which is a continuation-in-part of application No. 10/938,265, filed on Sep. 9, 2004, which is a continuation-in-part of application No. 10/304,773, which is a continuation-in-part of application No. 09/630,924, filed on Aug. 2, 2000, now Pat. No. 6,597,438, application No. 11/618,502, which is a continuation-in-part of application No. 11/306,508, which is a continuation-in-part of application No. 10/938,265, which is a continuation-in-part of application No. 10/225,325, filed on Aug. 21, 2002, now Pat. No. 6,970,245, application No. 11/618,502, which is a continuation-in-part of application No. 11/306,508, which is a continuation-in-part of application No. 10/932,662, filed on Sep. 2, 2004, application No. 11/618,502, which is a continuation-in-part of application No. 11/306,508, which is a continuation-in-part of application No. 10/899,607, filed on Jul. 27, 2004, now Pat. No. 7,242,474, application No. 11/618,502, which is a continuation-in-part of application No. 11/306,508, which is a continuation-in-part of application No. 10/938,245, filed on Sep. 9, 2004, now Pat. No. 7,016,022, which is a continuation of application No. 10/824,859, filed on Apr. 14, 2004, now Pat. No. 7,215,425, which is a continuation-in-part of application No. 10/225,325, and a continuation-in-part of application No. 09/630,927, filed on Aug. 2, 2002, now Pat. No. 6,549,275, application No. 11/618,502, which is a continuation-in-part of application No. 11/306,508, which is a continuation-in-part of application No. 10/759,875, filed on Jan. 16, 2004, now Pat. No. 7,262,838, which is a continuation-in-part of application No. 09/896,230, filed on Jun. 29, 2001, now Pat. No. 6,700,130, application No. 11/618,502, which is a continuation-in-part of application No. 11/306,508, which is a continuation-in-part of application No. 10/759,875, which is a continuation-in-part of application No. 10/304,773, application No. 11/618,502, which is a continuation-in-part of application No. 11/306,508, which is a continuation-in-part of application No. 10/304,773, which is a continuation-in-part of application No. 09/630,924, application No. 11/618,502, which is a continuation-in-part of application No. 11/306,508, which is a continuation-in-part of application No. 10/908,014, which is a continuation-in-part of application No. 10/953,197, filed on Sep. 28, 2004, now Pat. No. 7,283,223, application No. 11/618,502, which is a continuation-in-part of application No. 11/306,508, which is a continuation-in-part of application No. 11/027,134, filed on Dec. 30, 2004, which is a continuation-in-part of application No. 10/304,773, which is a continuation-in-part of application No. 09/630,924, application No. 11/618,502, which is a continuation-in-part of application No. 11/306,508, said application No. 11/306,508 is a continuation-in-part of application No. 11/306,402, filed on Dec. 27, 2002.

(60) Provisional application No. 60/571,235, filed on May 14, 2004, provisional application No. 60/755,014, filed on Dec. 29, 2005, provisional application No. 60/753,293, filed on Dec. 22, 2005.

(56) References Cited

U.S. PATENT DOCUMENTS

| | | |
|---|---|---|
| 4,284,412 A | 8/1981 | Hansen et al. |
| 4,478,076 A | 10/1984 | Bohrer |
| 4,478,077 A | 10/1984 | Bohrer |
| 4,501,144 A | 2/1985 | Higashi et al. |
| 4,599,000 A | 7/1986 | Yamada |
| 4,651,564 A | 3/1987 | Johnson et al. |
| 4,683,159 A | 7/1987 | Bohrer et al. |
| 4,695,034 A | 9/1987 | Shimizu et al. |
| 4,704,033 A | 11/1987 | Fay et al. |
| 4,745,279 A | 5/1988 | Karkar et al. |
| 4,818,263 A | 4/1989 | Mitch |
| 4,874,949 A | 10/1989 | Harris et al. |
| 4,911,616 A | 3/1990 | Laumann, Jr. |
| 4,932,989 A | 6/1990 | Presby |
| 4,980,292 A | 12/1990 | Elbert et al. |
| 5,017,497 A | 5/1991 | de Grooth et al. |
| 5,050,429 A | 9/1991 | Nishimoto et al. |
| 5,078,581 A | 1/1992 | Blum et al. |
| 5,082,242 A | 1/1992 | Bonne et al. |
| 5,085,562 A | 2/1992 | van Lintel |
| 5,096,388 A | 3/1992 | Weinberg |
| 5,108,623 A | 4/1992 | Cangelosi et al. |
| 5,129,794 A | 7/1992 | Beatty |
| 5,171,132 A | 12/1992 | Miyazaki et al. |
| 5,176,358 A | 1/1993 | Bonne et al. |
| 5,185,641 A | 2/1993 | Igushi et al. |
| 5,194,909 A | 3/1993 | Tycko |
| 5,219,278 A | 6/1993 | van Lintel |
| 5,224,843 A | 7/1993 | van Lintel |
| 5,244,537 A | 9/1993 | Ohnstein |
| 5,323,999 A | 6/1994 | Bonne et al. |
| 5,441,597 A | 8/1995 | Bonne et al. |
| 5,452,878 A | 9/1995 | Gravesen et al. |
| 5,457,526 A | 10/1995 | Kosaka |
| 5,504,011 A * | 4/1996 | Gavin et al. .......... 436/69 |
| 5,510,267 A | 4/1996 | Marshall |

| | | |
|---|---|---|
| 5,528,045 A | 6/1996 | Hoffman et al. |
| 5,570,193 A | 10/1996 | Landa et al. |
| 5,601,080 A | 2/1997 | Oppenheimer |
| 5,616,501 A | 4/1997 | Rodriguez et al. |
| 5,633,724 A | 5/1997 | King et al. |
| 5,683,159 A | 11/1997 | Johnson |
| 5,716,852 A | 2/1998 | Yager et al. |
| 5,717,631 A | 2/1998 | Carley et al. |
| 5,726,751 A | 3/1998 | Altendorf et al. |
| 5,757,476 A | 5/1998 | Nakamoto et al. |
| 5,760,900 A | 6/1998 | Ito et al. |
| 5,793,485 A | 8/1998 | Gourley |
| 5,799,030 A | 8/1998 | Brenner |
| 5,822,170 A | 10/1998 | Cabuz et al. |
| 5,836,750 A | 11/1998 | Cabuz |
| 5,837,547 A | 11/1998 | Schwartz |
| 5,839,807 A | 11/1998 | Perlo |
| 5,863,502 A | 1/1999 | Southgate et al. |
| 5,880,474 A | 3/1999 | Norton et al. |
| 5,893,722 A | 4/1999 | Hibbs-Brennen et al. |
| 5,901,939 A | 5/1999 | Cabuz et al. |
| 5,922,210 A | 7/1999 | Brody et al. |
| 5,932,100 A | 8/1999 | Yager et al. |
| 5,948,684 A | 9/1999 | Weigl et al. |
| 5,970,315 A | 10/1999 | Carley et al. |
| 5,971,158 A | 10/1999 | Yager et al. |
| 5,972,710 A | 10/1999 | Weigl et al. |
| 5,974,867 A | 11/1999 | Forster et al. |
| 6,007,775 A | 12/1999 | Yager |
| 6,032,689 A | 3/2000 | Tsai et al. |
| 6,054,335 A | 4/2000 | Sun et al. |
| 6,082,185 A | 7/2000 | Saaski |
| 6,091,197 A | 7/2000 | Sun et al. |
| 6,091,537 A | 7/2000 | Sun et al. |
| 6,094,293 A | 7/2000 | Yokoyama et al. |
| 6,097,485 A * | 8/2000 | Lievan .................. 356/338 |
| 6,097,859 A | 8/2000 | Solgaard et al. |
| 6,106,245 A | 8/2000 | Cabuz |
| 6,109,889 A | 8/2000 | Zengerie et al. |
| 6,116,756 A | 9/2000 | Peeters et al. |
| 6,124,663 A | 9/2000 | Haake et al. |
| 6,139,800 A | 10/2000 | Chandler |
| 6,179,586 B1 | 1/2001 | Herb et al. |
| 6,184,607 B1 | 2/2001 | Cabuz et al. |
| 6,215,221 B1 | 4/2001 | Cabuz et al. |
| 6,228,652 B1 * | 5/2001 | Rodriguez et al. ............ 436/63 |
| 6,237,619 B1 | 5/2001 | Maillefer et al. |
| 6,240,944 B1 | 6/2001 | Ohnstein et al. |
| 6,249,341 B1 | 6/2001 | Basiji et al. |
| 6,265,176 B1 * | 7/2001 | Lin et al. .................. 435/7.92 |
| 6,281,975 B1 | 8/2001 | Munk |
| 6,382,228 B1 | 5/2002 | Cabuz et al. |
| 6,549,275 B1 | 4/2003 | Cabuz et al. |
| 6,597,438 B1 | 7/2003 | Cabuz et al. |
| 6,949,377 B2 * | 9/2005 | Ho .......................... 435/287.1 |
| 2003/0057968 A1 | 3/2003 | Wang et al. |
| 2003/0142291 A1 * | 7/2003 | Padmanabhan et al. ....... 356/39 |
| 2004/0065143 A1 | 4/2004 | Husher |
| 2004/0109386 A1 | 6/2004 | Gold et al. |
| 2004/0154933 A1 | 8/2004 | Cosofret |
| 2004/0233424 A1 | 11/2004 | Lee et al. |
| 2005/0105077 A1 | 5/2005 | Padmanabhan et al. |
| 2006/0134599 A1 * | 6/2006 | Toner et al. .................. 435/4 |

FOREIGN PATENT DOCUMENTS

| | | |
|---|---|---|
| EP | 0694784 | 1/1996 |
| EP | 1001326 | 5/1999 |
| EP | 1134548 | 9/2001 |
| EP | 1359419 | 5/2003 |
| JP | 60082865 | 12/1983 |
| JP | 61066947 | 4/1986 |
| JP | 10073528 | 3/1998 |
| JP | 2000056228 | 2/2000 |
| JP | 2004257756 | 9/2004 |
| WO | 9527199 | 10/1995 |
| WO | 9960397 | 11/1999 |
| WO | 0109598 | 2/2001 |
| WO | 0210713 | 2/2002 |
| WO | 0210714 | 2/2002 |
| WO | 2004059316 | 7/2004 |
| WO | 2005090983 | 9/2005 |
| WO | 2005108963 | 11/2005 |
| WO | 2005114142 | 12/2005 |
| WO | 2005114144 | 12/2005 |

OTHER PUBLICATIONS http://www.micronics.net/tsensor.htm, pp. 1-4, downloaded Jun. 14, 2000.
http://www.micronics.net/hfilter.htm, pp. 1-3, downloaded Jun. 14, 2000.
http://www.micronics.net/mcytometry.htm, pp. 1-4, downloaded Jun. 14, 2000.
http://www.micronics.net/orcafluidics.htm, pp. 1-4, downloaded Jun. 14, 2000.
Altendorf et al, "Results Obtained Using A Prototype Microfluidics-Based Hematology Analyzer", SPIE Biomedical Optics 97, 1997.
Altendorf et al., "Differential Blood Cell Counts Obtained Using A Microchannel Based Flow Cytometer", Solid State Sensors & Actuators, vol. 1, 531, 1997.
Altendorf et al., "Implementation Of Novel Optical Detection Methods For Clinically Important Blood Analytes Using Microfabricated Flow Structures (T-Sensors™)", MicroTAS 98, Banff, Canada, Apr. 1998.
Altendorf et al., "Microfabrication Technology For Research And Diagnostics, Silicon Microchannel Optical Flow Cytometry", SPIE Proceedings, Biomedical Optics 96, Jan. 1996.
Cabuz et al., "Mesoscopic Sampler Based on 3D Array of Electrostatically Activated Diaphragms", The 10th Int. Conf. On Solid-State Sensors and Actuators, Transducers'99, Jun. 7-12, 1999, Sendai Japan, p. 1890-1.
Darling et al., "Integration Of Microelectrodes With Etched Microchannels For In-Stream Electrochemical Analysis", MicroTAS 98, Banff, Canada, Apr. 1998.
Fedder et al., "Laminated High-Aspect-Ratio Microstructures in a Conventional CMOS Process", Proc. Micro Electro Mechanical Systems Workshop, MEMS 96, San Diego, California, Feb. 11-15, 1996, pp. 13-18.
Hatch et al., "Microfluidic Approaches To Immunoassays", SPIE conference on Micromachining and Microfabrication Symposium at Santa Clara, CA, Sep. 20-22, 1999.
Huang et al., "Development Of A Flow Cytometry Based Miniature Chemical Fluid Analysis System Using Fluorescent Microbeads", SPIE Biomedical Optics, BIOS 97, conference proceedings, 1997.
Lehman et al., "High-Frequency Modulation Characteristics of Red VCSELs", Electronics Letters, Feb. 13, 1997, vol. 33(4), pp. 298-300. Copyright 1997 IEEE.
Ohnstein et al., "Micromachined Silicon Microvalve", Proceedings of MEMS, 1990, IEEE Micro Electromechanical Systems, Napa Valley, California, Feb. 11-14, 1990, pp. 95-98.
Roulet et al., "Fabrication of Multilayer Systems Combining Microfluidic and Microoptical Elements for Fluorescence Detection," Journal of Microelectromechanical Systems, vol. 10 No. 44, pp. 483-491, Dec. 4, 2001.

Shapiro, "Practical Flow Cytometry", third edition, 1995, p. 237.

Strzelecka et al., "Parallel Free-Space Optical Interconnect Based on Arrays of Vertical-Cavity Lasers and Detectors with Monolithic Microlenses", Applied Optics, v. 37(14), May 10, 1998, pp. 2811-2821. Copyright 1998 Optical Society of America.

Terstappen et al., "Four-Parameter White Blood Cell Differential Counting Based on Light Scattering Measurements", Alan R. Liss, Inc., Cytometry 9:39-43, 1988.

Toshiyoshi et al., "Micromechanical Lens Scanner for Fiber Optic Switches", Proc. 3rd International Conference on Micro Opto Electro Mechanical Systems (MOEMS 99), Aug. 30-Sep. 1, 1999, Mainz, Germany, pp. 165-170.

Toshiyoshi et al., "Surface micromachined 2D Lens Scanner Array", Proc. IEEE?LEOS International Coference on Optical EMMS/Sheraton Kauai Resort, Kauai, Hawaii, Aug. 21-24, 2000, 3 pages.

Tuantranont et al., "Flip Chip Integration of Lenslet Arrays on Segmented Deformable Micromirrors", Part of the Symposium on Design, Test and Microfabrication of MEMS and MOEMS, Paris, France, Mar.-Apr. 1999, SPIE vol. 3680, 0277-786X/99, pp. 668-678.

Tuantranont et al., "MEMS-Controllable Microlens Array For Beam Steering and precision Alignment in Optical Interconnect Systems", Solid-State Sensor and Actuator Workshop, Hilton Head Island, South Carolina, Jun. 4-8, 2000, pp. 101-104.

Weigl et al, "Silicon-Microfabricated Diffusion-Based Optical Chemical Sensor", Reprint from "Sensors & Actuators" B 38-39, 452-457, 1997I.

Weigl et al, "Microfluidic Diffusion-Based Separation And Detection", Science, vol. 283, pp. 346-347, Jan. 15, 1999.

Weigl et al, "Optical And Electrochemical Diffusion-Based Detection Of Analytes In Complex Samples Using Microfabricated Flow Structures (T-SensorSTM)", Micro- and nanofabn'cated electro-optical mechanical systems for biomedical and environmental applications II- SPIE vol. 3606, Jan. 25-26, 1999.

Weigl et al, "Simultaneous Self-Referencing Analyte Determination In Complex Sample Solutions Using Microfabricated Flow Structures (T-Sensors™)", Proceedings of MicroTAS 98, 81-4, Banff, Canada, 1998.

Weigl et al., "Diffusion-Based Optical Chemical Detection In Silicon Flow Structures", B. Weigl et al., Analytical Methods & Instrumentation, µTTAS 96 special edition, 1996.

Weigl et al., "Fluorescence And Absorbance Analyte Sensing In Whole Blood And Plasma Based On Diffusion Separation In Silicon-Microfabricated Flow Structures (T-Sensors™)", Biomedical Optics, vol. 6, No. 1, Jul. 1997.

Weigl et al., "Rapid Sequential Chemical Analysis Using Multiple Fluorescent Reporter Beads", µTTAS 96 Conference Proceedings, 1996.

Weigl, "Microfluidic Diffusion Based Electrochemical Detection Using Microfabricated Flow Structures (T-Sensors™)", Analytical Chemistry, submitted 1999.

Weigl, "Whole Blood Assays Using Microfluidics-Based T-SensorSTM Technology", Medical Design Online, http://news.medicaldesignonline.com/featuresarticles/19990416-5922.html, Apr. 1999.

Yager et al., "Applying Microfluidic Chemical Analytical Systems To Imperfect Samples", Micro Total Analysis Systems 98, D. Harrison & A. van den Berg (ed.), Kluwer Academic Publishers, Dordrecht, 207-212, 1998.

Yager et al., "Design Of Microfluidic Sample Preconditioning Systems For Detection Of Biological Agents In Environmental Samples", Yager, M. et al., SPIE Proceedings, 3515, 252-259, 1998.

\* cited by examiner

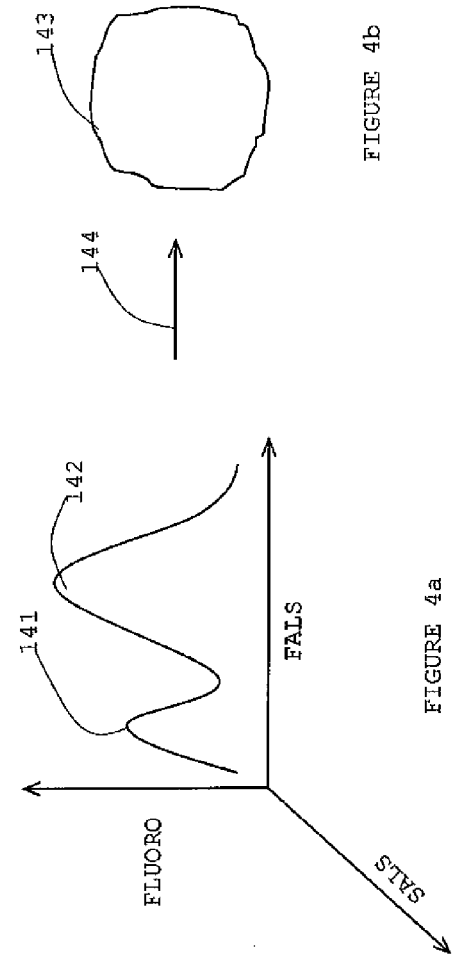
FIGURE 4b
FIGURE 4a
FIGURE 2
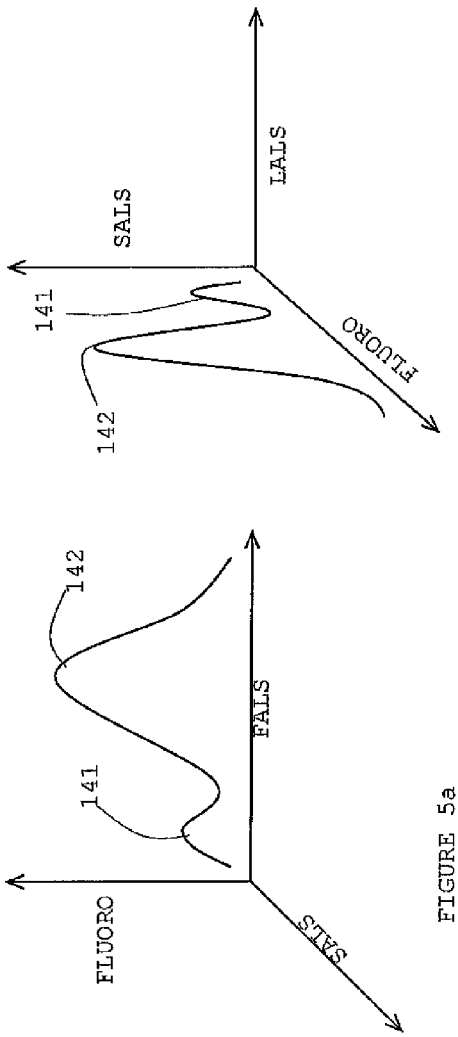
FIGURE 5b
FIGURE 5a
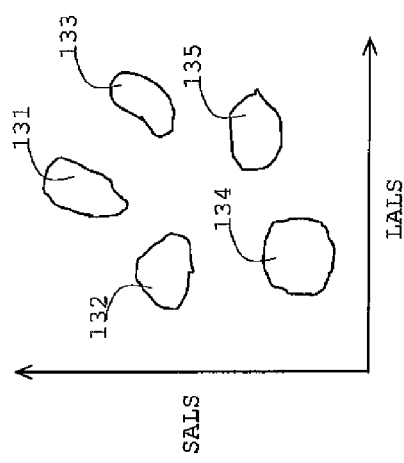
FIGURE 3

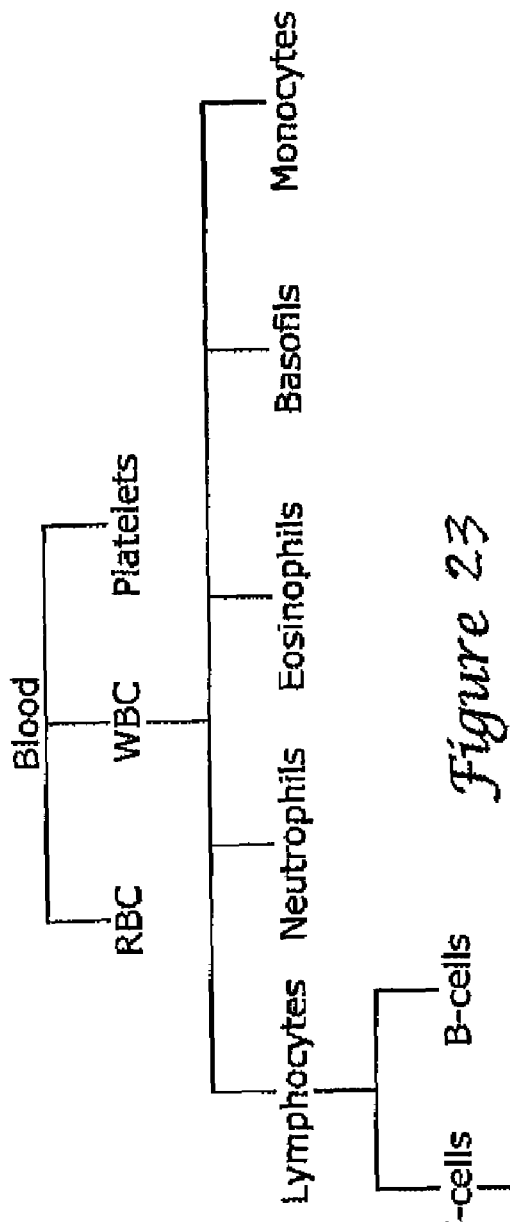
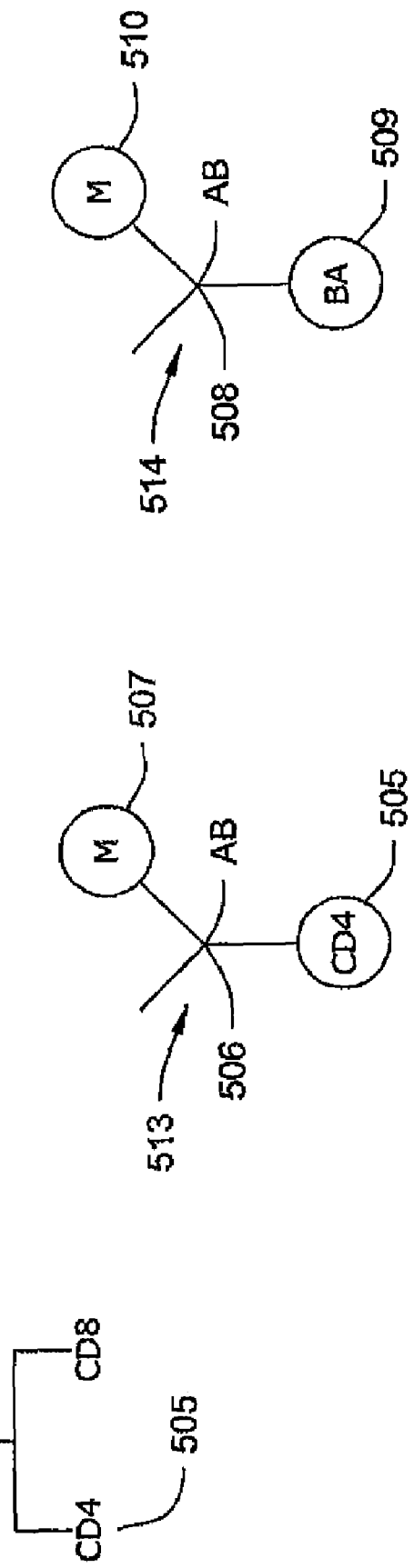
Figure 23
Figure 24a
Figure 24b

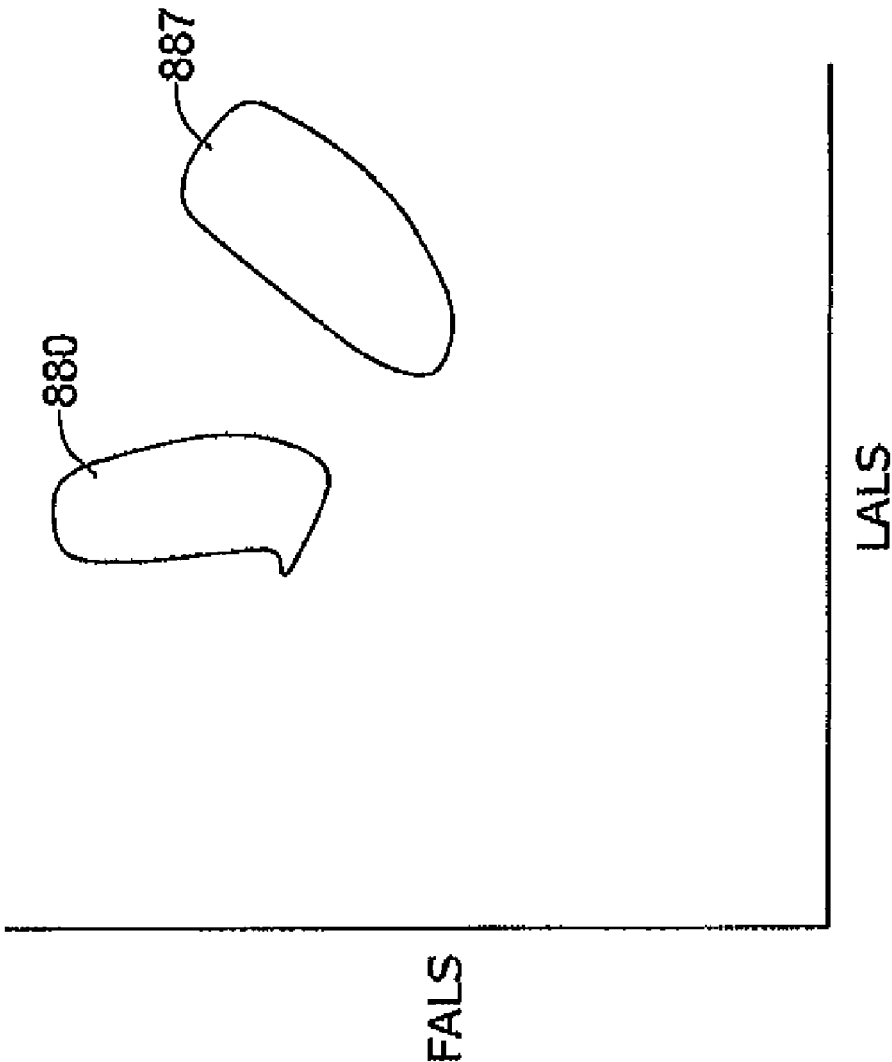

| Parameter | AIDS Assay | Malaria Assay |
|---|---|---|
| AIDS markers/malaria species | CD4, CD45 | P. falciparum, P. vivax |
| No. of fluorescent optical channels | 2 | 2 |
| No. of scattering channels | 1 (90°) | 1 (90°) |
| Optional scattering channels (for total WBC count and three-part differential) | 2 (1°–3°, 4°–13°) | 2 (1°–3°, 4°–13°) |
| Reagent reservoirs on-card | 4 | 4 |
| Flow sensors on-card | 4 | 4 |
| No. of cytometer measurement channels on the cartridge (without three-part differential capability) | 1 | 1 |
| No. of cytometer measurement channels on the cartridge (with three-part differential capability) | 2 | 2 |

FIGURE 32

| Assay Step | Assay Used on Benchtop Cytometer | Microfluidics-Based Assay on Cartridge |
|---|---|---|
| Whole-blood sample input | 100 μL | 12 μL |
| Number of dilution steps | 4 | None |
| Monoclonal antibodies | 5 μL | 0.6 μL (not optimized) |
| Number/duration of incubation steps | 2 (30 minutes at 40°C and 5 minutes at room temperature) | 2 (20 seconds at room temp; 20 seconds at room temperature) |
| Lysing solution | 1.4 mL | 500 μL (not optimized) |
| Cytometric measurement time | 2-3 minutes | 2-3 minutes |

FIGURE 36

ASSAY IMPLEMENTATION IN A MICROFLUIDIC FORMAT

This application claims the benefit of U.S. Provisional Patent Application 60/755,014 filed Dec. 29, 2005.

This application is a continuation-in-part of U.S. patent application Ser. No. 11/615,884, filed Dec. 22, 2006, which claims the benefit of U.S. Provisional Patent Application 60/753,293 filed Dec. 22, 2005.

This application is a continuation-in-part application of U.S. patent application Ser. No. 10/908,460, filed May 12, 2005, which claims the benefit of Provisional Application No. 60/571,235, filed May 14, 2004.

This application is a continuation-in-part application of U.S. patent application Ser. No. 10/908,461, filed May 12, 2005, which claims the benefit of Provisional Application No. 60/571,235, filed May 14, 2004.

This application is a continuation-in-part of U.S. patent application Ser. No. 11/306,508, filed Dec. 30, 2005, which is a continuation-in-part of U.S. patent application Ser. No. 10/950,898, filed Sep. 27, 2004.

This application is a continuation-in-part of U.S. patent application Ser. No. 10/938,265, filed Sep. 9, 2004, which is a continuation-in-part of U.S. patent application Ser. No. 10/304,773, filed on Nov. 26, 2002.

This patent application is a continuation-in-part of U.S. patent application Ser. No. 11/306,508, filed Dec. 30, 2005, which is a continuation-in-part of U.S. patent application Ser. No. 10/908,460, filed May 12, 2005, which claims the benefit of Provisional Patent Application No. 60/571,235, filed May 14, 2004.

Also, this patent application is a continuation-in-part of U.S. patent application Ser. No. 11/306,508, filed Dec. 30, 2005, which is a continuation-in-part of U.S. patent application Ser. No. 10/908,014, filed Apr. 25, 2005, which is a continuation-in-part of U.S. patent application Ser. No. 10/304,773, filed Nov. 26, 2002, which is a continuation-in-part of U.S. patent application Ser. No. 09/630,924, filed Aug. 2, 2000, now U.S. Pat. No. 6,597,438.

Also, this patent application is a continuation-in-part of U.S. patent application Ser. No. 11/306,508, filed Dec. 30, 2005, which is a continuation-in-part of U.S. patent application Ser. No. 10/908,014, filed Apr. 25, 2005, which is a continuation-in-part of U.S. patent application Ser. No. 10/980,685, filed Nov. 3, 2004, (issued as U.S. Pat. No. 6,968,862) which is a division of U.S. patent application Ser. No. 10/174,851, filed Jun. 19, 2002, now U.S. Pat. No. 6,837,476.

Also, this patent application is a continuation-in-part of U.S. patent application Ser. No. 11/306,508, filed Dec. 30, 2005, which is a continuation-in-part of U.S. patent application Ser. No. 10/908,014, filed Apr. 25, 2005, which is a continuation-in-part of U.S. patent application Ser. No. 10/340,231, filed Jan. 10, 2003, now U.S. Pat. No. 6,889,567, which is a division of U.S. patent application Ser. No. 09/586,093, filed Jun. 2, 2000, now U.S. Pat. No. 6,568,286.

Also, this patent application is a continuation-in-part of U.S. patent application Ser. No. 11/306,508, filed Dec. 30, 2005, which is a continuation-in-part of U.S. patent application Ser. No. 10/950,898, filed Sep. 27, 2004, (issued as U.S. Pat. No. 7,130,046).

Also, this patent application is a continuation-in-part of U.S. patent application Ser. No. 11/306,508, filed Dec. 30, 2005, which is a continuation-in-part of U.S. patent application Ser. No. 10/938,265, filed on Sep. 9, 2004, which is a continuation-in-part of U.S. patent application Ser. No. 10/304,773, filed Nov. 26, 2002, which is a continuation-in-part of U.S. application Ser. No. 09/630,924, filed Aug. 2, 2000 (issued as U.S. Pat. No. 6,597,438).

Also, this patent application is a continuation-in-part of U.S. patent application Ser. No. 11/306,508, filed Dec. 30, 2005, which is a continuation-in-part of U.S patent application Ser. No. 10/938,265, filed on Sep. 9, 2004, which is a continuation-in-part of U.S. patent application Ser. No. 10/225,325, filed Aug. 21, 2002, now U.S. Pat. No. 6,970,245.

Also, this patent application is a continuation-in-part of U.S. patent application Ser. No. 11/306,508, filed Dec. 30, 2005, which is a continuation-in-part of U.S. patent application Ser. No. 10/932,662, filed Sep. 2, 2004.

Also, this patent application is a continuation-in-part of U.S. patent application Ser. No. 11/306,508, filed Dec. 30, 2005, which is a continuation-in-part of U.S. patent application Ser. No. 10/899,607, filed Jul. 27, 2004 (issued as U.S. Pat. No. 7,242,474).

Also, this patent application is a continuation-in-part of U.S. patent application Ser. No. 11/306,508, filed Dec. 30, 2005, which is a continuation-in-part of U.S. patent application Ser. No. 10/938,245, filed on Sep. 9, 2004 (issued as U.S. Pat. No. 7,016,022), which is continuation of U.S. patent application Ser. No. 10/824,859, filed Apr. 14, 2004 (issued as U.S. Pat. No. 7,215,425), which is a continuation-in-part of U.S. patent application Ser. No. 10/225,325, filed Aug. 21, 2002, now U.S. Pat. No. 6,970,245, which is a continuation-in-part of U.S. patent application Ser. No. 09/630,927, filed Aug. 2, 2000, now U.S. Pat. No. 6,549,275.

Also, this patent application is a continuation-in-part of U.S. patent application Ser. No. 11/306,508, filed Dec. 30, 2005, which is a continuation-in-part of U.S. patent application Ser. No. 10/759,875, filed Jan. 16, 2004 (issued as U.S. Pat. No. 7,262,838), which is a continuation-in-part of U.S. patent application Ser. No. 09/896,230, filed Jun. 29, 2001, now U.S. Pat. No. 6,700,130.

Also, this patent application is a continuation-in-part of U.S. patent application Ser. No. 11/306,508, filed Dec. 30, 2005, which is a continuation-in-part of U.S. patent application Ser. No. 10/759,875, filed Jan. 16, 2004, now U.S. Pat. No. 7,262,838 which is a continuation-in-part of U.S. patent application Ser. No. 10/304,773, filed Nov. 26, 2002.

Also, this patent application is a continuation-in-part of U.S. patent application Ser. No. 11/306,508, filed Dec. 30, 2005, which is a continuation-in-part of U.S. patent application Ser. No. 10/304,773, filed Nov. 26, 2002, which is a continuation-in-part of U.S. patent application Ser. No. 09/630,924, filed Aug. 2, 2000, now U.S. Pat. No. 6,597,438.

Also, this patent application is a continuation-in-part of U.S. patent application Ser. No. 11/306,508, filed Dec. 30, 2005, which is a continuation-in-part of U.S. patent application Ser. No. 10/908,014, filed Apr. 25, 2005, which is a continuation-in-part of U.S. patent application Ser. No. 10/953,197, filed Sep. 28, 2004 (issued as U.S. Pat. No. 7,283,223).

Also, this patent application is a continuation-in-part of U.S. patent application Ser. No. 11/306,508, filed Dec. 30, 2005, which is a continuation-in-part of U.S. patent application Ser. No. 11/027,134, filed Dec. 30, 2004, which is a continuation-in-part U.S. patent application Ser. No. 10/304,773, filed Nov. 26, 2002, which is a continuation-in-part of U.S. patent application Ser. No. 09/630,924, filed Aug. 2, 2000, now U.S. Pat. No. 6,597,438.

Also, this patent application is a continuation-in-part of U.S. patent application Ser. No. 11/306,508, filed Dec. 30, 2005, which is a continuation-in-part of U.S. patent application Ser. No. 11/306,402, filed Dec. 27, 2005.

BACKGROUND

The invention pertains to cytometry and particularly to portable cytometry. More particularly, the invention pertains to blood analysis.

HIV and malaria are two of the leading causes of mortality and morbidity, each of which is preventable with prompt diagnosis and effective treatment. The overwhelming global burden of both of these diseases occurs in Sub-Saharan Africa. There is evidence to suggest that the prevalence of malaria parasitaemia increases with HIV infection, the incidence of malaria increases with HIV infection, HIV increases the risk that a malaria patient will develop severe malaria, and malaria prophylaxis or treatment may be less effective with HIV co-infection. For HIV monitoring, a marker of interest is CD4+ lymphocytes. CD4 depletion appears to be directly linked with the pathogenesis of HIV disease.

One may note that any variation in the total white blood cell count or lymphocyte count could affect a person's CD4 count. This is a reason why some people may prefer to talk about the CD4 percentage which is less variable.

When ordering a complete blood count (CBC), one may get a hematocrit and hemoglobin (which tell provide information about red blood cells) and a white blood cell count. A "differential" may indicate the different types of white blood cells and what percentage are neutrophils, lymphocytes, monocytes, eosinophils, basophils, and so forth. With HIV, the interest is in the lymphocytes.

The T-cell count (CD3 count) may include the CD4 count and the CD8 count. The CD4/CD8 ratio might not used often anymore. Higher numbers appear best for these measures, but one may avoid some confusion by paying attention to the viral load, the absolute count CD4 count, and the CD4 percentage and ignore the CD4/CD8 ratio.

CD4+ (also called T-helper) lymphocytes may be responsible for the immunological defense of the body. Their loss due to HIV infection may result in a progressive deterioration of the immune system and progression to symptoms associated with acquired immune deficiency syndrome (AIDS). Treatment guidelines may call for the use of quantitative CD4+ lymphocyte and HIV viral load tests to determine when anti-retroviral drug treatment should be started, to assess how well a treatment regimen is working, and to assist in determining whether a switch to an alternative drug regimen is needed.

There are ever increasing numbers of HIV-positive individuals in developing countries who will continue to overburden and overwhelm health care services. Existing facilities to monitor CD4+ lymphocyte counts in HIV-positive individuals are either limited or absent in most developing countries because the existing test methods are too expensive and complex. The availability of a simple, inexpensive, semi-quantitative approach for monitoring CD4+ lymphocytes could result in the following disease and public health impact. A simplified, low cost easy-to-use device for testing and monitoring CD4+ lymphocyte levels may enable CD4 testing to be used more commonly and consistently, increasing the effectiveness of HIV therapies and decreasing drug resistance, could be very valuable in the developing world.

Early and accurate diagnosis of infection due to malaria is important for effective disease management and to prevent progression and development of complications such as cerebral malaria. The two most virulent and common species of malaria are *plasmodium* (P) *falciparum* and *plasmodium vivax*, and hence the identification of these two species via a low-cost, easy-to-use device could be very valuable in the developing world.

U.S. Provisional Patent Application 60/753,293 filed Dec. 22, 2005, is hereby incorporated by reference. U.S. Provisional Patent Application 60/755,014 filed Dec. 29, 2005, is hereby incorporated by reference. U.S. patent application Ser. No. 10/908,460, filed May 12, 2005, is hereby incorporated by reference. U.S. patent application Ser. No. 10/908,461, filed May 12, 2005, is hereby incorporated by reference. U.S. patent application Ser. No. 11/306,508, filed Dec. 30, 2005, is hereby incorporated by reference. A continuation-in-part of U.S. patent application Ser. No. 10/950,898, filed Sep. 27, 2004, is hereby incorporated by reference. U.S. patent application Ser. No. 10/938,265, filed Sep. 9, 2004, is hereby incorporated by reference.

SUMMARY

The invention is an apparatus that may provide immunoassay and hematology tests on one point-of-care (POC) microfluidic instrument platform.

BRIEF DESCRIPTION OF THE DRAWING

FIG. 2 is a five-part differentiation graph of white blood cells;

FIG. 3 is a diagram of a white blood cell having an antigen;

FIG. 4a is diagram of a plot of cells in a three-dimensional perspective;

FIG. 4b is a representation of what is seen when a viewer is looking into the edge of the platform the right side;

FIG. 5a is a diagram of a plot of the cells like that of FIG. 4a except that left peak is weak relative to the right peak;

FIG. 5b is a diagram like the plot of FIG. 5a except the diagram has axes re-oriented;

FIG. 23 is a diagram of components of blood;

FIGS. 24a and 24b show antibodies with markers attached to cells for fluorescent identification of the cells;

FIG. 29b is a plot of FALS versus LALS data revealing a differentiation of another two kinds of white blood cells in addition to those of FIG. 29a;

FIG. 32 is a table showing components for various parameters for an AIDS and malaria assays;

FIG. 36 is a table showing a comparison of the miniaturized cytometer and a benchtop cytometer;

DESCRIPTION

The demand for point of care (POC) instruments for diagnostics, monitoring and life sciences applications is growing. One important application for a POC flow cytometer is monitoring AIDS (HIV infected) patients who are under medication (ART) and other patients, including those with other diseases. The flow cytometer provides an implementation of these assays in a microfluidic format.

This invention provides an approach towards implementing a CD4/CD8/CDXX assay (used for monitoring HIV infected patients) for a point-of-care instrument. The assay may be implemented in a microfluidic format of a disposable plastic analysis card. The card will not only be able to perform the CDXX assay but also be able to perform a total/differential white blood cell count. The invention may provide two tests (CDXX test or an immunoassay test and a hematology test) being of respective modules that can be combined on a single microfluidic cartridge. The cartridge may have a laminated structure or have a molded structure, at least in part. The materials of the cartridge may include vary types of plastic and glass materials. Other materials may be used in the structure as appropriate, for example, such as conductive materials for certain electrical components, such as imbedded electrodes.

Some advantages of microfluidic format include minimal reagent consumption (and hence lower test cost), ease of use because both tests are performed on same card, and simplified sample preparation procedures (no 30 minute incubation and the like). The invention may include the implementation of the different assay functions in a microfluidic format on a microfluidic cartridge. These functions may include mixing, separation, filtering, wash-out, preconcentration, lysing, sorting, and so forth.

The present invention may be a POC integrated scattering and fluorescence flow cytometer capable of counting and classifying white blood cells from a whole-blood sample input. The present POC instrument may be used for CD4 monitoring (CD4 absolute count and percent CD4). This cytometer may be composed of a handheld instrument and credit-card-sized disposable analysis cartridges. The disposable cartridges may contain on-board reagent reservoirs (diluent, lysing fluid, and sheath fluid), whole-blood sample acquisition capillaries, and on-board liquid flow sensors. The cytometer system may include automated sample preparation on the cartridge, red-VCSEL-array-based electronic self-alignment, highly miniaturized three-channel pumping system, and custom-developed electronics and graphic user interface.

Figure 1:
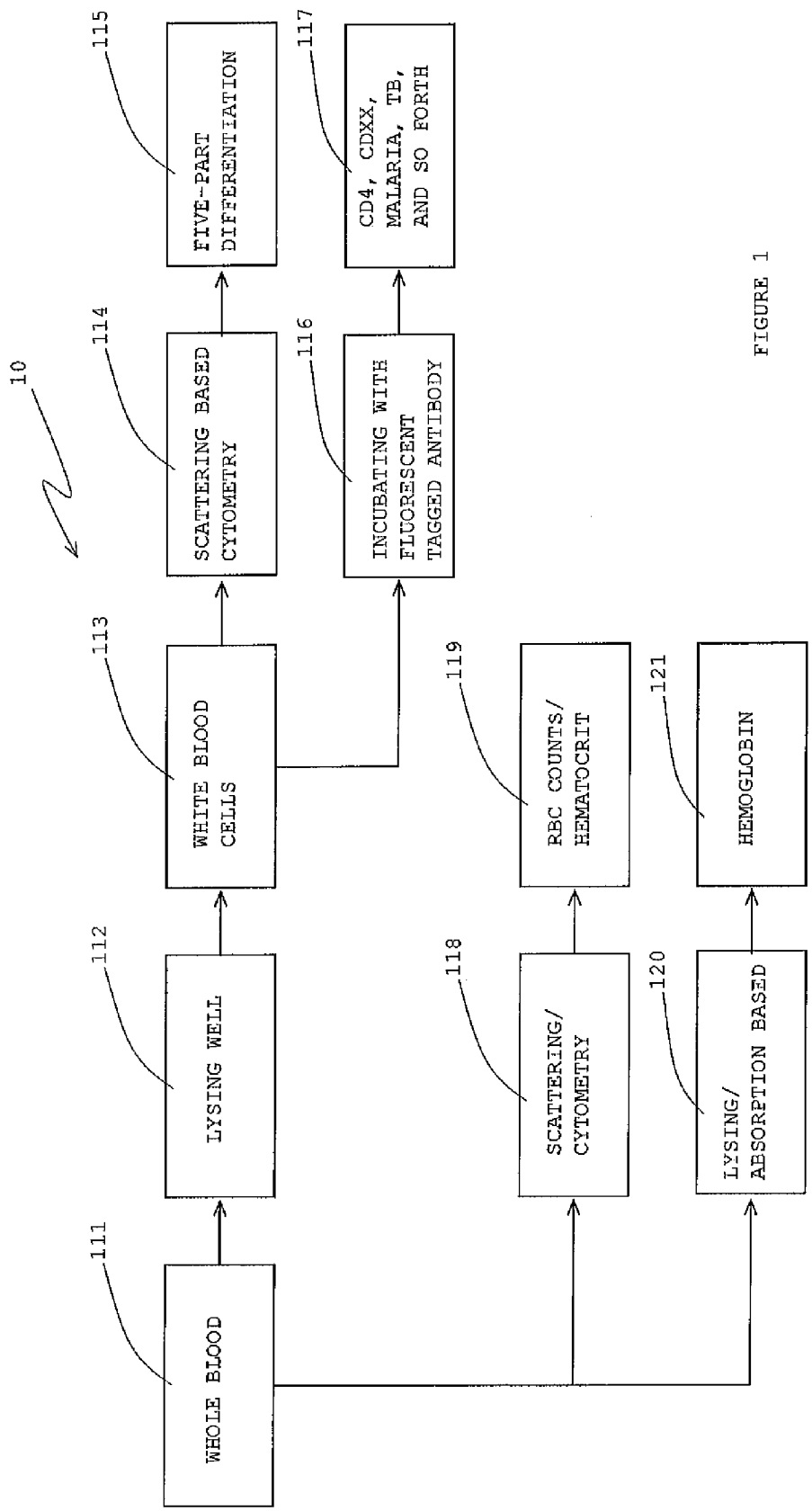
FIG. 1 is a block diagram of a point of care instrument.

FIG. 1 is a block diagram of a point of care (POC) instrument and its operations. A sample of whole blood may be brought in at block 111. Some of the whole blood may be moved through a lysing well 112 to remove red cells so as to primarily get white blood cells at block 113. Some of the white blood cells may go to scattering based cytometry at block 114 and result in a count and five-part differentiation of the white blood cells at block 115.

From block 113, some white blood cells may also go to block 116 for incubating with fluorescent tagged antibodies. This is for attaining information about an indication and/or amount of CD4, CDXX, malaria parasites, tuberculosis (TB), and so forth, at block 117.

Also from block 111, some of the whole blood may go to a scattering and cytometry block 118 to get RBC counts and hematocrit data. Again, also from block 111, whole blood may to block 120 for lysing and absorption based information on the amount of hemoglobin in the blood. The items in the blocks of FIG. 1 may be implemented on a microfluidic cartridge or card, which may be regarded as a hematology analyzer. One of the primary goals of the cartridge is to obtain complete blood count parameters which may include red blood cell count, white blood cell count, hemoglobin amount, hematocrit data, platelet count, and a five part differentiation of the white blood cells. Blocks 115, 119 and 121 may provide the complete blood count. Block 117 may provide analysis with fluorescence. The two major operations may be implemented on and achieved by a microfluidic cartridge, which may be as small as an ordinary credit card and disposable.

After differentiation of the white cells into the five groups, one or more of these groups may be further differentiated into subgroups. One of the groups, lymphocytes, may be tagged with a fluorescent or fluoro tag or marker. The cell may have an antigen and antibodies from a reservoir which may be provided on the cartridge, and an antibody may bind to a certain antigen. The subgroupings of the lymphocytes may have clinical significance. The subgroupings may result in groups of CD4, CD45, CDX, CDXX cells to allow doctors to note and/or deduce pathogens and the like, and to monitor HIV, AIDS, malaria, TB, and so on, of patients. Even monocytes may be labeled with fluorescent markers. The antibodies may be tagged to reduce a false alarm rate.

It may be noted that although co-infection with HIV and malaria may cause increased mortality, this co-infection may be less of a problem than an HIV/tuberculosis co-infection, due to the two diseases usually attacking different age-ranges, with malaria being most common in the young and tuberculosis most common in the old. However, in areas of unstable malaria transmission, HIV may contribute to the incidence of severe malaria in adults during malaria outbreaks.

There may also be a high correlation between HIV and malaria. This correlation has lead to a suggestion that malaria itself is a major contributor to the spread of HIV. Higher viral load may cause more HIV transmission, and malaria may cause high HIV viral load. This apparent causal relationship may be a reason for an assay test to have the capability of determining whether a patient has HIV, malaria and/or TB.

Malaria may be one of the most common infectious diseases and an enormous public-health problem. The disease is regarded as being caused by protozoan parasites of the genus *Plasmodium*. The most serious forms of the disease may be caused by *Plasmodium falciparum* and *Plasmodium vivax*, but other related species (*Plasmodium ovale* and *Plasmodium malariae*) may also infect humans. This group of human-pathogenic *Plasmodium* species is often referred to as malaria parasites.

FIG. 2 is graph of a five-part differentiation of white cells based on data of small angle scattering versus large angle scattering plotted on the ordinate and abscissa axes, respectively, resulting in a plot of the five groups 131, 132, 133, 134 and 135 of white blood cells. FIG. 3 shows a white blood cell 136, such as a lymphocyte, having an antigen 137 with an antibody 138 coming to it to match up like a key and lock. The respective cell may ultimately come from whole blood with an antigen on it.

FIG. 4a is a three dimensional plot of lymphocytes with orthogonal measurements for the plotted data. The data are 3-D plotted with fluoro intensity (which indicates how many cells are labeled by the antibody) versus FALS on a plane parallel to the sheet with FIG. 4a, with a third coordinate for SALS extending out from the sheet. FIG. 4a shows a two peak (141 and 142) perspective. FIG. 4b shows an example cell 143 from a viewing direction looking towards the side of the graph of FIG. 4a. The graph of FIG. 5a is like that of FIG. 4a except the first peak appears smaller in amplitude which may indicate a poor body response. Peak 141 of FIG. 4a may indicate a good body response. A ratio of peak 141 to peak 142 may provide certain information of the health of the subject. FIG. 5b shows the plot of SALS versus Fluoro revealing peaks 141 and 142.

Various parameters may be useful for a hematology analysis. Four significant parameters, a red blood cell (RBC) count (cells/μL), a platelet (PLT) count (cells/μL), a mean cell volume (MCV), and a red cell distribution width (RDW) may be attained with an optical approach upon a blood sample. MCV is effectively a measurement of the average size of the RBCS. RDW is the variation of the size among the RECs. A greater variation of the sizes of the RBCs, the greater is the RDW.

An RBC count is an actual number of RBCs per unit volume of the blood under analysis. Hct is hematocrit which is RBC×MCV, and may amount to a measure of oxygen carrying capacity of the blood (i.e., total capacity of all of the cells in the unit volume under analysis). Hct may also be regarded as an amount of space that the RBCs take up in the blood, or the proportion of the whole blood that is composed of red blood cells. MCH is the "mean cell hemoglobin" which is effectively the amount of hemoglobin in each RBC. MCH may be regarded as the mean or approximately an average mass of hemoglobin in an individual RBC, in units of picograms. MCH=Hb÷RBC. Hb is the amount of hemoglobin per unit volume of the sample under analysis. MCHC is the "mean cell hemoglobin concentration" which may be regarded as the concentration of hemoglobin per unit volume in each of the RBCs. MCHC=Hb÷Hct.

A set of some measured parameters may include cell flow rate (FR), measurement time (T), dilution factor (DF), number of RBCs counted ($N_{RBC}$), number of platelets counted ($N_{PLT}$), the amount of hemoglobin (Hb), and the diameter (microns) of virtually each cell$_i$ (drbc$_i$). <drbc$_i$> is the average of the measured cell diameters of the cells, denoted by the set {drbc$_i$}. Some of the major calculated parameters may include: RBC=$N_{RBC}$÷(DF×FR×T); PLT=$N_{PLT}$÷(DF×FR×T); MCV=$(\pi/6)$×<drbc$_i^3$>; and RDW=SD{[$(\pi/6)$drbc$_i^3$]}÷MCV, where SD denotes the standard deviation of the measured quantities.

Calculated parameters may include: Hct=RBC×MCV; MCHC=Hb÷Hct; and MCH=MCHC×MCV.

Module 121 may be used for determining an amount of hemoglobin (Hb) or hemoglobin concentration in the blood sample. The module may use hemoglobin absorption to determine the Hb. The amount of hemoglobin in the blood may be expressed in grams per liter.

Figure 6B:
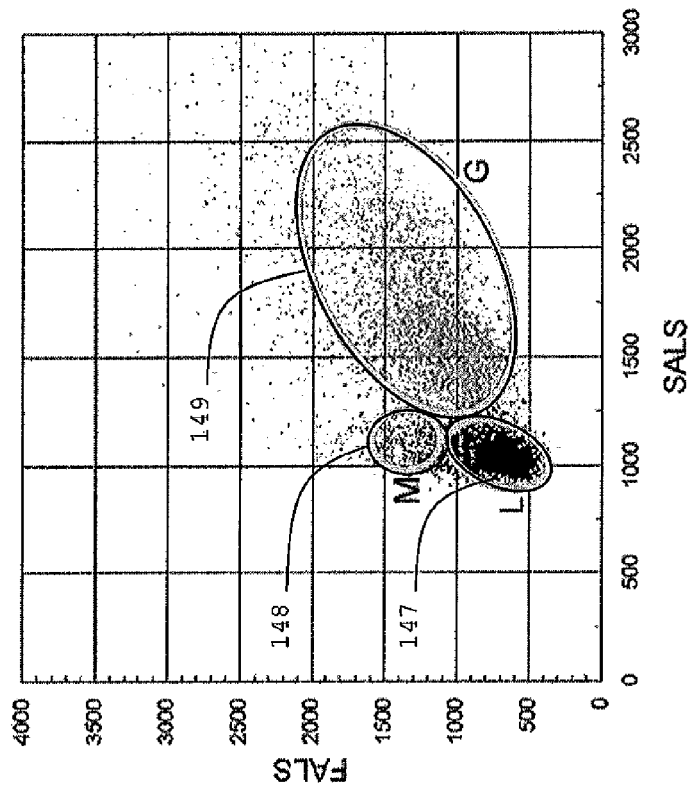
FIG. 6b shows a graph of a differentiation of three kinds of white blood cells.
Figure 6A:
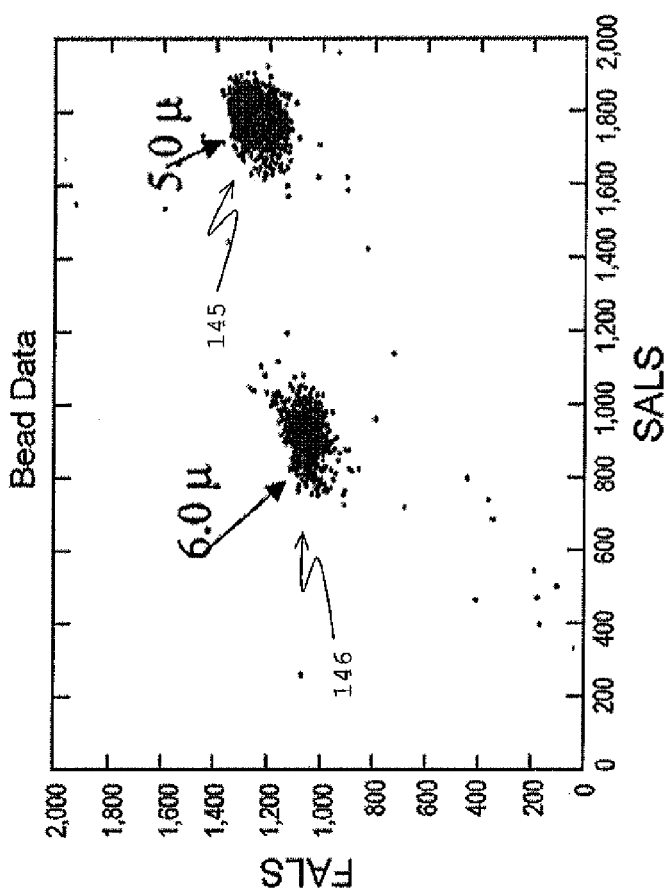
FIG. 6a shows a graph of counting and classification of beads having several sizes.

Repeatable three-part white blood cell differentiation may be successfully demonstrated as shown in FIGS. 6a and 6b. FIG. 6a shows a graph of counting and classification of 5- and 6-μm beads, shown as groups 145 and 146, respectively. The plot is FALS versus SALS of the beads. The absolute count for each bead type appears to be within about five percent of the expected values. FIG. 6b shows results for a white blood cell plot from scattering data showing several groupings of the cells. The plot is FALS versus SALS of the cells according a point of care type of instrument. Three groups 147, 148 and 149 of white blood cells (lymphocytes, L, monocytes, M, and granulocytes, G, respectively) may be differentiated in the plot of FIG. 6b. The total WBC count appeared within 6 percent of a similar measurement made on the same sample using a commercial hematology analyzer.

Red VCSEL arrays may provide a solution to one of the most critical aspects in flow cytometry which may include the alignment of the focused laser spot with particle flow path. Typically, alignment in molded plastic parts such as disposable fluidic cartridges is challenging due to some imprecision associated with the use of such parts. Replacing a standard single laser with a linear array of lasers provides a way of determining a virtually exact path of a particular cell and allowing for self-alignment.

The present POC cytometer may include microfluidic circuitry for whole-blood sample acquisition, reagent storage, continuous lysing of red blood cells, a three-dimensional hydrodynamic/geometric focusing of leukocytes into a blood-cell-sized core for flow cytometry, and sample and waste storage chambers. It may work directly from a single droplet (15 μL) of blood without any preparatory steps, minimize reagent use, and retain the sample, reagents, and waste on-card.

Liquid flow in the micro-scale channels on the analysis cartridges may be laminar in nature, allowing miscible fluids (e.g., whole blood and water) to flow next to each other, mixing only through molecular and convective diffusion. This may enable exposure of biological particles (such as blood cells) for a controlled time duration, allowing selective lysing of red blood cells (RBC) via chemical and osmotic pressure so that the remaining white blood cells can be detected and characterized. This approach for the selective lysing of RBCs on a cartridge, termed "lysing-on-the-fly" (LOF), may offer an advantage of all cells exposed to lysing agents for a same amount of time, unlike batch lysis performed in benchtop cytometers.

In addition to the present light-scattering-based POC cytometer, there may be two other ongoing aspects that benefit the POC cytometer. Two-color light fluorescence capability on the light-scattering-based instrument may be used to perform a CD4/CD45 assay. The POC may also be an integrated scattering/fluorescence cytometer capable of a CD4, CD45, CD34, CDX, CDXX, and/or the like assay. The disposable card or cartridge may permit on-card staining of white blood cells with on-card mAbs and red cell lysing. The present POC hematology analyzer may be designed as a CLIA-waived instrument to perform the complete blood count (CBC) test.

Figure 7:
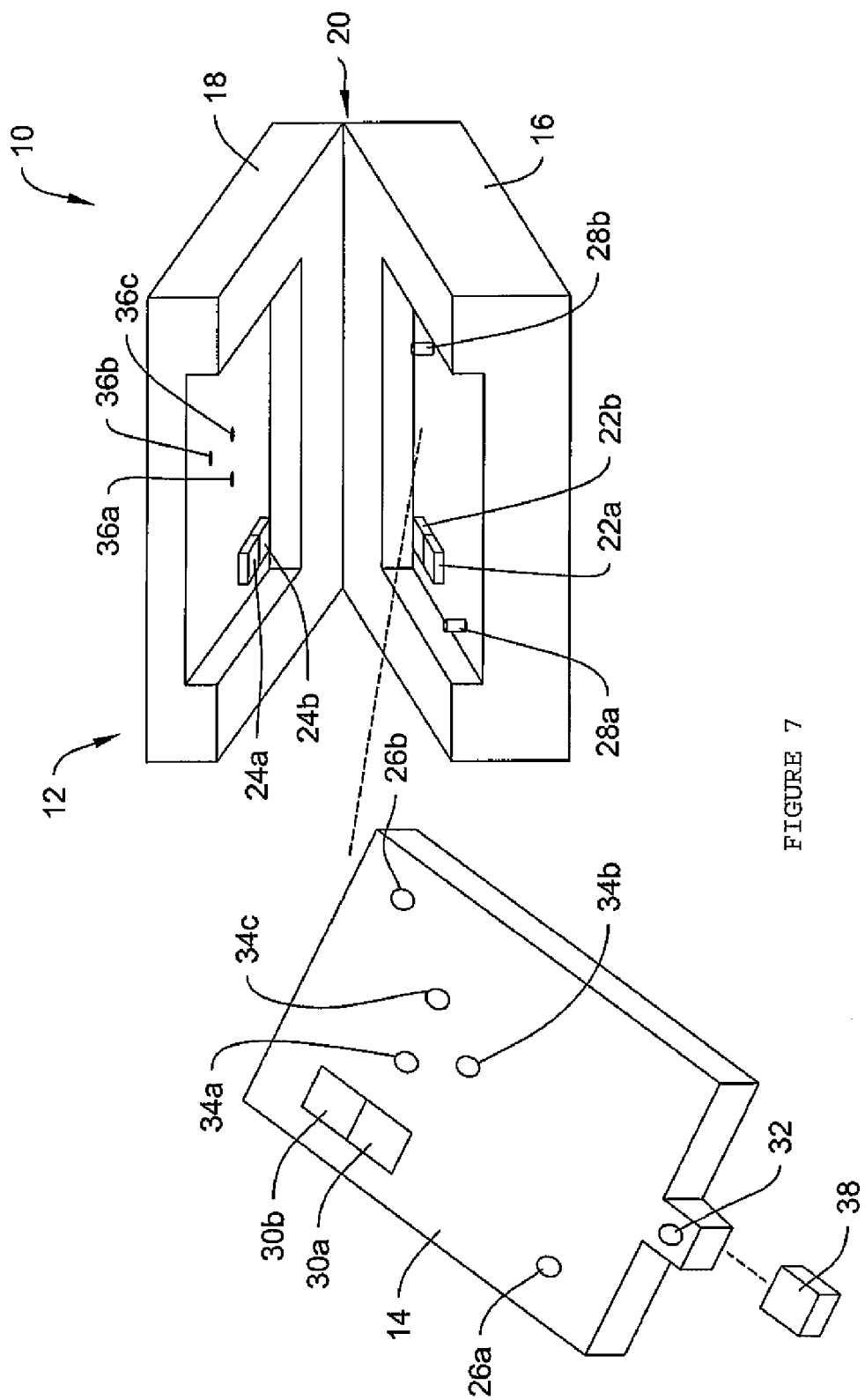
FIG. 7 is a perspective view of a miniaturized portable cytometer.

FIG. 7 is a perspective view of an illustrative miniaturized portable cytometer. A version of this cytometer may be used conjunction with the present invention. The cytometer is generally shown at 10, and may include a housing 12 and a removable or replaceable cartridge 14. The illustrative housing 12 may include a base 16, a cover 18, and a hinge 20 that attaches the base 16 to the cover 18. The base 16 may include light sources 22a and 22b, associated optics and the necessary electronics for operation of the cytometer. The cover 12 may include a manual pressurizing element, pressure-chambers with control microvalves, and light detectors 24a and 24b with associated optics.

The removable cartridge 14 may receive a sample fluid via a sample collector port 32. A cap 38 may be used to protect the sample collector port 32 when the removable cartridge 14 is not in use. The removable cartridge 14 may perform blood dilution, red cell lysing, and hydrodynamic focusing for core formation. The removable cartridge 14 may be constructed with fluidic circuits, some of which may be fabricated using a laminated structure with etched channels.

The removable structure or cartridge 14 may be inserted into the housing when the cover 18 is in the open position. The removable cartridge 14 may include holes 26a and 26b for receiving registration pins 28a and 28b in the base 16, which help provide alignment and coupling between the different parts of the instrument. The removable cartridge 14 also may include transparent flow stream windows 30a and 30b, which are in alignment with the arrays of the light sources 22a and 22b, and light detectors 24a and 24b. When the cover is moved to the closed position, and the system is pressurized, the cover 18 may provide controlled pressures to pressure receiving ports 34a, 34b, and 34c in the removable cartridge 14 via pressure providing ports 36a, 36b and 36c, respectively.

To initiate a test, the cover 18 may be lifted and a new cartridge 14 placed and registered onto the base 16. A blood sample may be introduced into the sample collector 32. The cover 18 may be closed and the system manually pressurized. Pressurization may other than manual. Once pressurized, the instrument may perform a white blood cell cytometry measurement and other measurements. The removable cartridge 14 may provide blood dilution, red cell lysing, and hydrodynamic focusing for core formation. The light sources 22a and 22b, light detectors 24a and 24b and associated control and processing electronics may perform differentiation and counting of white blood cells based on light scattering fluorescent signals. Rather than using a hinged construction for the housing 12, it is contemplated that a sliding cartridge slot or any other suitable construction may be used.

Figure 8:
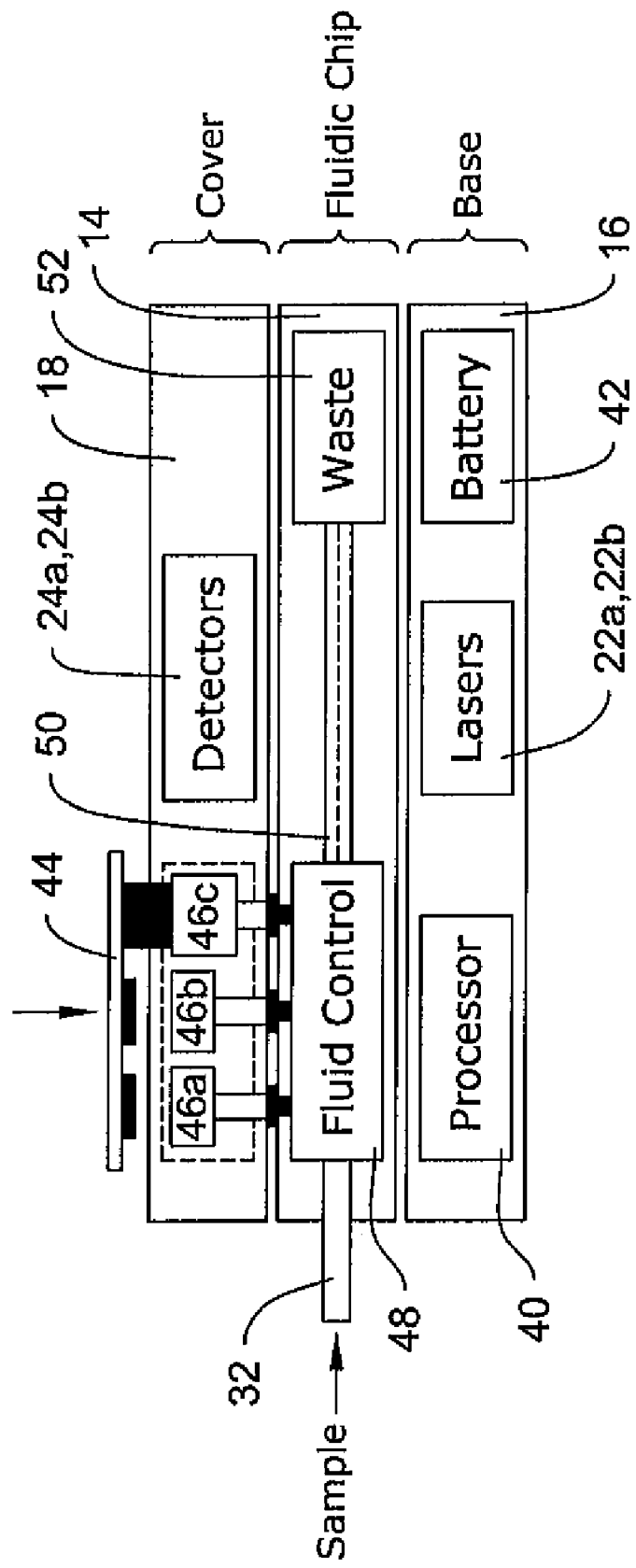
FIG. 8 is a schematic view of the miniaturized cytometer.

FIG. 8 is a schematic view of the illustrative cytometer of FIG. 7. As above, the base 16 may include light sources 22a and 22b, associated optics and the necessary control and processing electronics 40 for operation of the cytometer. The base 16 may also include a battery 42 for powering the cytometer. The cover 18 is shown having a manual pressurizing element 44, pressure-chambers 46a, 46b and 46c with control microvalves, and light detectors 24a and 24b with associated optics.

The removable cartridge 14 may receive a sample fluid via the sample collector port 32. When pressurized by the cover 18, the removable cartridge 14 may perform blood dilution, red cell lysing, and hydrodynamic focusing for core formation in the present device. Once formed, the core may be provided down a flow stream path 50, which passes the flow stream windows 30a and 30b of FIG. 7. The light sources 22a and 22b, and associated optics in the base may provide light through and to the core stream via the flow stream windows 30a and 30b. The light detectors 24a and 24b, and associated optics may receive scattered and non-scattered light from the core, also via the flow stream windows 30a and 30b, respectively. The controller or processor 40 may receive output signals from the detectors 24a and 24b, and differentiate, identify and count selected white blood cells that are present in the core stream.

The removable cartridge 14 may include a fluid control block 48 for helping control the velocity of each of the fluids. In the illustrative example, the fluid control block 48 may include flow sensors for sensing the velocity of the various fluids and report the velocities to the controller or processor 40. The controller or processor 40 may then adjust the microvalves associated with pressure-chambers 46a, 46b and 46c to achieve the desired pressures and thus desired fluid velocities for proper operation of the cytometer.

Because blood and other biological waste can spread disease, the removable cartridge 14 may have a waste reservoir 52 downstream of the flow stream windows 30a and 30b. The waste reservoir 52 may receive and store the fluid of the flow stream in the removable cartridge 14. When a test is completed, the removable cartridge may be removed and disposed of in a container compatible with biological waste.

Figure 9:
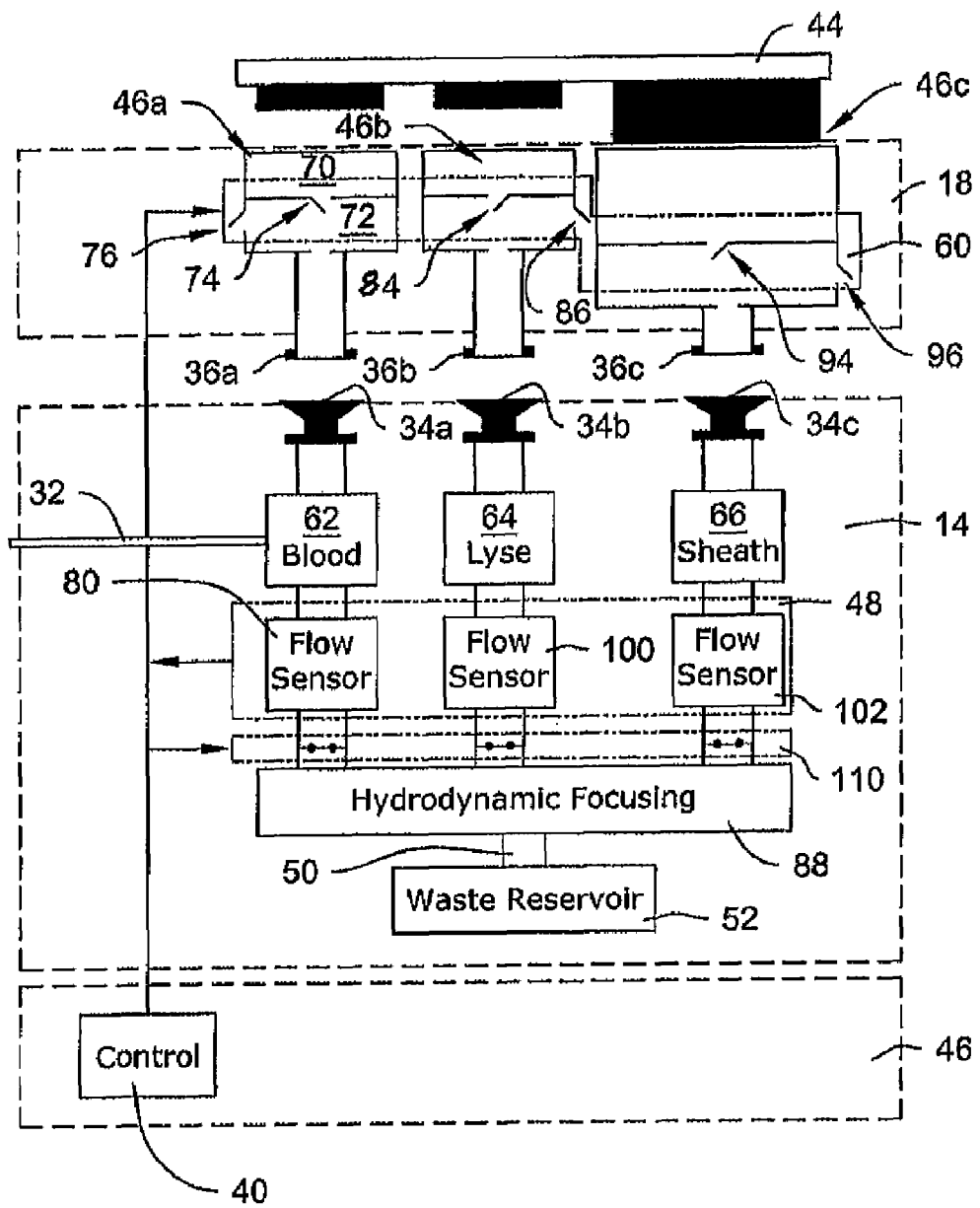
FIG. 9 is a more detailed schematic of the miniaturized cytometer without the cover depressed.
Figure 10:
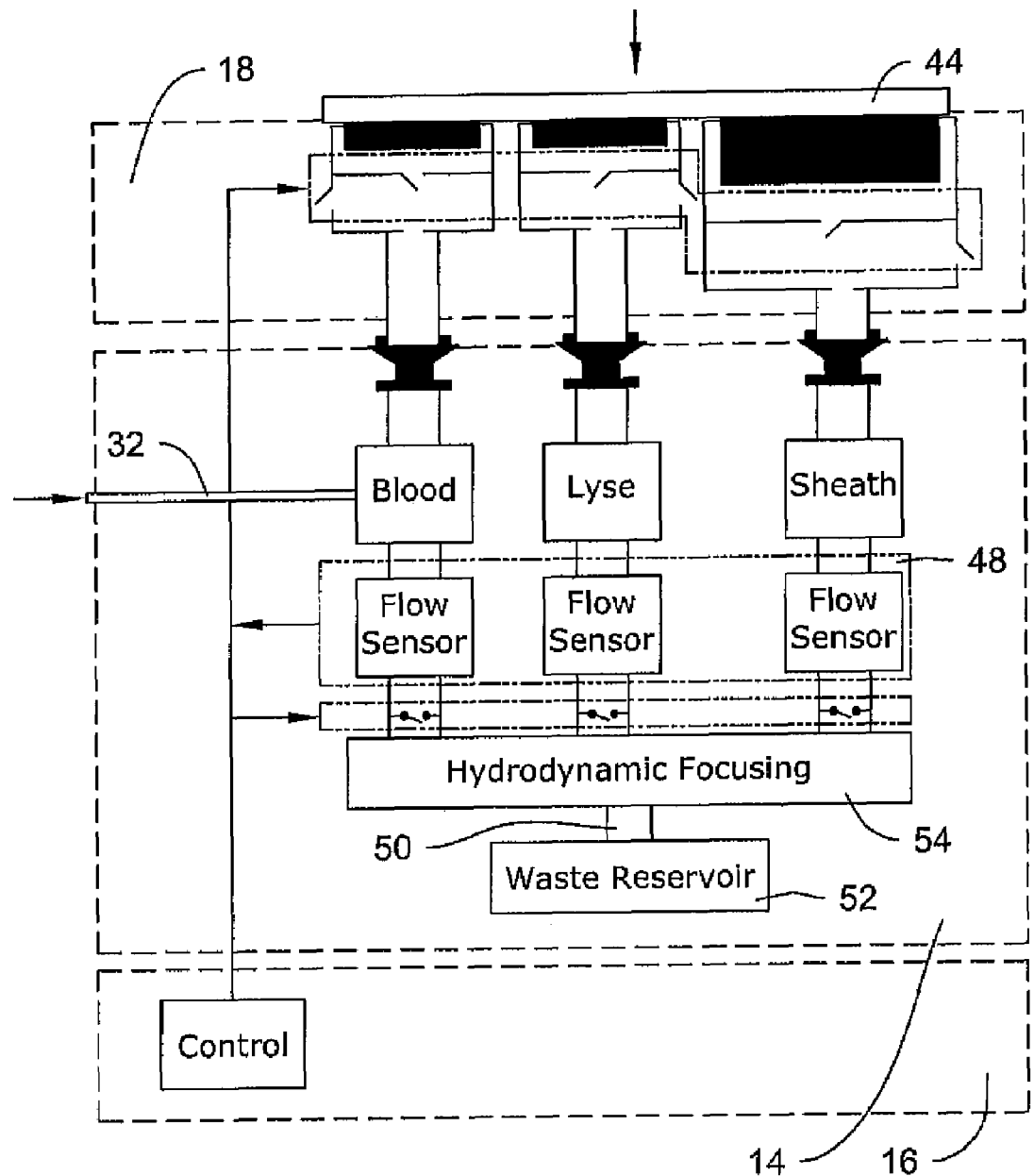
FIG. 10 is a more detailed schematic of the miniaturized cytometer with the cover depressed.

FIG. 9 is a more detailed schematic diagram showing the cytometer of FIG. 8 with the cover 18 not yet depressed. FIG. 10 is a more detailed schematic diagram showing the cytometer of FIG. 8 with the cover depressed. The cover 18 is shown having a manual pressurizing element 44, pressure-chambers 46a, 46b and 46c, and control microvalves generally shown at 60. The light sources and detectors are not shown in these Figures.

There may be three pressure chambers 46a, 46b and 46c, one for each fluid to be pressurized. In the illustrative example, pressure chamber 46a may provide pressure to a blood sample reservoir 62. Pressure chamber 46b may provide pressure to a lyse reservoir 64, and pressure chamber 46c may provide pressure to a sheath reservoir 66. The size and shape of each pressure chamber 46a, 46b and 46c may be tailored to provide the desired pressure characteristics to the corresponding fluid.

Pressure chamber 46a may include a first pressure chamber 70 and a second pressure chamber 72. A first valve 74 may be provided between the first pressure chamber 70 and the second pressure chamber 72 for controllably releasing the pressure in the first pressure chamber 70 to a second pressure chamber 72. A second valve 76, in fluid communication with the second pressure chamber 72, may controllably vent the pressure in the second pressure chamber 72. Each valve may be an array of electrostatically actuated microvalves that are individually addressable and controllable. Pressure chambers 46b and 46c may include similar valves to control the pressures applied to the lyse reservoir 64 and sheath reservoir 66, respectively. Alternatively, each valve may be an array of electrostatically actuated microvalves that are pulse modulated with a controllable duty cycle to achieve a controlled "effective" flow or leak rate.

The removable cartridge 14 may have pressure receiving ports 34a, 34b, and 34c for receiving the controlled pressures from the cover 18. The controlled pressures may be provided to the blood reservoir 62, lyse reservoir 64 and sheath reservoir 66, as shown. The lyse reservoir 64 and sheath reservoir 66 may be filled before the removable cartridge 14 is shipped for use, while the blood reservoir 62 is filled from sample collector port 32. A blood sample may be provided to the sample collector port 32, and through capillary action, the blood sample may be sucked into the blood reservoir 62. Once the blood sample is in the blood reservoir 62, the cover 18 may be closed and the system may be pressurized.

A flow sensor may be provided in-line with each fluid prior to hydrodynamic focusing. Each flow sensor 80, 100 and 102 may measure the velocity of the corresponding fluid. The flow sensors may be thermal anemometer type flow sensors, or microbridge type flow sensors. An output signal from each flow sensor 80, 100 and 102 may be provided to controller or processor 40. The controller or processor 40 may open the first valve 74 when the velocity of the blood sample drops below a first predetermined value and open the second valve 76 when the velocity of the blood sample increases above a second predetermined value. Valves 84, 86, 94 and 96 may operate in a similar manner to control the velocities of the lyse and sheath fluids.

During operation, and to pressurize the system, the manual pressurizing element 44 may be depressed. The pressure element may be substituted with a non-manual mechanism. In the example shown, the manual pressurizing element 44 may include three plungers, with each plunger received within a corresponding one of the first pressure chambers. The plungers may create a relatively high non-precision pressure in the first pressure chambers. Lower, controlled pressures may be built in the secondary chambers by opening the first valves 74, 84 and 94, which produce a controllable leak into the secondary chambers. If too much pressure builds up in the secondary pressure chambers, the corresponding vent valves 76, 86 and 96 may be opened to relieve the pressure.

When closing the cover 18, the normally open first valves 74, 84 and 94 may be closed while the vent valves 76, 86 and 96 are open. When a predetermined pressure P is achieved in the first pressure chambers, the vent valves 76, 86 and 96 may be closed, and the first valves 74, 84 and 94 may be opened to build a lower pressure P' in the secondary pressure chambers. The controlled pressure in the secondary pressure chambers may provide the necessary pressures to the fluidic circuit of the removable cartridge 14 to produce fluid flow for the blood, lyse and sheath. The velocity of the fluid flow may then be measured by the downstream flow sensors 80, 100 and 102. Each flow sensor may provide an output signal that is used by the controller or processor 40 to control the operation of the corresponding first valve and vent valve to provide a desired and constant flow rate for each fluid.

Downstream valves generally shown at 110 may also be provided. Controller or processor 40 may close downstream valves 110 until the system is pressurized. This may help prevent the blood, lyse and sheath from flowing into the fluid circuit before the circuit is pressurized. In another illustrative example of the invention, downstream valves 110 may be opened by mechanical action when the cover is closed.

Figure 11:
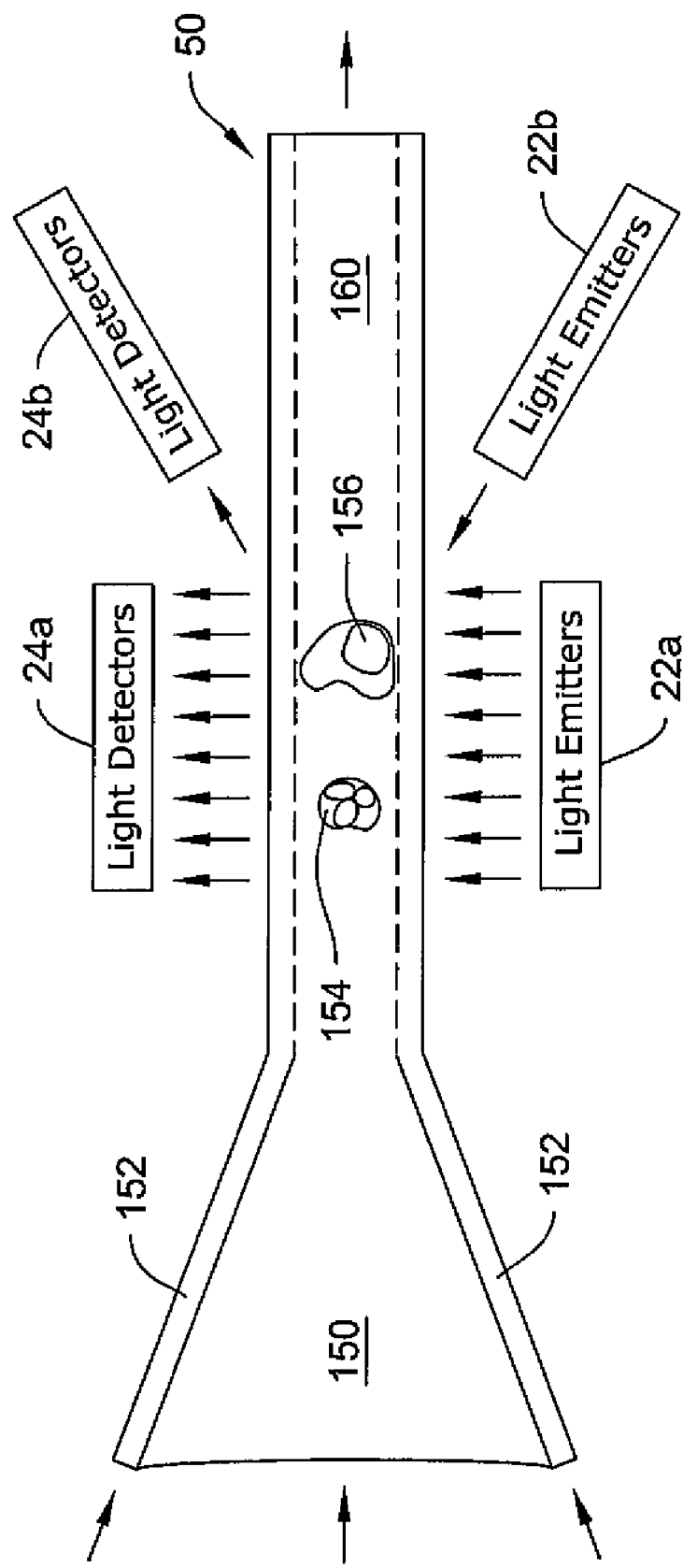
FIG. 11 is a diagram showing the formation of a flow stream and core by a hydrodynamic focusing component.

FIG. 11 is a schematic diagram showing the formation of a flow stream and core by the hydrodynamic focusing block 88 of FIG. 9. The hydrodynamic focusing block 88 may receive blood, lyse and sheath at controlled velocities from the fluid driver. The blood may be mixed with the lyse, causing the red blood cells to be removed. The lysing solution may have a pH lower than that of the red blood cells. This may often be referred to as red cell lysing or lyse-on-the-fly. The remaining white blood cells may be provided down a central lumen 150, which may be surrounded by sheath fluid to produce a flow stream 50. The flow stream 50 may include a core stream 160 surrounded by the sheath fluid 152. The dimensions of the channel may be reduced as shown so that the white blood cells 154 and 156 are in single file. The velocity of the sheath fluid may be about 9 times that of the core stream 160. However, the velocity of the sheath fluid and core stream 160 may remain sufficiently low to maintain laminar flow in the flow channel.

Light emitters 22a and 22b, and associated optics may be provided adjacent one side of the flow stream 50. Light detectors 24a and 24b, and associated optics may be provided on another side of the flow stream 50 for receiving the light from the light emitters 22a and light from fluorescing particles via the flow stream 50. The output signals from the light detectors 24a and 24b may be provided to controller or processor 40, wherein they are analyzed to identify and/or count selected white blood cells in the core stream 160.

Figure 12:
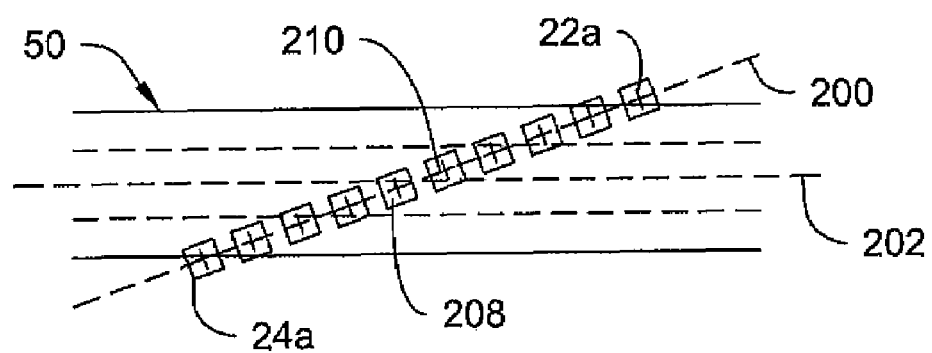
FIG. 12 is a diagram of arrays of light sources and detectors for analysis of a core stream.

FIG. 12 is a schematic diagram showing an array 22a of light sources and an array 24b of light detectors for analysis of the core stream 160 via scattering of FIG. 11. The light sources are shown as "+" signs and the detectors are shown at boxes. In the example shown, the array of light sources may be provided adjacent one side of the flow stream 50, and the array of light detectors be provided adjacent the opposite side of the flow stream. Each of the light detectors may be aligned with a corresponding one of the light sources. The array of light sources and the array of light detectors are shown arranged along a light source axis 200 that is slightly rotated relative to the axis 202 of the flow stream 50.

The array 22a of light sources may be an array of lasers such as vertical cavity surface emitting lasers (VCSELs) fabricated on a common substrate. Because of their vertical emission, VCSELs may be suited for packaging in compact instruments such as a miniaturized portable cytometer. Such cytometer may be wearable on a person's body. The VCSELs may be "red" VCSELs that operate at wavelengths that are less than the conventional 850 nm, or specifically in the 670 nm to 780 nm range. Red VCSELs may have a wavelength, power and polarization characteristic that is suited for scatter measurements.

Some cytometer bench models may use a single 9 mW edge-emitting laser with a wavelength of 650 nm. The beam may be focused to a 10×100 micron elongated shape to cover the uncertainty in particle position due to misalignment and width of the core stream. In contrast, the output power of the red VCSELs of the present invention, operating at 670 nm, may typically be around 1 mW for a 10×10 micron emitter and 100-micron spacing. Thus, the total intensity of the light from a linear array of ten red VCSELs may be essentially the same as that of some prior art bench models.

Using a linear array of lasers oriented at an angle with respect to the flow axis 202 may offer a number of important advantages over a single light source configuration. For example, a linear array of lasers may be used to determining the lateral alignment of the path of the particles in the core steam. One source of uncertainty in the alignment of the particle stream may be the width of the core flow, which can lead to statistical fluctuations in the particle path position. These fluctuations may be determined from analysis of the detector data and can be used by the controller or processor 40 to adjust the valves of the fluid driver in order to change the relative pressures that are applied to the sample fluid and the supporting fluids to change the alignment of the selected particles in the flow stream.

Figure 13:
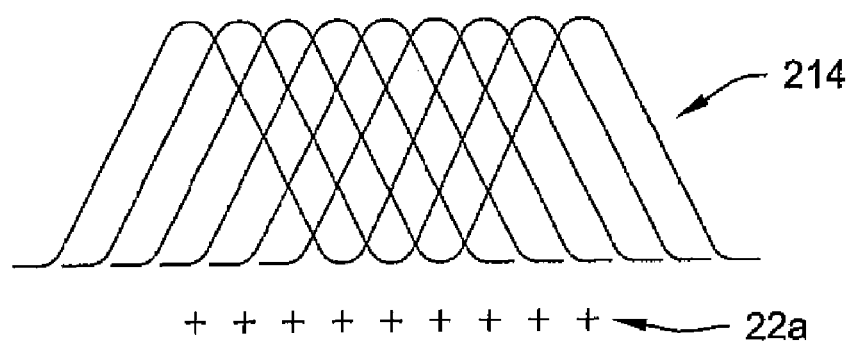
FIG. 13 is a diagram of Gaussian spots of light.

To determine the lateral alignment of the cells in the fluid stream 50, the cells may pass through several focused spots produced by the linear array of VCSELs. The cells may produce a drop in signal in the corresponding in-line reference detectors. The relative strengths of the signals may be used by the controller or processor 40 to determine the center of the particle path and a measure of the particle width;

For determining particle path and size, the lasers 22a may be focused to a series of Gaussian spots 214 (intensity on the order of 1000 W/cm$^2$) in the plane of the core flow. The spots 214 may be about the same size as a white blood cell (10-12 um). Illustrative Gaussian spots 214 are shown in FIG. 13. Arrays 24a of detectors and their focusing optics may be provided on the opposite side of the fluid stream 50. Lenses with fairly large F-numbers may be used to provide a working space of several hundred microns for the cytometer section of the removable cartridge.

Another advantage of using a linear array 22a of lasers rather than a single laser configuration is that the velocity of each cell may be determined. Particle velocity can be an important parameter in estimating the particle size from light scatter signals. In some cytometry, the particle velocity may be extrapolated from the pump flow rates. A limitation of this approach is that the pumps should be very precise, the tolerance of the cytometer flow chambers should be tightly controlled, no fluid failures such as leaks should occur, and no obstructions such as microbubbles should be introduced to disturb the flow or core formation.

To determine the velocity of each cell, the system may measure the time required for each cell to pass between two adjacent or successive spots. For example, and with reference to FIG. 12, a cell may pass detector 208 and then detector 210. By measuring the time required for the cell to travel from detector 208 to detector 210, and by knowing the distance from detector 208 to detector 210, the controller or processor 40 may calculate the velocity of the cell. This would be an approximate velocity measurement. This is often referred to as a time-of-flight measurement. Once the velocity is known, the time of travel through the spot on which the particle is centered (a few microseconds) may provide a measure of particle length and size.

It is contemplated that the particle velocity can also be used to help control the fluid driver. To reduce the size, cost and complexity of the present invention, the replaceable cartridge of FIG. 7 may be manufactured from a plastic laminate or molded parts. While such manufacturing techniques may provide inexpensive parts, they are typically less dimensionally precise and repeatable, with asymmetrical dimensions and wider tolerance cross-sections. These wider tolerances may produce variations in particle velocity, particularly from cartridge to cartridge. To help compensate for these wider tolerances, the time-of-flight measurement discussed herein may be used by the controller or processor 40 to adjust the controlled pressures applied to the blood, lyse and sheath fluid streams such that the particles in the core stream have a relatively constant velocity.

To further evaluate the cell size, it is contemplated that laser beams may be focused both along the cell path and across the cell path. Additionally, multiple samples across the cell may be analyzed for texture features, to correlate morphological features to other cell types. This may provide multiple parameters about cell size that may help separate cell types from one another.

Another advantage of using a linear array 22a of lasers rather than a single layer configuration is that a relatively constant light illumination may be provided across the flow channel. This may be accomplished by overlapping the Gaussian beams 214 from adjacent VCSELs 22a, as shown in FIG. 13. In single laser systems, the light illumination across the flow channel may vary across the channel. Thus, if a particle is not in the center of the flow channel, the accuracy of subsequent measurements may be diminished.

Figure 14:
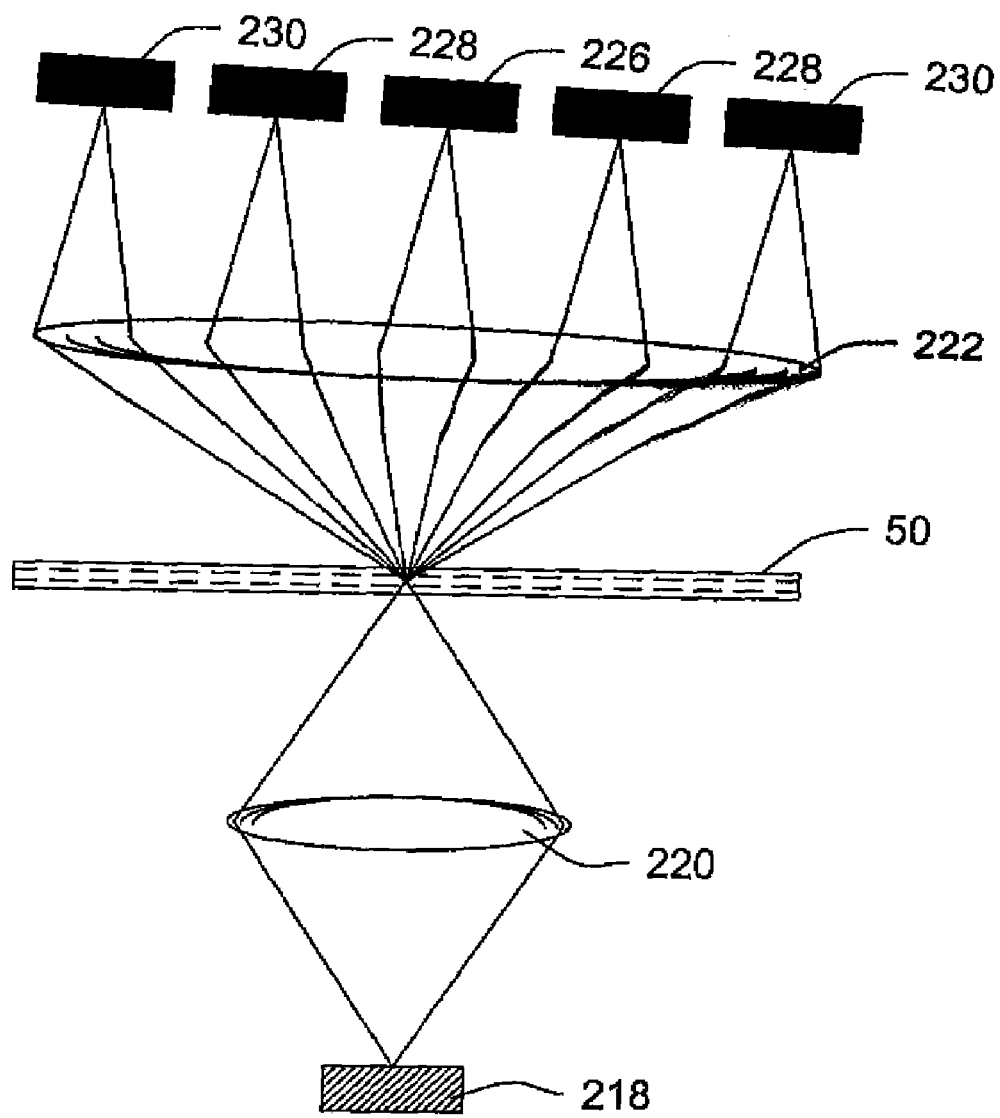
FIG. 14 is a diagram of a light source and detector arrangement for light scatter.

To perform the above described measurements, each detector 24a in FIG. 12 may be a single in-line detector. To measure FALS and SALS scatter, however, each detector 24a may further include two annular detectors disposed around the in-line detector, as shown in FIG. 14. Referring to this Figure, a VCSEL 218 is shown providing light in an upward direction. The light may be provided through a lens 220, which can focus the light to a Gaussian spot in the plane of the core flow. Lens 220 may be a microlens or the like, which is either separate from or integrated with the VCSEL 218. The light may pass through the core flow, and be received by another lens 222, such as a diffractive optical element. Lens 222 may provide the light to in-line detector 226 and annular detectors 228 and 230. The in-line detector 226 may detect the light that is not significantly scattered by the particles in the core stream. Annular detector 228 may detect the forward scatter (FALS) light, and annular detector 230 may detect the small angle scatter (SALS) light.

Figure 15:
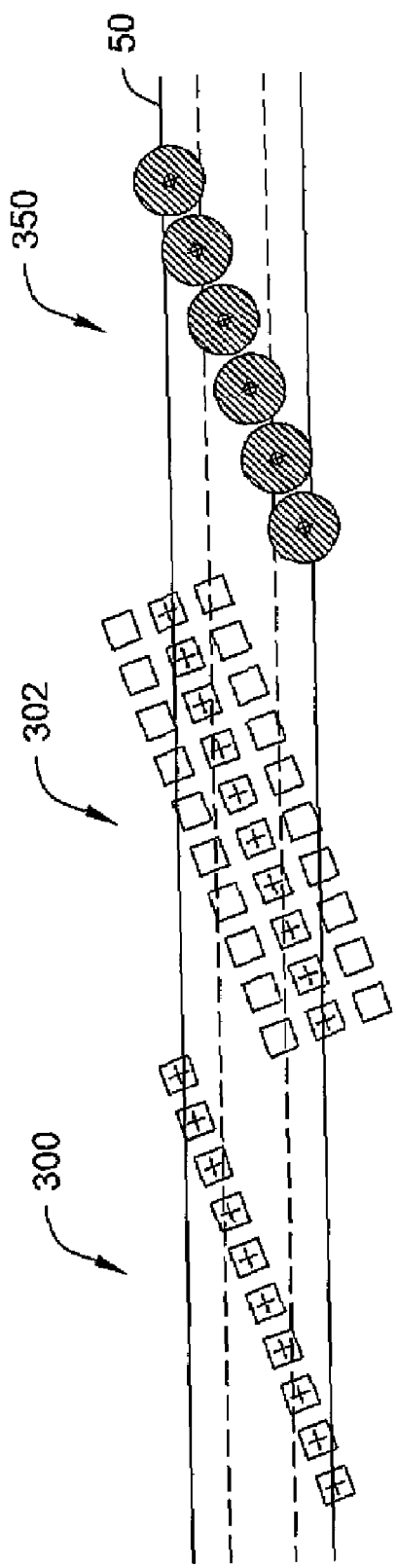
FIG. 15 is a diagram of three sets of light sources and corresponding detectors proximate to a flow channel.

FIG. 15 shows another illustrative example that may include three separate arrays of light sources and light detectors. Each array of light sources and light detectors may be positioned along a different light source axis that is slightly rotated relative to the central flow axis of the flow stream. By using three arrays, the optics associated with each array may be optimized for a particular application or function. For detecting small angle scattering (SALS), laser light that is well-focused on the plane of the core flow is desirable. For detecting forward scattering (FALS), collimated light is desirable.

Referring to FIG. 15, a first array of light sources and light detectors is shown at 300. The light sources and light detectors may be arranged in a linear array along a first light source axis. The first light source axis may be rotated relative to the flow axis of the flow stream. The light sources and light detectors may be similar to that described above with respect to FIG. 12, and may be used to measure, for example, the lateral alignment of the cells in the flow stream, the particle size, and the velocity of the particles.

As indicated above, the user may obtain a removable cartridge and provide a blood sample to the sample collector port 32 (see FIG. 7) of the removable cartridge. The blood sample may be collected by, for example, a finger prick. The user may then insert the removable cartridge into the housing, and manually pressurize the system. The miniaturized portable cytometer may then provide a reading that indicates if the user should seek medical treatment. The reading may be a visual reading, an audible sound or any other suitable indicator.

Rather than obtaining the blood sample by a finger prick or the like, it is contemplated that a catheter 804 (FIG. 27) or the like may be inserted into a vein of the user and attached to the sample collector port 32. This may allow the system to automatically collect a blood sample from the user whenever a reading is desired. Alternatively, it is contemplated that the miniaturized portable cytometer may be implanted in the user, with the sample collector port 32 connected to a suitable blood supply.

Figure 16:
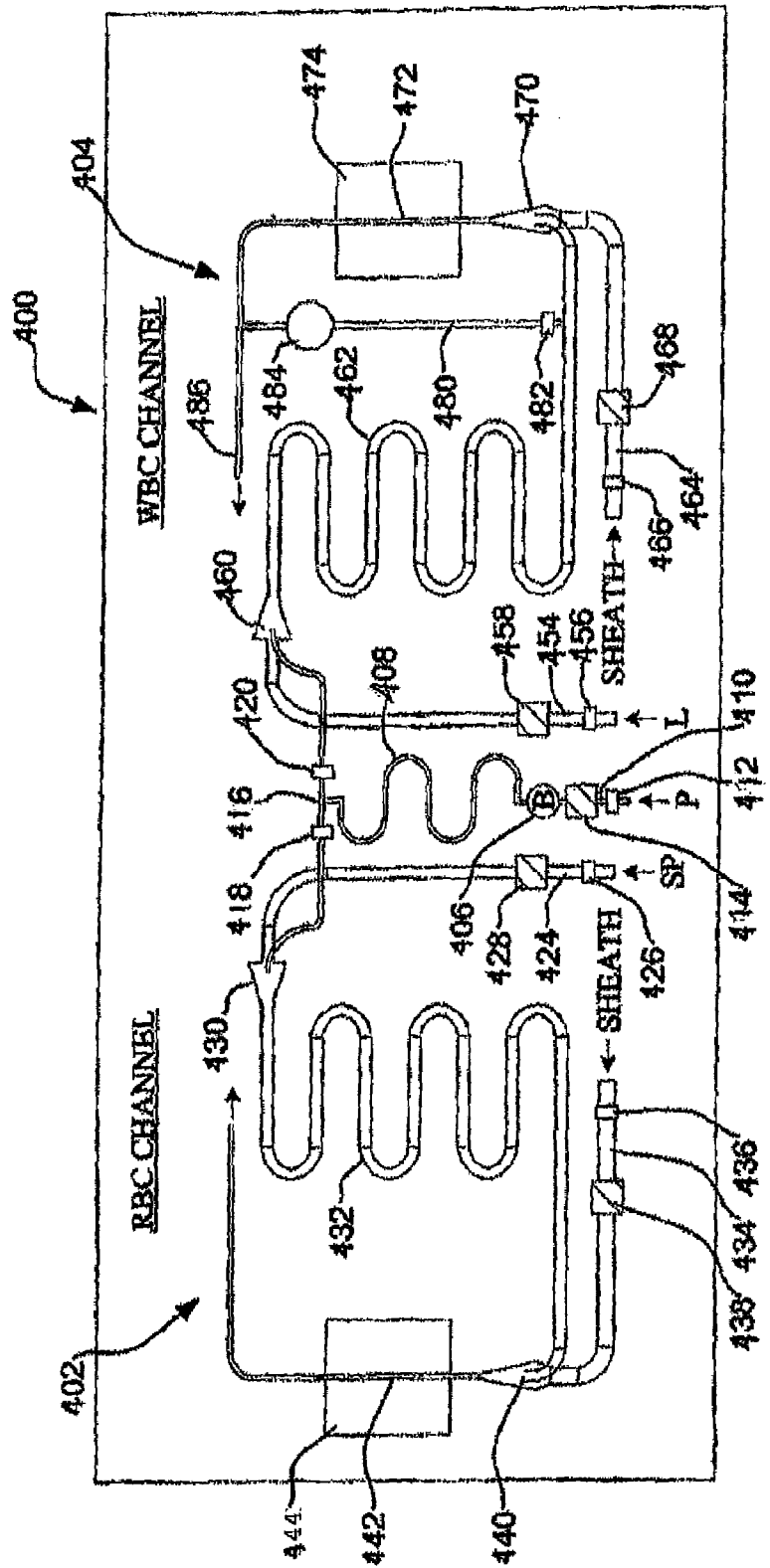
FIG. 16 is a schematic view of certain features of an illustrative cartridge.

FIG. 16 is a schematic view of certain features of an illustrative removable cartridge. The illustrative removable cartridge is generally shown at 400, and may be similar to removable cartridge 14 described herein. It should be understood that the removable cartridge 400 is only illustrative, and that the present example can be applied to many microfluidic cartridges, regardless of form, function or configuration. For example, the present example may be applied to removable cartridges adapted for flow cytometry, hematology, immunoassays, clinical chemistry, blood chemistry analysis, urinalysis, blood gas analysis, virus analysis, bacteria analysis, electrolyte measurements, and so on. It is also contemplated that the removable cartridges of the present system, such as removable cartridge 400, may be made from any suitable material or material system including, for example, glass, silicon, one or more polymers, or any other suitable material or material system, or combination of materials or material systems.

The illustrative removable cartridge 400 includes a first measurement channel 402 and a second measurement channel 404, although more or less measurement channels may be used, as desired. The first measurement channel 402, in the illustrative example, is a red blood cell measurement channel, and the second measurement channel 404 is a white blood cell measurement channel. A whole blood sample is received by the removable cartridge 400 via blood receiving port 406, which through capillary action, draws in a known amount of blood into an anti-coagulant coated blood sample storage capillary 408. A sample push (P) pressure is provided to a sample push fluid reservoir. When pressure is applied, the sample push fluid is forced from the sample push fluid reservoir into a blood sample push channel 410.

In some illustrative examples, a valve 412 and a flow sensor 414 may be provided in line with the blood sample push channel 410. The valve 412 may be controlled to open when it is desirable to push the blood sample through the fluidic circuit. The flow sensor 414 may measure the flow rate of the blood sample push fluid, and thus the blood sample flow rate through the anti-coagulant coated capillary 408. The flow rate provided by the flow sensor 414 may be used to help control the sample push (P) pressure that is provided to the removable cartridge 400.

In the illustrative example, the whole blood sample is partitioned and provided to the red blood cell measurement channel 402 and the white blood cell measurement channel 404 via branch 416. In the illustrative example, a valve 418 is provided in line with the branch to control the blood sample flow into the red blood cell measurement channel 402, and a valve 420 is provided to control the blood sample flow into the white blood cell measurement channel 404.

Turning specifically to the red blood cell measurement channel 402, a red blood cell sphering reagent pressure (SP) is provided to a sphering reagent reservoir. When pressure is applied, the sphering reagent in the sphering reservoir is forced into a sphering reagent channel 424.

In some illustrative examples, a valve 426 and a flow sensor 428 may also be provided in line with the sphering reagent channel 424. The valve 426 may be controlled to open when it is desirable to push the sphering reagent into the fluidic circuit. The flow sensor 428 may measure the flow rate of the sphering reagent, and provide a measure of the sphering reagent flow rate through the sphering reagent channel 424. The flow rate provided by the flow sensor 428 may be used to help control the sphering pressure (SP) that is provided to the removable cartridge 400 by the pressure source/controller.

During normal functional operation of the illustrative removable cartridge 400, the sphering reagent is pushed into an intersecting region 430 at a sphering reagent flow rate, and the blood sample is pushed into the intersecting region 430 at a blood sample flow rate. The blood sample flow rate and the sphering reagent flow rate may be controlled by a pressure source/controller.

The intersection region 430 may be configured so that the sphering reagent flows circumferentially around the blood sample when both fluids are flowing through the intersection region 430. In some cases, the sphering reagent flow rate may be higher than the blood sample flow rate, which may help improve the flow characteristics in a downstream sphering-on-the-fly channel 432, and in some cases, to help form a thin ribbon of blood that is completely and uniformly surrounded by the sphering reagent. Such a ribbon flow may help the sphering reagent uniformly sphere the red blood cells as they travel through the sphering-on-the-fly channel 432. Furthermore, the length of the sphering-on-the-fly channel 432, in conjunction with the flow rate of the sphering reagent and blood sample, may be set such that the blood sample is exposed to the sphering reagent for an appropriate amount of time.

A sheath fluid (SH) pressure may be provided to a sheath fluid reservoir. When pressure is applied, the sheath fluid is forced from the sheath fluid reservoir into a sheath channel 434. In some illustrative examples, a valve 436 and a flow sensor 438 may be provided in line with a sheath channel 434. The valve 436 may be controlled to open when it is desirable to push the sheath fluid into the fluidic circuit. The flow sensor 438 may measure the flow rate of the sheath fluid, and may provide a measure of the sheath flow rate through the sheath channel 434. The flow rate provided by the flow sensor 438 may be used to help control the sheath pressure (SH) that is provided to the removable cartridge 400.

In the illustrative example, the sheath fluid is provided to an intersecting region 440 at a sheath fluid flow rate, and the sphered blood sample is provided to the intersection region 440 at a sphered blood sample flow rate. The sphered blood sample flow rate and the sheath flow rate may be controlled by a pressure source/controller.

The intersection region 440 may be configured so that the sheath fluid flows circumferentially around the sphered blood sample when both fluids are flowing through the intersection region 440. In some cases, the sheath flow rate is significantly higher than the sphered blood sample flow rate, which may help improve core formation in a downstream flow cytometry channel 442. For example, in some flow cytometry applications, the intersecting region 440 may be configured to hydrodynamically focus and arrange the sphered blood cells in a single file core so that each red blood cell can be individually optically interrogated by an analyzer as they pass through an optical window region 444 in the removable cartridge 400. In some cases, the fluid that passes through the cytometry channel 442 is directed to an on-board waste reservoir.

Turning now to the white blood cell measurement channel 404, a white blood cell lysing reagent pressure (L) may be provided to a lysing reagent reservoir. When pressure is applied, the lysing reagent in the lyse reservoir is forced into a lysing reagent channel 454.

In some illustrative examples, a valve 456 and a flow sensor 458 may be provided in line with the lysing reagent channel 454. The valve 456 may be controlled to open when it is desirable to push the lysing reagent into the fluidic circuit. The flow sensor 458 may measure the flow rate of the lysing reagent, and provide a measure of the lysing reagent flow rate through the lysing reagent channel 454. The flow rate provided by the flow sensor 458 may be used to help control the lysing pressure (L) that is provided to the removable cartridge 400 by the pressure source/controller.

During normal functional operation of the illustrative removable cartridge 400, the lysing reagent is provided to an intersecting region 460 at a lysing reagent flow rate, and the blood sample is provided to the intersecting region 460 at a blood sample flow rate. The blood sample flow rate and the lysing reagent flow rate may be controlled by a pressure source/controller.

The intersection region 460 may be configured so that the lysing reagent flows circumferentially around the blood sample when both fluids are flowing through the intersection region 460. In some cases, the lysing reagent flow rate may be higher than the blood sample flow rate, which may help improve the flow characteristics in a lysing-on-the-fly channel 462, and in some cases, to help form a thin ribbon of blood that is completely and uniformly surrounded by the lysing reagent; Such a ribbon flow may help the lysing reagent uniformly lyse the red blood cells as they travel through the lysing-on-the-fly channel 462. Furthermore, the length of the lysing-on-the-fly channel 462, in conjunction with the flow rate of the lysing reagent and blood sample, may be set such that the blood sample is exposed to the lysing reagent for an appropriate amount of time.

A sheath fluid (SH) pressure may be provided to a sheath fluid reservoir. When pressure is applied, the sheath fluid is forced from the sheath fluid reservoir into a sheath channel 464. In some illustrative examples, a valve 466 and a flow sensor 468 may be provided in line with a sheath channel 464. The valve 466 may be controlled to open when it is desirable to push the sheath fluid into the fluidic circuit. The flow sensor 468 may measure the flow rate of the sheath fluid, and may provide a measure of the sheath flow rate through the sheath channel 464. The flow rate provided by the flow sensor 468 may be used to help control the sheath pressure (SH) that is provided to the removable cartridge 400. In some cases, the sheath flow rate through sheath channel 464 is the same as the sheath flow rate through sheath channel 434. However, in other cases, the sheath flow rate through sheath channel 464 may be different from the sheath flow rate through sheath channel 434.

In the illustrative example, the sheath fluid is provided to an intersecting region 470 at a sheath fluid flow rate, and the lysed blood sample is provided to the intersecting region 470 at a lysed blood sample flow rate. The lysed blood sample flow rate and the sheath flow rate may be controlled by a pressure source/controller.

The intersection region 470 may be configured so that the sheath fluid flows circumferentially around the lysed blood sample when both fluids are flowing through the intersection region 470. In some cases, the sheath flow rate is significantly higher than the lysed blood sample flow rate, which may help improve core formation in a downstream flow cytometry channel 472. For example, in some flow cytometry applications, the intersecting region 470 may be configured to hydrodynamically focus and arrange the white blood cells in the lysed blood sample in a single file core so that each white blood cell can be individually optically interrogated by an analyzer as they pass through an optical window region 474 in the removable cartridge 400. In some cases, the fluid that passes through the cytometry channel 472 is provided to an on-board waste reservoir.

In some cases, an absorption measurement channel may also be provided. In the illustrative example, a portion of the lysed blood sample is provided to absorption channel 480. A valve 482 may be provided to selectively allow a portion of the lysed blood sample to pass to the absorption channel or region 484. The analyzer may include a light source to illuminate the absorption channel or region 484, as well as a detector to detect the light that is not absorbed by the lysed blood sample in the absorption channel or region 484. The analyzer may then determine an absorption level, from which a bulk absorption based hemoglobin measurement can be made. In some cases, the absorption channel 484 may be situated downstream of the cytometry channel 472, if desired. In other cases, a whole blood sample may be provided directly, such as from branch 416, to an absorption channel. In such cases, the absorption channel may include a mechanism to lyse the red blood cells prior to taking the absorption measurement. While the illustrative removable cartridge 400 is adapted to perform a complete blood count (CBC) analysis on a whole blood sample, it is contemplated that other removable cartridge configurations and analysis types may be used, as desired.

Figure 17:
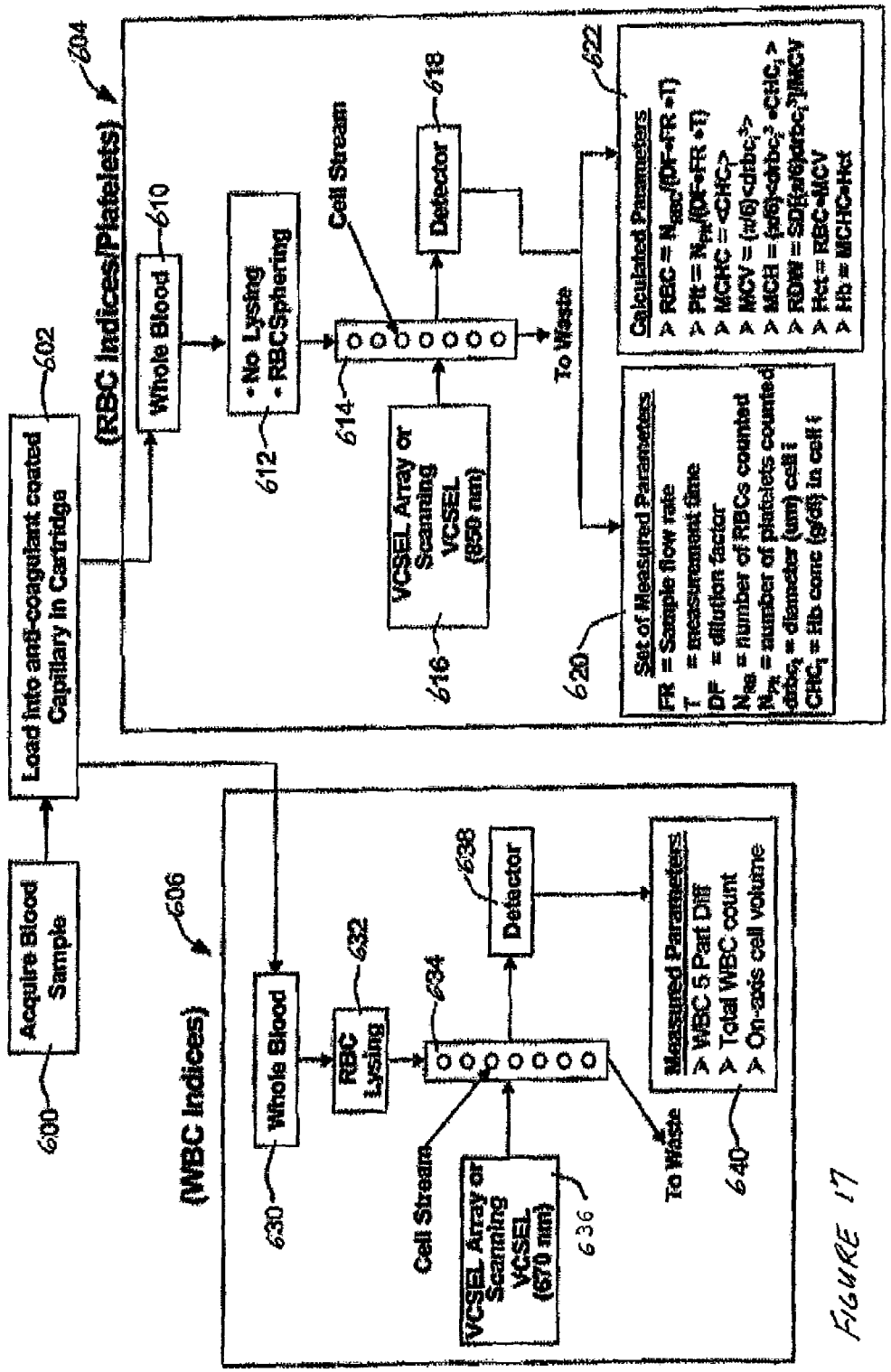
FIG. 17 is a schematic flow diagram showing an illustrative approach for analyzing a blood sample.

FIG. 17 is a schematic flow diagram showing an illustrative approach for analyzing a blood sample using a removable cartridge. In the illustrative approach, a blood sample is first acquired at step 600. Next, the blood sample is provided to an anti-coagulant coated capillary in a removable cartridge. The blood sample is then partitioned and provided to a red blood cell and platelet (RBC/P) measurement channel 604 and a white blood cell (WBC) measurement channel 606.

In the RBC/P measurement channel 604, the red blood cells are first sphered as shown at 612, and then hydrodynamically focused and provided single file down a RBC/P cytometry channel 614 in the removable cartridge. A light source 616, such as a vertical cavity surface emitting laser (VCSEL), shines light on the individual cells as they pass by an analysis region of the RBC/P cytometry channel 614. In some cases, an array of VCSEL devices is provided, and only the VCSEL(s) that is/are aligned with the individual cells as they pass by the analysis region of the RBC/P cytometry channel 614 is activated. Some of the incident light provided by the VCSEL is scattered, and a detector 618 detects the scattered light. In some cases, the detector 618 may detect forward angle scatter light (FALS), small angle scatter Light (SALS) and large angle scatter light (LALS).

In some cases, a laser (or other) source is focused into the RBC/P cytometer channel 614, either as an elongated line source or as two separate spot sources. The RBC and platelets in the RBC/P cytometer channel 614 through the focused light. High quality collection optics may be used to form a sharp image of the cells and focused illumination onto an opaque screen containing one, two or more parallel slits whose longitudinal axes are arranged orthogonal to the flow direction in the RBC/P cytometer channel 614. The distance between the slits may be, for example, on the order of the mean cell separation expected in the RBC/P cytometer channel 614. The opaque screen containing the slits may be placed in front of one or more detectors 618. As the image of a cell passes over a slit, it obscures the light incident on the slit and causes a reduction in the signal on the detector 618, producing a pulse waveform whose width is proportional to the cell diameter. When two spaced slits are provided, the two waveforms may permit the calculation of the cell flow velocity, and hence the cell size. High signal-to-noise may be obtained using this technique, which permits easy counting of events and identification of multiple cell events. Pulse width and amplitude may further enable the discrimination of some cell types.

In some cases, an image of both the cell and the light source is imaged on a double slit aperture placed in front of the detector 618. The double slit aperture provides a well defined geometrical aperture and high signal-to-noise ratio to count cells. As discussed above, signals from the slits may permit the accurate measurement of cell flow velocity, which in turn may permit the calculation of cell diameter.

In some cases, and as shown at 620, a number of parameters may be measured during this analysis, including for example, sample flow rate (FR), measurement time (T) duration, and sample dilution factor (DF). By monitoring the output of the detector(s), and/or the corresponding scatter signature, the number of red blood cells ($N_{RB}$), the number of platelets ($N_{Plt}$), the diameter of each cell (drbc) and the hemoglobin concentration of each cell may be measured.

From these parameters, and as shown at 682, a number of red blood cell analysis parameters may be calculated including, for example, a red blood cell count (RBC=$N_{RB}$/(DF×FR×T)), a platelet count (Plt=$N_{Plt}$/(DF×FR×T)), a mean cell hemoglobin concentration (MCHC=<CHC>), a mean cell volume (MCV=$(\pi/6) \times <drbc^3>$), a mean cell hemoglobin content (MCH=$(\pi/6) \times <drbc^3 \times CHC>$), a relative distribution width (RDW=Standard Deviation of $[(\pi/6) \times drbc^3]$/MCV), a Hematocrit parameter (Hct=RBC×MCV) and/or a hemoglobin concentration (Hb=MCHC×Hct).

In the illustrative WBC measurement channel 606, the red blood cells are first lysed as shown at 632, and then hydrodynamically focused and provided single file down a WBC cytometry channel 634 in the removable cartridge. A light source 636, such as a vertical cavity surface emitting laser (VCSEL), shines light on the individual cells as they pass by an analysis region of the WBC cytometry channel 634. In some cases, an array of VCSEL devices is provided, and only the VCSEL(s) that is/are aligned with the individual cells as they pass by the analysis region of the WBC cytometry channel 634 is activated. Some of the incident light provided by the VCSEL is scattered, and a detector 638 detects the scattered light. In some cases, the detector 638 detects forward angle scatter light (FALS), small angle scatter light (SALS), and large angle scatter light (LALS). In some cases, and as shown at 640, a number of parameters may be measured during the analysis including, for example, on-axis cell volume, total WBC count, and WBC five (5) part differentiation.

Figure 18:
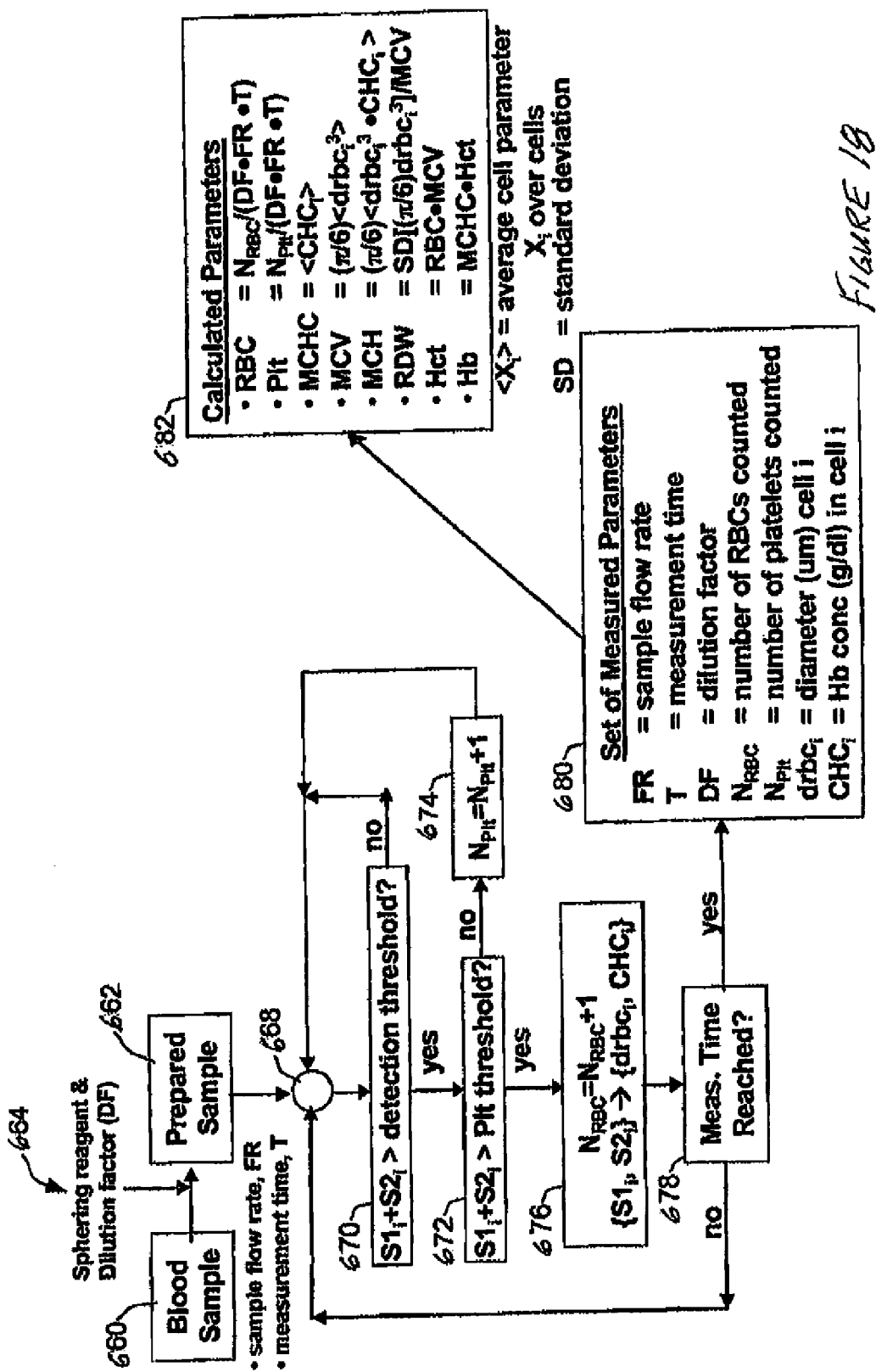
FIG. 18 is a flow diagram showing an illustrative approach for obtaining a number of red blood cell parameters.

FIG. 18 is a flow diagram showing an illustrative approach for obtaining a number of red blood cell parameters. In the illustrative approach, a blood sample is acquired at step 660. Next, the blood sample is diluted to a desired Dilution Factor (DF), and sphered as shown at 664. The diluted and sphered blood cells are then hydrodynamically focused and provided single file down a RBC/P cytometry channel in the removable cartridge. A light source 616, such as a vertical cavity surface emitting laser (VCSEL), shines light on the individual cells as they pass by an analysis region of the RBC/P cytometry channel. Some of the incident light provided by the VCSEL(s) is scattered, and a detector may be used to detect the scattered light. In some cases, the detector detects both forward angle scattered light (FALS) and small angle scattered light (SALS) for each cell. A processor or the like may then map the two independent scatter parameters, namely SALS and FALS, for each cell to a cell diameter parameter and a cell hemoglobin concentration parameter as follows:

$\{S_{SALSi}, S_{FALSi}\} \rightarrow \{drbc_i, CHC_i\}$

As shown at 670, if the intensity of the scatter $S_{SALSi}$ plus $S_{FALSi}$ is not greater than a predetermined detection threshold, control is passed back to step 668. However, if the intensity of the scatter $S_{SALSi}$ plus $S_{FALSi}$ is greater than a predetermined detection threshold, control is passed to step 672. Step 672 determines if the sum of $S_{SALSi}$ and $S_{FALSi}$ is greater than a predetermined platelet threshold. If the sum of $S_{SALSi}$ and $S_{FALSi}$ is not greater than the predetermined platelet threshold, it is determined that the particle "i" is a platelet, and control is passed to step 674. Step 674 increments the number of counted platelets ($N_{Plt}$) by one, and passes control back to step 668.

If the sum of $S_{SALSi}$ and $S_{FALSi}$ is greater than a predetermined platelet threshold, the cell is a red blood cell, and control is passed to step 676. Step 676 increments the number of counted red blood cells ($N_{RBC}$) by one, and passes control to step 678. Step 678 determines if a predetermined measurement time has been reached. If not, control is passed back to step 668.

Once the measurement time is reached at step 678, control is passed to step 680. Step 680 shows a number of measured parameters including, for example, sample flow rate (FR), measurement time (T) duration, sample dilution factor (DF), number of red blood cells counted ($N_{RBC}$), number of platelets counted ($N_{Plt}$), the diameter of each cell ($drbc_i$) and hemoglobin concentration of each cell ($CHC_i$). From these parameters, and as shown at step 682, a number of blood cell analysis parameters may be calculated including, for example, a red blood cell count (RBC=$N_{RBC}$/(DF×FR×T)), a platelet count (Plt=$N_{Plt}$/(DF×FR×T)), a mean cell hemoglobin concentration (MCHC=<$CHC_i$>, a mean cell volume (MCV=$(\pi/6) \times <drbc_i^3>$), a mean cell hemoglobin content (MCH=$(\pi/6) \times <drbc_i^3 \times CHC_i>$), a relative distribution width (RDW=Standard Deviation of $[(\pi/6) \times drbc_i^3]$/MCV), a Hematocrit parameter (Hct=RBC×MCV) and/or a hemoglobin concentration (Hb=MCHC×Hct), wherein the notation <$X_i$> means the average cell parameter over all cells $X_i$.

Figure 19:
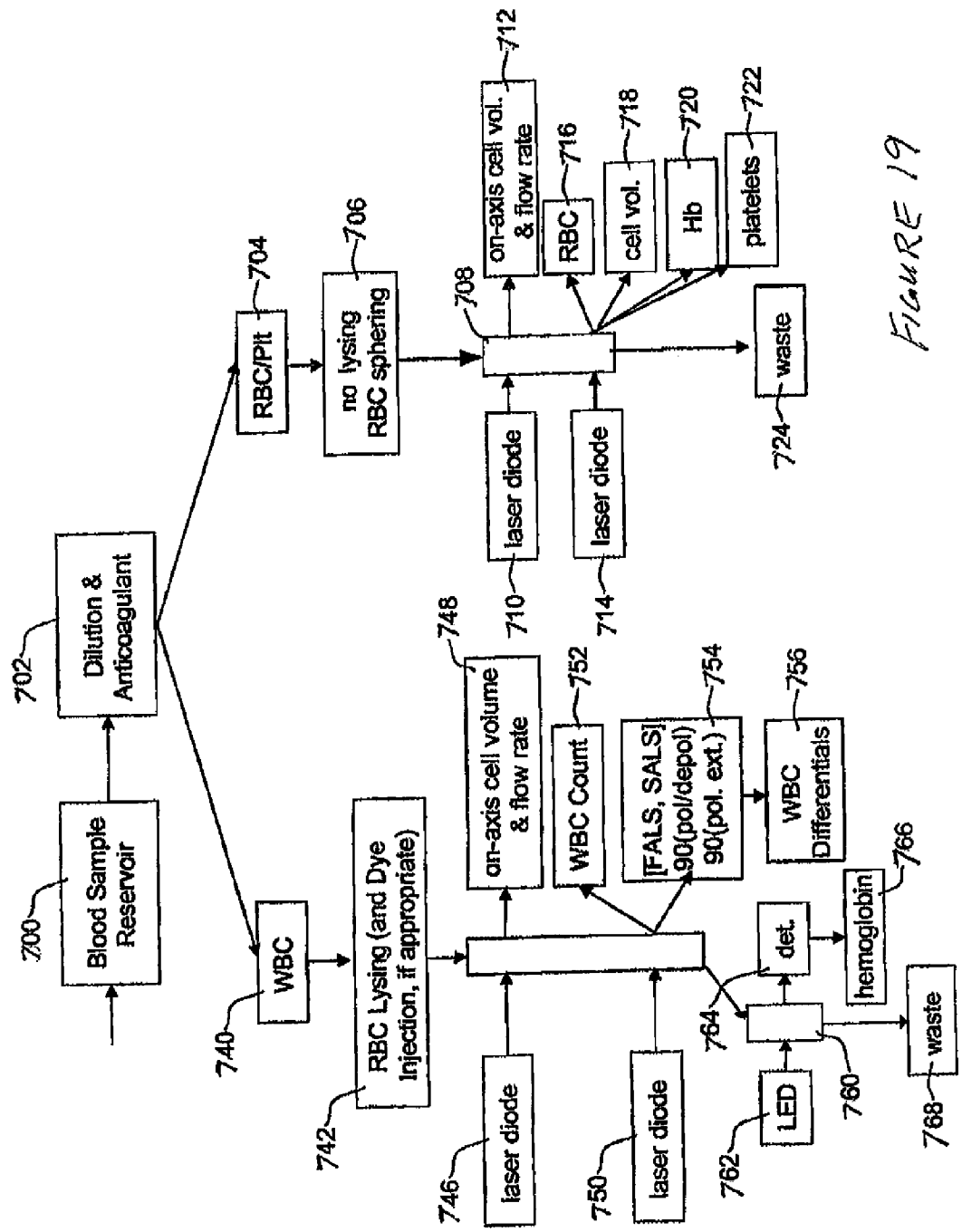
FIG. 19 is a schematic flow diagram showing another illustrative approach for analyzing a blood sample.

FIG. 19 is a schematic flow diagram showing another illustrative approach for analyzing a blood sample. In this illustrative approach, a blood sample is acquired, and provided to a blood sample reservoir, as shown at step 700. Next, the blood sample is provided to an anti-coagulant coated capillary in a removable cartridge, and diluted. The blood sample is then partitioned and provided to a red blood cell and platelet (RBC/P) measurement channel 704 and a white blood cell (WBC) measurement channel 740.

In the RBC/P measurement channel 704, the red blood cells are first sphered as shown at 706, and then hydrodynamically focused and provided single file down a RBC/P cytometry channel 708 in the removable cartridge. A first light source 710, such as a vertical cavity surface emitting laser (VCSEL) and associated optics, provides a focused light beam on the individual cells as they pass by an analysis region of the RBC/P cytometry channel 708; In some cases, an array of VCSEL devices is provided, and only the VCSEL(s) that is/are aligned with the individual cells as they pass by an analysis region of the RBC/P cytometry channel 708 is/are activated.

As the individual cells/particles pass through the focused incident light beam, some of the light is blocked, scattered or otherwise obstructed, which can be detected by a detector (not shown). When two or more light sources are focused on different spaced spots along the RBC/P cytometry channel 708, the leading and/or trailing edge of each cell can be detected. By measuring the time it takes for a cell to traverse the distance from one focused spot to the next, the flow rate and thus the cell velocity can be determined. With the cell velocity determined, the length of time that a cell blocks, scatters or otherwise obstructs the light beam can be correlated to cell size and/or cell volume.

In some examples, another light source 714 and associated optics may be provided by an analyzer. The associated optics of light source 714 may collimate the light, and measure off-axis scatter, such as SALS and FALS scatter. As noted above, the SALS and FALS scatter can be used to measure, for example, a number of red blood cells counted ($N_{RBC}$) 716, number of platelets counted ($N_{Plt}$) 722, the diameter of each cell ($drbc_i$), the cell volume 718, and hemoglobin concentration 720 of each cell ($CHC_i$). From these parameters, and as discussed above, a number of blood cell analysis parameters may be calculated including, for example, a red blood cell count (RBC=$N_{RBC}$/(DF×FR×T)), a platelet count (Plt=$N_{Plt}$/(DF×FR×T)), a mean cell hemoglobin concentration (MCHC=$<CHC_i>$), a mean cell volume (MCV=$(\pi/6)\times<drbc_i^3>$), a mean cell hemoglobin content (MCH=$(\pi/6)\times<drbc_i^3\times CHC_i>$), a relative distribution width (RDW=Standard Deviation of $[(\pi/6)\times drbc_i^3]$/MCV), a Hematocrit parameter (Hct=RBC×MCV) and/or a hemoglobin concentration (Hb=MCHC×Hct), wherein the notation $<X_i>$ means the average cell parameter over all cells $X_i$.

In the illustrative WBC measurement channel 740, the red blood cells are lysed, and dye is injected as appropriate, as shown at 742. The cells are then hydrodynamically focused and provided single file down a WBC cytometry channel 744 in the removable cartridge. A light source 746, such as a vertical cavity surface emitting laser (VCSEL), shines light on the individual cells as they pass by an analysis region of the WBC cytometry channel 744. In some cases, an array of VCSEL devices is provided, and only the VCSEL(s) that is/are aligned with the individual cells as they pass by the analysis region of the WBC cytometry channel 744 is activated.

As the individual cells/particles pass through the focused incident light beam, some of the light is blocked, scattered or otherwise obstructed which may be spotted by a detector (not shown). When two or more light sources are focused on different spaced spots along the WBC cytometry channel 744, the leading and/or trailing edge of each cell can be detected. By measuring the time it takes for a cell to traverse the distance from one focused spot to the next, the flow rate and thus the cell velocity can be determined. With the cell velocity determined, the length of time that a cell blocks, scatters or otherwise obstructs the light beam can be correlated to cell size and/or cell volume.

In some examples, a light source 750 and associated optics and/or polarizers may be provided. The associated optics of light source 750 may collimate the light, and measure off-axis scatter, such as SALS, FALS and LALS scatter, as shown at 754. Like above, the SALS, FALS and LALS scatter can be used to measure, for example, the number of white blood cells counted ($N_{WBC}$) 752, as well as to help with white blood cell differentiation, as shown at 756. In some cases, one or more polarizers is/are provided to polarize the light provided by the light source, and the level of polarization extinction/rotation detected at the detector may be used to help perform white blood cell differentiation, but this is not required in all examples.

A separate module may be used for determining an amount of hemoglobin (Hb) or hemoglobin concentration in the blood sample. The module may use hemoglobin absorption to determine the Hb. The amount of hemoglobin in the blood may be expressed in grams per liter or other unit combinations. In an illustrative example, the cells that exit the WBC cytometry channel 744 may be provided to a bulk absorption channel 760. A light source 762 may shine light onto the cells present in the absorption channel 760, and a detector 764 may detect the light that is not absorbed by the resident cells. The absorption channel 760 may thus be used to measure the bulk absorption level of the resident cells. The absorption level may provide, for example, a measure of the bulk or mean cell hemoglobin concentration in the blood sample. The hemoglobin channel may have re-zeroing optics and auto focus and/or alignment. Light source 762 may be a LED having an output close to the center of the absorption peak, thus possibly making a filter unnecessary. There may be a curvette for receiving and holding a sample to be evaluated in terms of hemoglobin.

Figure 20:
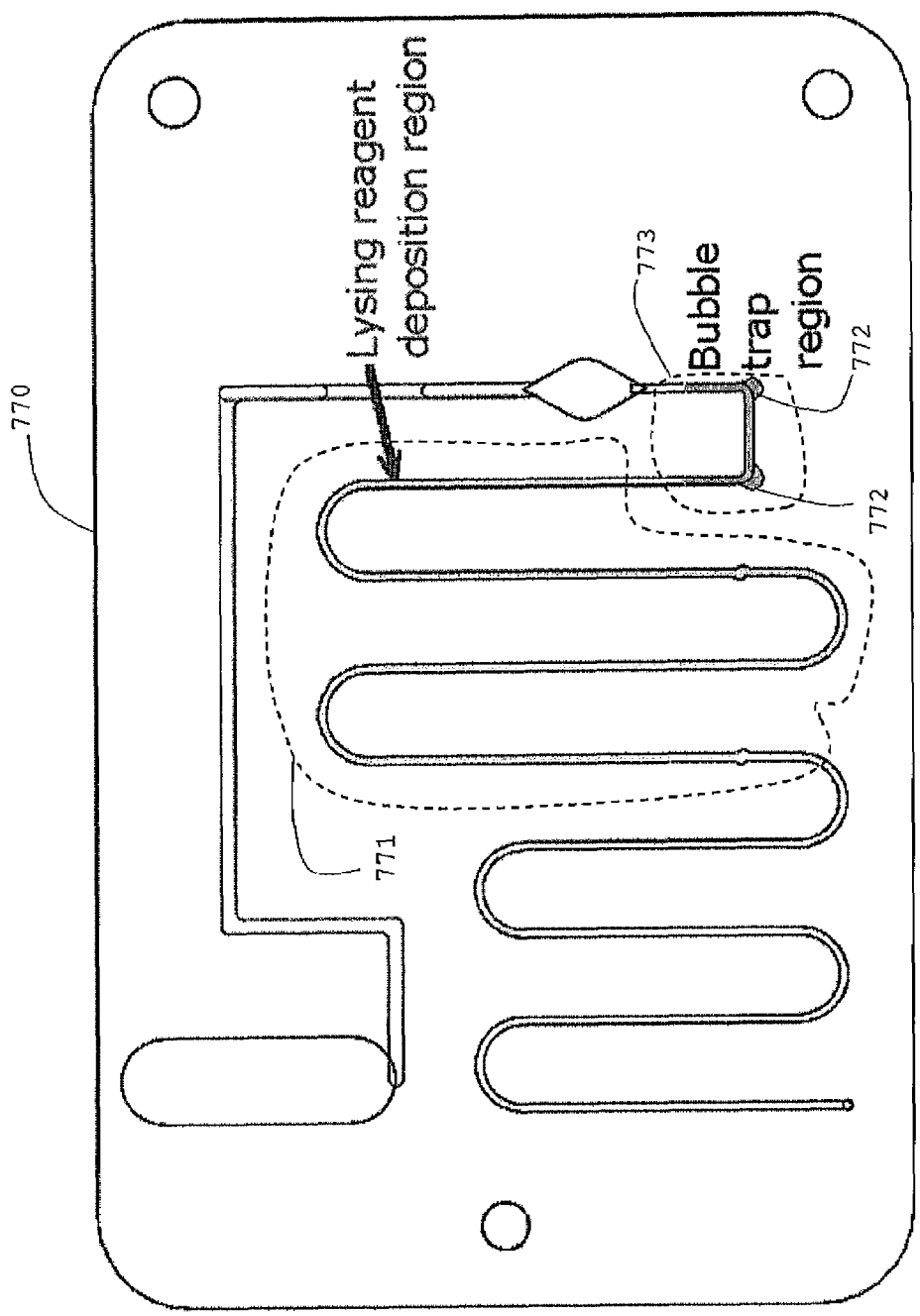
FIG. 20 shows a card having a lysing reagent deposition region and a bubble trap so as to improve hemoglobin measurement accuracy.

FIG. 20 shows an example of an HGB card 770 or module. There may be a lysing reagent deposition region 771 showing where there is a deposition/printing of the dry lysing powder. There may be a budged corner 772 at the very last turns in a region 773 showing a bubble trap arrangement to eliminate air bubbles generated during blood lysing by the dry lysing powder so as to improve the HGB measurement accuracy.

Figures 21, 22:
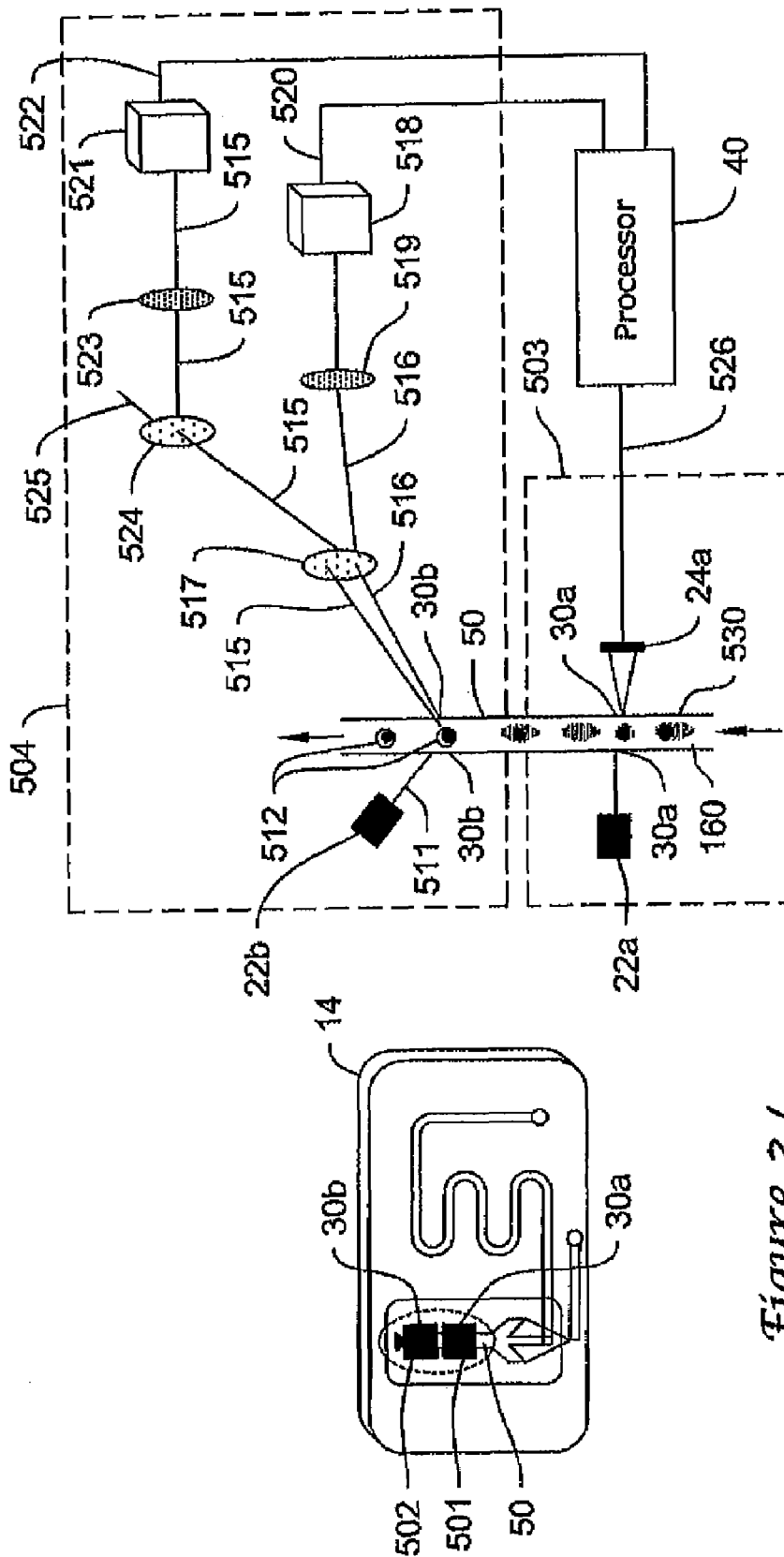
FIG. 21 is a diagram of a cytometer cartridge with a scattering subsystem and a fluorescent optical subsystem.
FIG. 22 is a schematic of the optical arrangement of the scattering and fluorescent subsystems.

FIG. 21 shows a cytometer cartridge 500 showing a scattering optical subsystem 501 and fluorescent optical subsystem 502. Optical subsystem 501 may include windows or openings 30a on each side of flow channel 530 and optical subsystem 502 may include windows or openings 30b. In each subsystem, there may be a window or opening on each side of flow channel 530. The openings may have optical inserts or lenses. This cytometer may be implemented for wearing, attachment on, or insertion in a person's body FIG. 22 shows systems 503 and 504 which may incorporate optical subsystems 501 and 502, respectively. System 503 may also include VCSEL array 22a and detector array 24a for scattering measurements of particles, such as white blood cells, in core stream 160. This system is may be used for the counting and classification of lymphocytes and neutrophils. Self-alignment is may be enabled by a red VCSEL-array based optical subsystem. Illustrative examples of scattering system 503 are described herein.

System 504 may be a fluorescent exciting and detection mechanism used for identifying and counting specific subclasses of white blood cells and blood-based proteins. The detection of subclasses of white blood cells may be enabled by the availability of suitable antibodies, many of which are commercially available in a fluorescently conjugated form. FIG. 23 shows an outline sketch of blood composition and the cells that may be subject to counting and identification by fluorescent system 504. The red blood cells may be removed form the sample to be looked with the cytometer by lysing as noted herein. The platelets may be kept as the small size does not affect the results of the cytometer when checking the white blood cells. For an illustrative example, the CD4-positive T-cells 505, shown in the structure of FIG. 23, have proportions and counts in blood that may be very important in following a clinical course of an HIV infection. An antibody with a marker added that associates with CD4 may be mixed in the sample of blood to get a resultant "Y"-looking structure of the antibody (AB) 506 and its marker (M) 507, attached to CD4 cell 505, as shown in FIG. 24a. Light source 22b may emit light which may be absorbed by marker 507. In response, marker 507 may fluoresce and emit light of a particular wavelength which may be detected to identify CD4 cell 505.

Checking blood for anthrax may be another application of the present cytometer. Antibodies 508 for the anthrax-causing bacteria 509 may be mixed with the blood sample. The antibodies may associate with bacteria 509. The antibodies may have markers 510 that fluoresce upon impingement of light. The "Y" structure of antibody 508 is shown in FIG. 24b. Markers 510 emit a light of a particular bandwidth which may be different from the bandwidth of marker 507 of antibody 506 for CD4 cell 505. So the anthrax problem may be identified separately from the HIV problem in the same blood sample test by the fluorescent emissions having different wavelengths, colors or signatures. The number of different problems being detected at the same time in the same blood sample may be many more than two.

For another illustrative example, Neupogen[R] (a type of protein) may be regarded for providing neutrophil counts in cancer patients undergoing myelosuppressive chemotherapy. While doing this therapy, there may a need to accurately monitor the white blood cell counts (specifically neutrophils, monocytes and platelet counts during the Neupogen[R] therapy period). The present cytometer may be used by untrained personnel to monitor such parameters of chemotherapy patients in their homes.

The miniaturized portable cytometer may also be used in biowarfare. It may be used for quantitative detection and identification of biowarfare agents. This detection and identification may be based antibody-antigen type immunoassay that may be implemented with fluorescent measurements. The environment, water and food may be monitored for any possible presence of biological agents. It may involve sample collection and preparation appropriated for the cytometer. Other applications of the cytometer may include high throughput analysis (using the fluorescent detection features) and sequencing of DNA and RNA, studying the response of cell to potential drugs, immunophenotyping of leukemia and lymphomas and monitoring residual disease in cancer patients, and cell sorting and cell isolation, including high-speed separation of rare event populations. Certain applications and uses may be accomplished with the single, portable, miniaturized, integrated scattering and multi-color fluorescent, low-power, low-cost cytometry instrument having a compact precision fluid driving system, not requiring operator intervention or adjustment during the analytical phase, not requiring trained personnel to operate the instrument, and using sanitary, disposable plastic- or other material-based microfluidic cartridges 14 having integrated optics and internal blood sample processing, among other features.

System 504 of FIG. 22 may have a laser light source 22b positioned to direct light 511 at particles 512 flowing single file through flow channel 530. For illustrative purposes, particles 512 may include structures 513 and 514 of FIGS. 24a and 24b, respectively. Light 511 may be from a red or a blue laser source, such as a light emitting diode (LED), which may have a bandwidth of, for example, 650 to 700 nanometers or 380 to 420 nanometers, respectively. Other types of sources having appropriate wavelengths may be used for light 511. As light 511 impinges fluorescent markers 507 and 510, these markers may fluoresce and emit light 515 and 516, respectively. Since the markers are different from each other, light 515 and light 516 may have different wavelengths. Thus, structures 513 and 514 not only may be identifiable by the wavelengths of their emitted light but can be differentiated form each other in the same sample, blood or otherwise. Light 515 and 516 may go to a dichroic beam splitter 517 which separates the two beams by directing each of them in different directions. Beam 516 may go to a fluorescence photo detector 518 for detection and conversion of light 516 into an electrical signal 520 to processor 40. Beam 515 may go to a fluorescence photo detector 521 for detection and conversion of light 515 into an electrical signal 522 to processor 40. Band pass filter 519, which is in the path of beam 516, may filter out light 511 from light source 22b that managed to be present in beam 516. Band pass filter 523 may serve the same purpose for beam 515 as filter 519 for beam 515. A mirror 524 may be used to redirect beam 515 for purposes of detector 521 location for the possibility of more compact packaging of detection system 504 or for other reasons. Mirror 524 may on the other hand be another dichroic beam splitter for splitting out light 525 of a wavelength different from that of beams 515 and 516. More splitters might be used in a cascade-like or other structure to split out light of still other frequencies. Also going to processor 40 is a signal from detector array 24a of scattering detection system 503. It may be noted that light sources 22a and 22b may be replaced with one light source.

Splitter 517 may be replaced with other mechanisms for separating out the light of various wavelengths or selecting certain wavelengths. They may include notch and step function filters of various kinds, tunable diffraction gratings, thin film dielectric stacks, mirror beam splitters, photonic band-gap filters, photonic crystals, tunable band pass filters, etalon comb and other structures, wafers having light guides with structural or other filtering, silicon or glass wafers having a waveguide and perforations of a specific size and pitch for absorbing/filtering, and so on.

Figure 25:
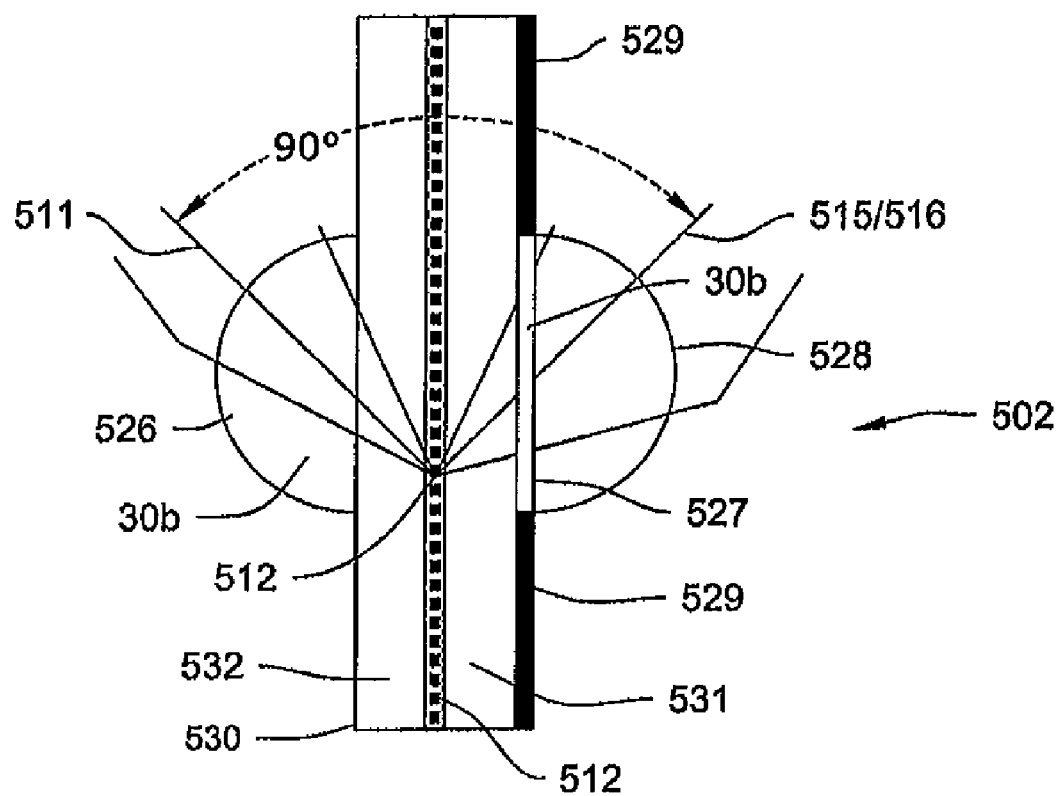
FIG. 25 is a diagram of a fluorescent optical subsystem at a flow channel.

FIG. 25 shows an illustrative example of the fluorescence optical subsystem 502. A beam 511 may be emitted by light source 22b and focused onto a particle 512 by a microlens 526 through window 30b. Light beam 511 may or may not be collimated. Particle 512 may have a marker that fluoresces and emits a light beam 515, 516 through window 30b, a thin film coating filter 527 and a microlens 528, respectively. Filter 527 may filter out light 511 from light source 22b. Filter 527 may be a dielectric stack situated under lens 528 and be a notch or step function filter to block source 22b light 511. Lens 528 may focus fluorescent light emitted from the marker into a beam 515/516 which may go on to a beam splitter such as splitter 517. Beam 515/516 may or may not be collimated. An opaque or absorptive layer 529 may be formed around or before and after window 30b or lens 528 on a glass, quartz or plastic (laminated or not) substrate 531 of flow channel 530. Layer 529 may block any light 511 emanating from light source 22b from exiting out with fluorescent light 515/516. Layer or blocking filter 529 may be a thin film that is black or opaque to the wavebands desired to be blocked. Filter 529 could be a notch or step function filter. The other glass, quartz or plastic (laminated or not) substrate 532 may form flow channel 530 for the core flow of particles 512. The material of substrates 531 and 532, windows 30b and lens 526 and 528 should not contain ingredients that may fluoresce. In one illustrative example, the direction of light 511 from source 22b may be about 90 degrees relative to the direction of fluorescent light 515/516 emitted from particle 512. This angle between source light 511 and emitted fluorescent light 515/516 may effectively reduce or eliminate source light emanating out with fluorescent light 515/516. The angle of the direction of light 511 from source 22b in the example may be about 45 degrees relative to the direction of the longitudinal dimension flow channel 530 or the direction of the core flow of particles 512. However, in some applications, the angle between the directions of light 511 and light 515/516 may be between 0 and 120 degrees.

Figure 26:
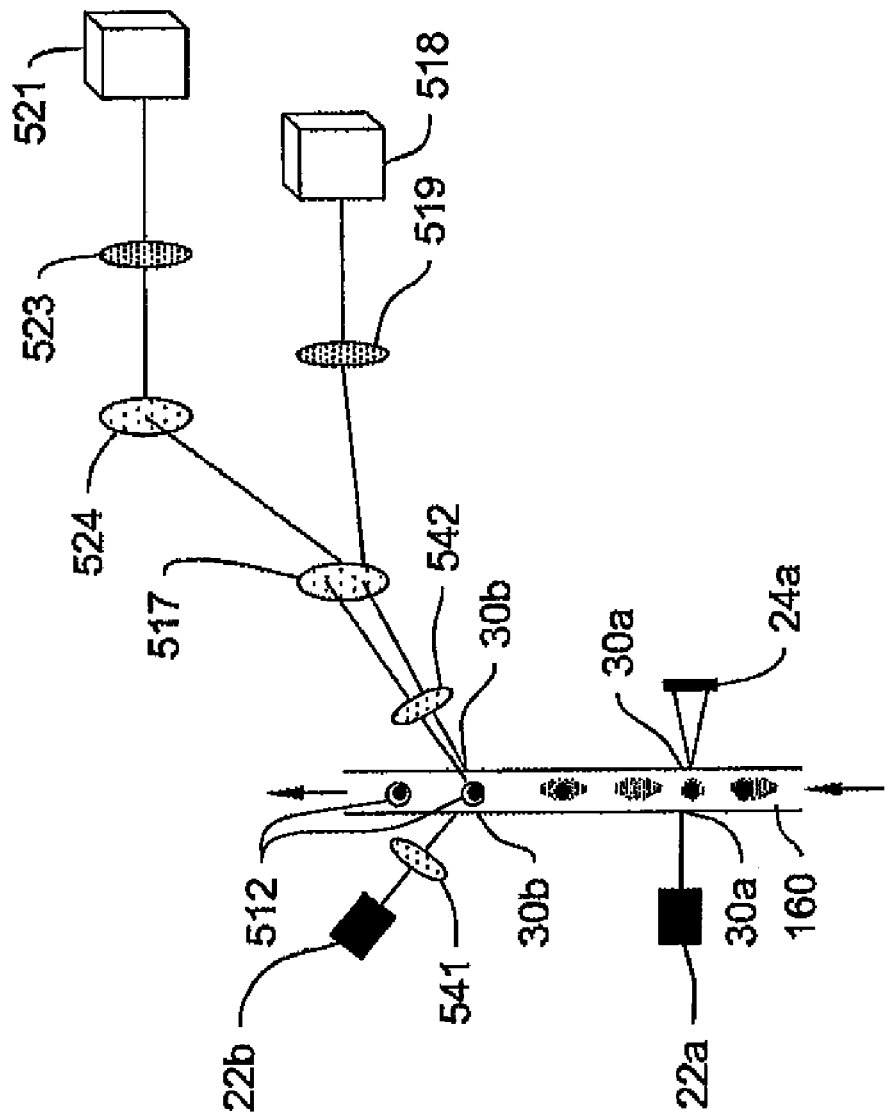
FIG. 26 is a schematic of a lens equipped fluorescent optical subsystem.

FIG. 26 shows a diagram of cytometer configuration of FIG. 22, but with the placement of lenses 541 and 542. As noted herein, windows and openings 30b may or may not have micro lenses in addition to lenses 541 and 542. A single light source version (in lieu of sources 22a and 22b) may also have a similar lens and/or micro lens optical arrangement.

Figure 27:
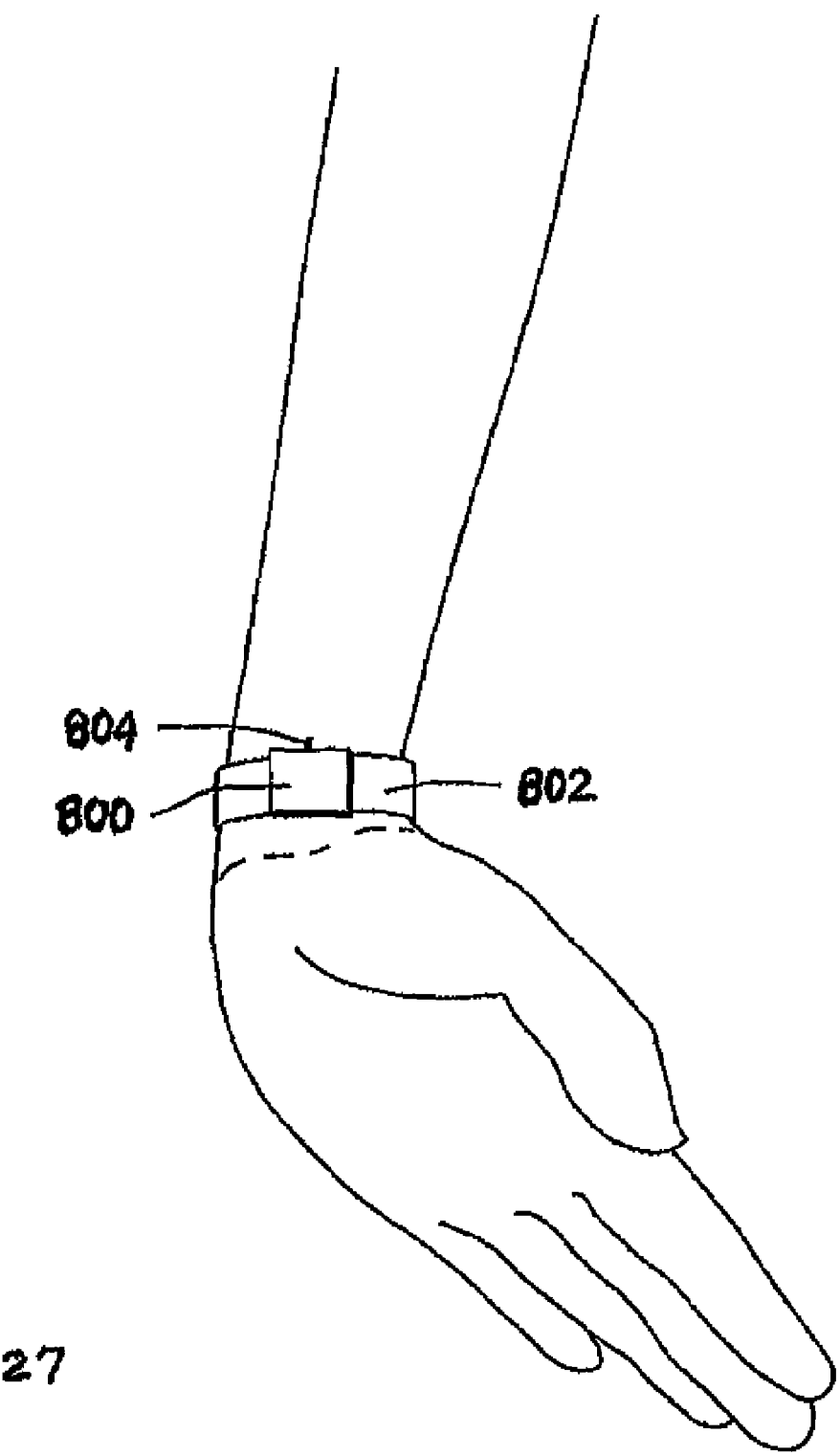
FIG. 27 shows a miniaturized cytometer for wearing on a wrist.

FIG. 27 is a perspective view of an illustrative example of a miniaturized portable cytometer having both scattering and fluorescent detection and monitoring adapted to be worn around the wrist or palm. This cytometer 800 may be similar to that shown in FIGS. 7, 21, 30, 31, 33 and/or 37. A band 802 may secure the miniaturized portable cytometer 800 to the wrist of a user.

As indicated herein, the user may obtain a removable cartridge and provide a blood sample to the sample collector port 32 (see FIGS. 7, 21, 22 and 26) of the removable cartridge. The blood sample may be collected by, for example, a finger prick. The user may then insert the removable cartridge into the housing, and manually pressurize the system. The miniaturized and portable cytometer may then provide a reading that indicates if the user should seek medical treatment. The reading may be a visual reading, an audible sound or any other suitable indicator.

Rather than obtaining the blood sample by a finger prick or the like, it is contemplated that a catheter 804 or the like may be inserted into a vein of the user and attached to sample collector port 32. This may allow the system to automatically collect a blood sample from the user whenever a reading is desired. Alternatively, it is contemplated that the miniaturized portable cytometer may be implanted in the user, with sample collector port 32 connected to a suitable blood supply.

Figure 28:
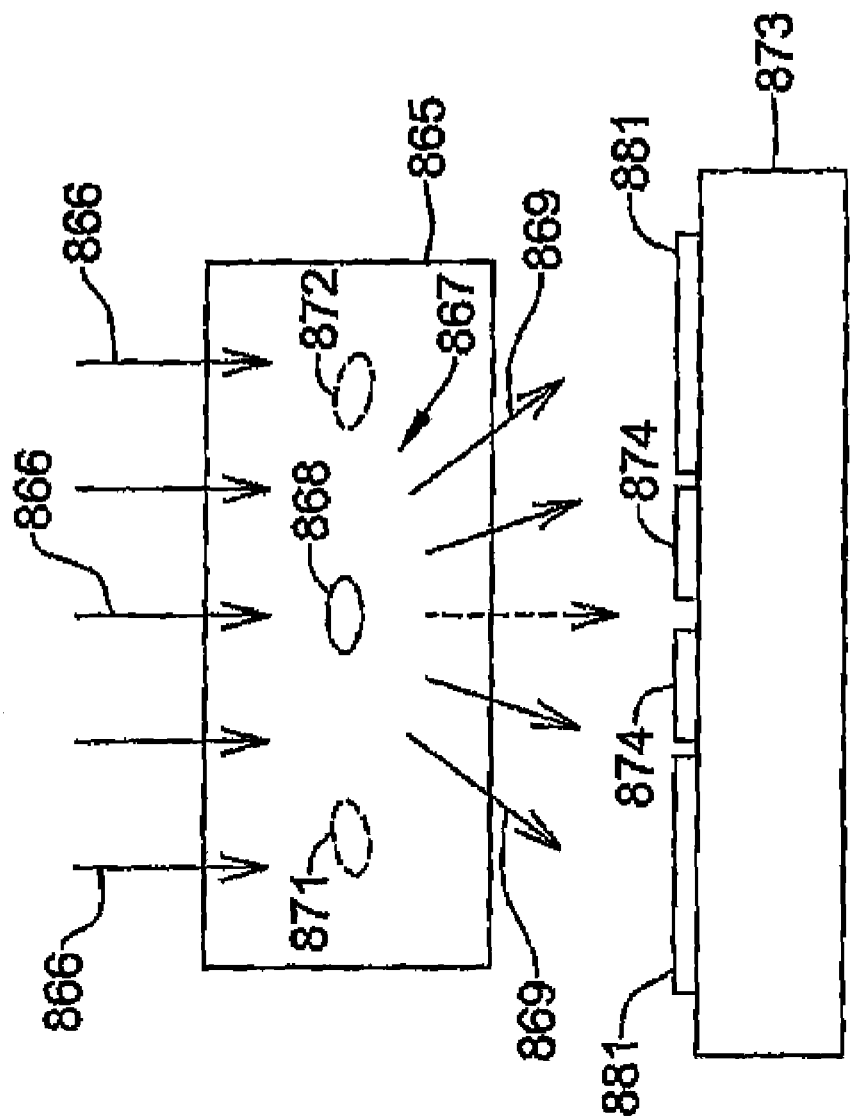
FIG. 28 is an end view of a flow channel with a light scatter detector.

A flow channel 865, shown in FIG. 28, may have a cross-section of about 100×200 microns. A core stream 867 of particles 868 may be about 15-20 microns wide. The spot of light 866 may about 20×180 microns for a 670 nm red light. As illustrated in FIG. 28, the core may move side-to-side as shown by particle positions 871 and 872. Scattered light 869 from the light 866 impinging the core stream 867 of single-file white blood cells 868 may be plotted with a photo detector 873 that measures a 1 to 3 degree band (FALS) with detection element 874 and a 3-11 degree band (SALS) with detection element 881 of scattered light 869. Detector 873 may also measure large angle scatter (LALS).

Figure 29A:
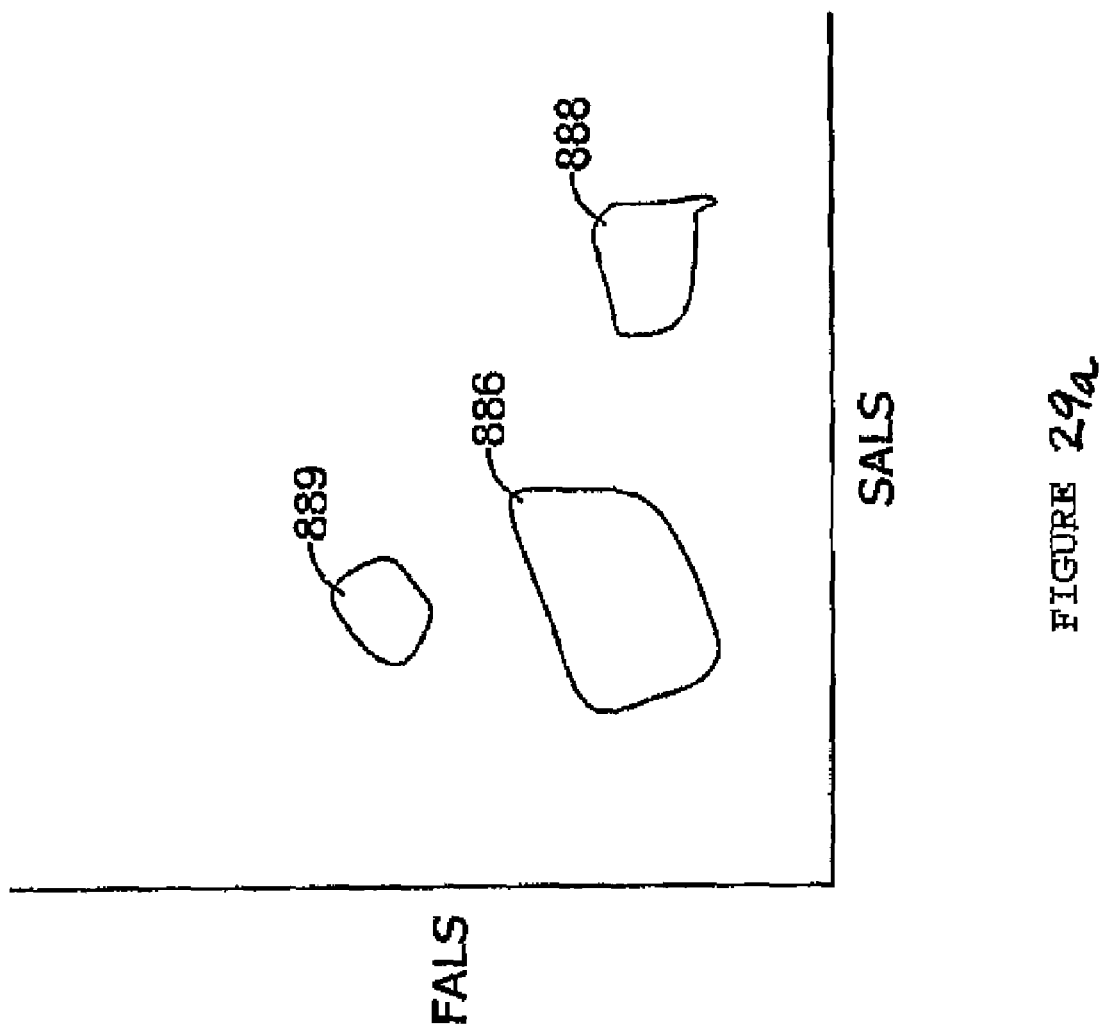
FIG. 29a is a plot of FALS versus SALS data revealing a three-part differentiation of white blood cells.

Pure scattering may enable identification of these types of white blood cells. A plot of the scatter is shown in FIG. 29a with FALS versus SALS and in FIG. 29b with FALS versus LALS data. FIGS. 6a and 6b herein show FALS versus SALS plots from some experimental runs. FIG. 2 herein shows a five-part differentiation of cells. The plots of FIGS. 29a and 29b may enable one to identify the five types of white blood cells; curve 886 represents lymphocytes; curve 887 represents neutrophils; curve 888 represents eosinphils; curve 889 represents basofils; and curve 880 represents monocytes. The detector 873 of FIG. 28 may be an annular detector. However, it may instead be a linear detector. The annular detector may provide better quality detection but the linear detector may be less costly.

Besides the types of white blood cells, there may be various species of each type. For example, the lymphocyte may be of CD4, CD8, CD19 or another species. Another approach besides scattering to identifying the species is needed. For instance, there may be a Y shaped antibody for CD4 and there may be a blue fluorescent tag or marker on the antibody; There may be another antibody for CD5 which may be marked with a fluorescent tag of another color. The count of tags for various colors may be made by exciting the marker or tag with a light beam of another wavelength. A photo multiplier tube may be used to detect the fluorescent light. The number of CD4s, CD5s, CDXXs, and the like may be counted. The latter event is not done with scattering. However, scattering may still be needed and used to eliminate false counts due to the extra unattached antibodies.

One may take whole blood and lyse it (i.e., remove the red blood cells) to end up with white blood cells plus antibodies. A white blood cell may have an antibody complex. If there were 100 lymphocytes, one should need 100 antibodies for species identification and count purposes. There may be antibodies for other species besides CD4s and CD5s. There may be some extra tagged antibodies so as not to miss any species. There may be a surplus of antibodies but only those attached to a cell are counted since light scatter may be used to count the cells. Light scatter may be used to ferret out the unattached antibodies that are tagged.

A cell may have a dimension of about 12 microns whereas an antibody may have a dimension in the range of hundreds of nanometers. There may be other approaches to tagging such as the use of magnetic tags. The crux is that for each species, e.g., CD4, CD5, . . . , of a type of the white blood cell, one may need a separate and different color for each species. For instance, 20 different colors would be needed to identify 20 various species in a single channel.

The various colors of the excited fluorescent tags may emanate out as one beam. These colors may be separated out in a big or brute force manner with a series of splitters tuned respectively to the different colors. A more compact approach a separation and detection of the various colors in the single light beam may be separated with a prism or a diffractive grating. The wavelengths, for example, may be 400, 430, 450, . . . , 670 nm, and so on.

Biological species may be an appropriate reference for such things as white blood cells. The sample observed may be from an environment and could have anthrax. The CD4 may be replaced by anthrax. In other words, an antibody may be used and replace the antibody used for CD4. One would need an antibody for each of the various things such as multiple agents within one system.

Monoclonal antibodies may be used instead of polyclonal antibodies. In FIG. 24a, there is a diagram of a lymphocyte with an antibody for CD4 and another one for CD8 in FIG. 24b. There may be antibodies for CD4 but they may go to CD8 which could result in false counts. That may be a problem which could occur with polyclonal antibodies. This problem may be solved with monoclonal antibodies since each would be characteristic so as to attach only to a CD4, CD8, or other designated species. Even though monoclonal antibodies are better quality and provide more accuracy than polynomial antibodies, the latter are significantly less expensive. Monoclonal antibodies may typically be used for CD4, CD8, and like domains.

As noted, there may be sub-classes of cells. Species may be warfare agents. Agents may include malaria, TB, and the like. Malaria may be in the blood, so there may be an antibody for malaria. Biological species may be in blood, warfare agents in water, and diseases in the blood; These kinds of biological species may be identified with antibodies having tags.

An antigen may look like an antenna (FIG. 24a) attached to, for instance, a CD4. The identification and counting of biological species in a handheld cytometer may provide preventive care in remote areas of the world. The handheld cytometer may be fully automated for sample preparation and analysis. Most, if not all cytometers, will not function with a sample from just a finger prick. The latter may be achievable for an untrained user of the cytometer. A sample may be needed only once a month. Laser pricking may be used with the present cytometer, but such approach is more expensive than an ordinary finger prick. Various other cytometer systems may require an actual draw of a substantial amount of blood.

Figure 30:
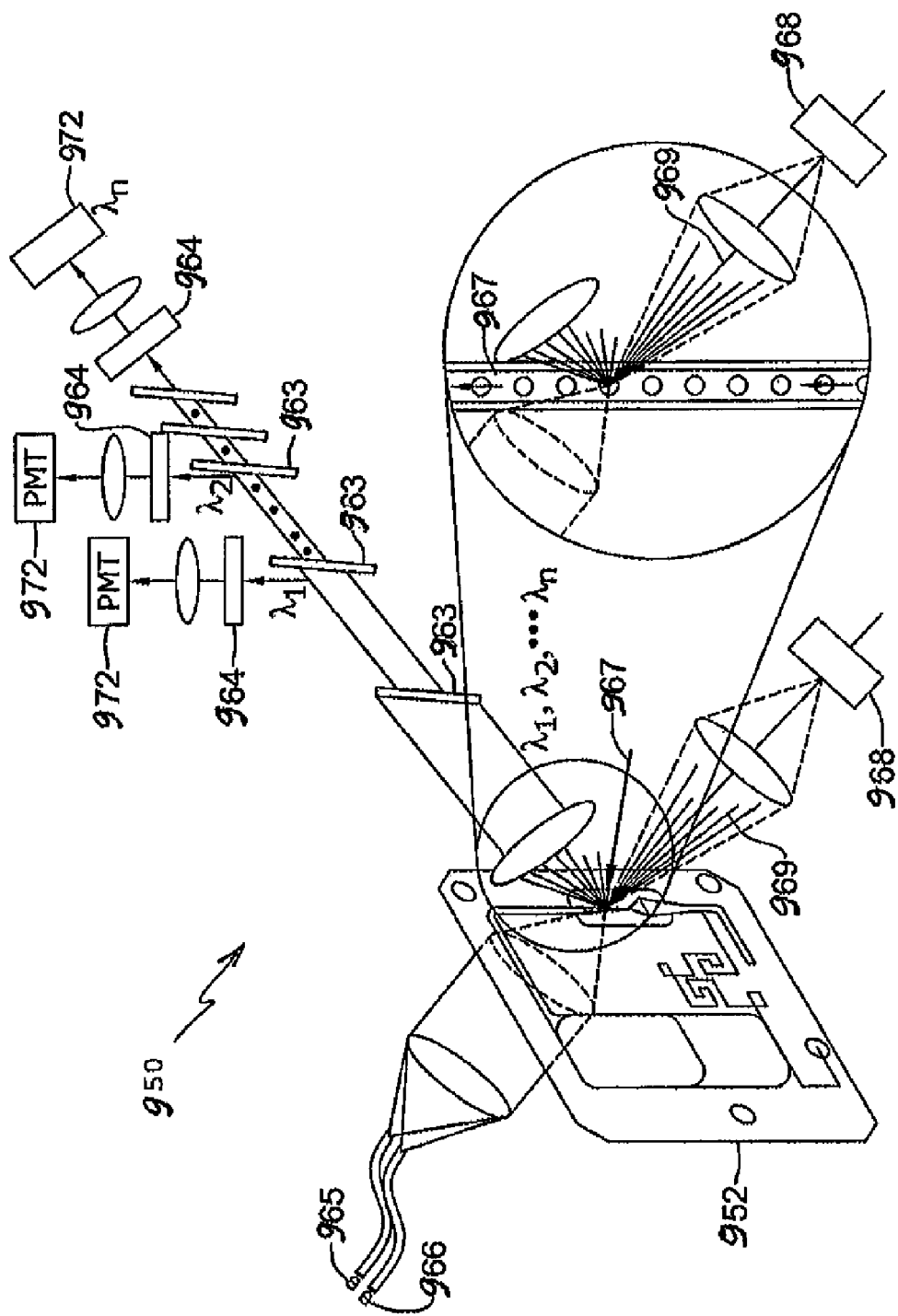
FIG. 30 is a schematic of a dichroic beam splitter type of optical system associated with a miniaturized cytometer cartridge.

FIG. 30 shows an optical layout of a system 950 for the parallel approach. This approach may be defined as one where parallel channels of dichroic beam splitters 963, band-pass filter 964 paths and detectors 972 are used in the fluorescence detection leg. The detectors 972 may be PMTs or other suitable types of detectors. The source leg may include two source (965, 966) wavelengths (blue 488 nm and red 630 nm) to illuminate the flow channel 967. However, there may instead be just one light source. A forward angle light scatter (FALS) detection leg is shown with a two element photodiode detector 968 with bandpass filters allowing for the measurement of the scattered light 969 at both the source wavelengths. The scatter signal from the FALS detector when plotted against the fluorescence signals, lets the system identify tagged antibodies which do not have an antigen associated with them, resulting in improved sensitivity of detection. This parallel approach results in a simple detection readout. Properties of this approach may include expansion to more than four colors which can lead to a large system size due to the parallel nature of this approach, and numerous beam splatters 963/bandpass filters 964, as the system is expanded.

Figure 31:
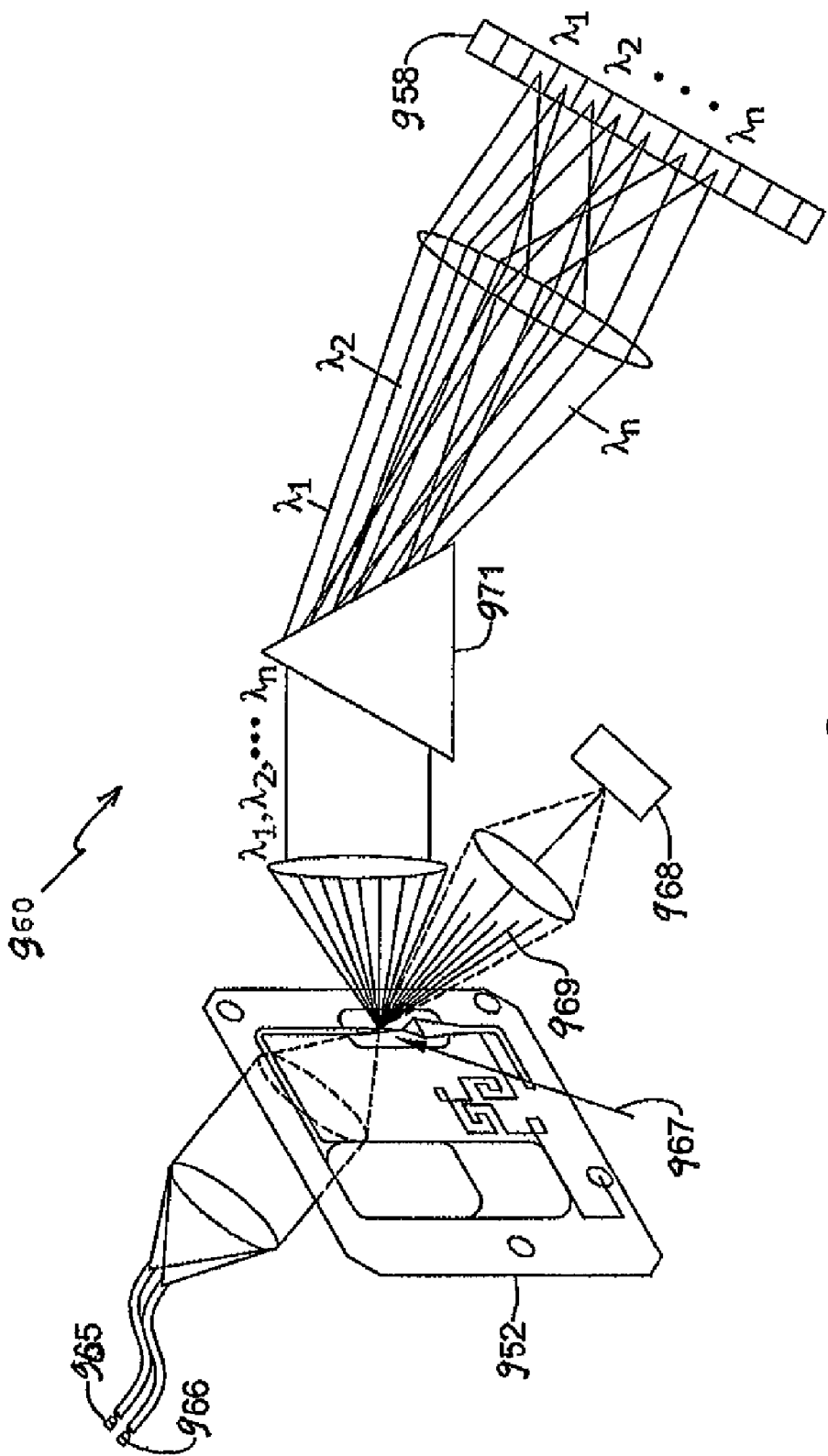
FIG. 31 is a schematic of a prism beam discriminator type of optical system associated with a miniaturized cytometer cartridge.

Reduction in the complexity of the system while allowing an increase in the number of detected fluorescence channels may be accomplished by recording all the fluorescence spectrums using a microspectrometer comprising of a linear detector array 958. FIG. 31 shows the optical layout of system 960 for the spectrometer based approach for the measurement of the fluorescent signals. System 960 may have two light sources 965, 966, or just one light source. For clarity, the pumping system, electronics and software interface are not shown in this Figure. This approach may have a prism 971 (or diffraction grating) that is used as the dispersive element to separate out the light according to wavelength or the various colors emitted by the different fluorescent dyes. The separated colors may then be focused towards individual detection elements of a photomultiplier (PMT) array 958. In summary, the fluorescence detection leg in this approach may be regarded as a microspectrometer. The FALS detection leg may be similar to the FALS detector 968 of the parallel approach shown in FIG. 30. The use of a microspectrometer in the detection leg may eliminate the need for multiple parallel fluorescence channels like in the approach shown in FIG. 30. Microspectrometers may have CCD detector arrays. The detector arrays need sufficient sensitivity to adequately sense the fluorescence signals produced by tagged antibodies, especially the discrete signals from cells flowing at the rate of 100-1000 cells per second. The microcytometer 950 may be expanded to more than four colors in a small system footprint. The maximum number of colors may be 32 due to the currently available 1×32 PMT array. However, larger PMT arrays may be available so as to increase the number of colors in the microcytometer 950. In the system 960 of FIG. 31, a prism 971, a grating, or the like may be used as the light dispersive element.

In FIG. 31, the PMT detector array 958 may have a certain fill factor pertinent to the overall system 960 signal-to-noise ratio. However, the power of the light source may be changed appropriately and custom optics may be tailored to the pitch of various PMT arrays. For testing, one may check on the availability of monoclonal antibodies for the chosen BW agents and simulants. The appropriate inactivated agents/simulants may be chosen for testing for those which monoclonal antibodies are available.

The table of FIG. 32 reveals significant parameters that may be incorporated in the AIDS/malaria version of the cytometer 950 or 960. This Figure shows an optical-based cytometer 950, 960 useful for AIDS/malaria applications. A three-channel (one scattering and two fluorescence) approach may be used. The system may be easily expanded to six or more channels without significant change in the overall size. For example, a total of one scattering channel and four fluorescence channels in detection space may likely be for the instrument (assuming that AIDS and malaria require different fluorescence channels). However, one may recognize that the capability to differentiate white cell count (to at least three parts) may be an important extension of the instrument for diagnosing and monitoring specific infections (viral and bacterial). Technically, such extended capability may require three scattering channels (described as optional scattering channels in FIG. 32) and possibly two cytometer measurement channels on-card. However, one measurement channel may suffice. Thus, as an option, one may consider adding this to the in-laboratory evaluation of the AIDS/malaria POC cytometer. On the illumination side, at least one red source may be needed for the AIDS assay, with the appropriate fluorophores, and both red and blue light sources may be needed for the malaria assay. The same red source may serve for both scattering and fluorescence measurements. In terms of cartridge complexity, both AIDS and malaria assays may require the same number of flow sensors and reagent reservoirs. For the AIDS assay, the same cytometer measurement channel and the same laser source may serve for both scatter and fluorescence measurements.

A baseline approach for the optical subsystem may assume that achieving required performance for both AIDS and malaria will entail measurements for both cell scattering (e.g., WBC count and type differentiation) and multicolor fluorescence (e.g., CD4/CD45/CDXX identification, counting and malaria species pathogen determination); The optical subsystem may incorporate red-excitation fluorophores and the integration of multiple optical scattering and fluorescence channels with one light source.

Figure 33:
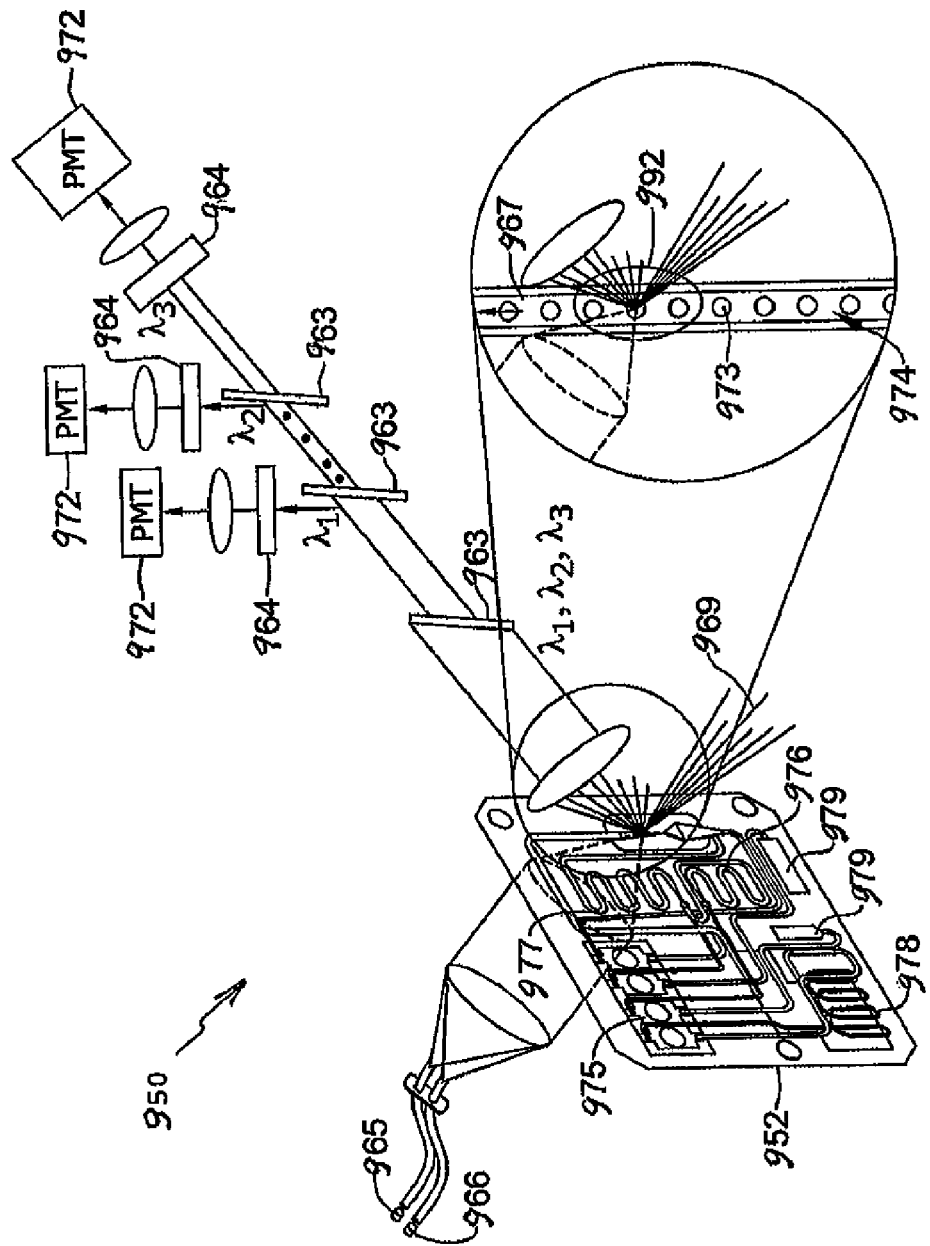
FIG. 33 is a schematic of a more detailed miniaturized cytometer cartridge with the associated optical system of FIG. 25.

FIG. 33 (similar to FIG. 30) shows system 950 with an the optical layout which may be regarded as a baseline approach, and has parallel channels of dichroic beam splitters 963, bandpass filters 964 and detectors 972, in the fluorescence detection leg. The source leg may have two lasers in red (966) and blue (965) wavelengths (e.g., 630 nm and 488 nm) to illuminate the flow channel 967 embedded in the disposable sample cartridge 952. However, there may instead be just one laser. As indicated in the Figure, one or more light sources 966, 965 may incorporate auto-alignment features in the form of a uniaxial micro translation stage that allows for the automatic alignment of the light source with a stream of cells 973 in the core flow 974 of the cytometer channel 967. When VCSEL arrays are used as the light source, automated electronic self-alignment of the light source with the cells 973 of core flow 974 may be accomplished (by selecting the appropriate VCSEL in alignment with the stream of cells). This electronic self-alignment capability may make the POC cytometer maintenance-free and robust for use in the field in developing countries.

FIG. 33 further shows an approach for an optical-based POC cytometer useful for AIDS/malaria applications. A three-channel (one scattering and two fluorescence) approach is shown here. The approach may be expanded to six or more channels without significant change in the overall size. For illustrative simplicity, the scatter detection legs are not shown in this Figure (but are shown in FIG. 30). Scattered light may be needed in at least one range of small angles, conventionally called the FALS channel (~1-3 degrees), to measure total WBC count, but additional angular bins at higher angles, such as SALS (~5-10 degrees) and LALS (large angle scattering), may be needed to differentiate the various types of the five different white cells (as shown in FIGS. 29*a* and 29*b*). Silicon photodiode detectors 968 of system 950 (FIG. 30) may be adequate for scattered light at the smaller angles, but a miniature photomultiplier tube (PMT) may be more effective for 90-deg scatter and for all fluorescent channels. Moreover, when the scattered signal from the FALS (~1-3 degrees)

detector is plotted against the fluorescent signals, the system may identify tagged antibodies that do not have an antigen on them, resulting in improved sensitivity of detection. This approach results in a simple detection readout based on proven approaches used in most large benchtop commercial cytometers. Four fluorescent detection channels may suffice for both the AIDS and malaria assays;

For the HIV assay, one may label white blood cells with CD4/CD45 antibody-antigen capture on a lab disposable cartridge or card 952. For flow cytometry tests, the card 952 may process a sample ~10 μL of whole blood, stain the white blood cells with CD4 and CD45 (and/or CDX, CDXX), lyse the red blood cells, and focus the remaining cells into an on-card cytometer channel for presentation and cytometric analysis by the POC cytometer 950. It may be a credit card sized disposable cartridge 952 used for the AIDS (CD4) assay. Card 952 may have flow sensors 975, lyse on-the-fly loop 976, stain on-the fly loop 977, channel 967, blood storage 978 and reagent storage 979, as indicated in FIG. 33.

There may be a process for testing within the disposable cartridge 952. A whole blood sample may be acquired by a finger prick. The blood may be stored in an on-card sample loop. Antibodies and a rehydrating buffer may be provided. Also, there may be a labeling of blood cells (i.e., antibody antigen binding) occurs. Then the red blood cells encounter a lysing with an on-card lysing reagent. The lysed blood may go where the cells 973 are focused in single file as a core stream 974 in channel 967 with an on-card sheath reagent. After the information about the cells 973 is attained, the blood may go to an on-card waste chamber.

Similarly, the two-color malaria assay may also integrate sample, antibody-antigen capture, reagent mixing, and other assay protocols on the cartridge. This approach may include the malaria assay. The microfluidics-based assay may reduce the consumption of expensive reagents, simplify the assay steps, and reduce total assay cost compared with the conventional assays that are used on benchtop cytometers today, as shown by a comparison of features in the table in FIG. 36.

The flow cytometer 950 or 960 may be used in remote areas for AIDS monitoring/malaria diagnosis. A rapid, deployable, low-cost (instrument and assay cost) instrument like the cytometer 950 or 960, which may provide results comparable to or better than the large commercial flow cytometry systems. In addition, for malaria, this may fulfill the need for a low-cost, easy-to-use POC flow cytometric screening that can identify the infecting species. The portable cytometer 950 or 960 may provide advantages for such screening in remote areas of the developing world. The advantages may include rapid and simple identification of patients who may need specific treatment, the reduction of the progression to severe malaria with its associated mortality and morbidity, the prevention of parasite resistance, and better patient outcomes for many people.

A comparison of commercially available and somewhat miniaturized cytometers with the present cytometer for CD4 and the like monitoring may show the latter to be most advantageous. The cytometer platform 950 or 960 may be regarded as the first practical cytometer-based platform for malaria diagnosis in a point-of-care setting in the developing world. The cytometer 950 or 960 may advance the state of the art in POC diagnosis and monitoring of infectious diseases with lower cost, high portability, simplicity of use by untrained personnel, and low maintenance requirements.

The cytometer 950 or 960 may have full capability for AIDS and malaria assays. At the outset, however, the mechanical housing and fixturing of all instruments built during the program may have space and slots allocated for a full AIDS/malaria measurement capability, even if some slots are not populated.

Fluorescent beads, whole blood, and malaria simulants may be used as target specimens. In addition to the mechanical housing, the POC instrument 950 or 960 may have several subsystems. Some of the subsystems may include a fluid driver (pumping) subsystem, optical subsystem, drive and sense electronics, and software and graphical user interface. For the CD4 assay, one may plan to use established gating algorithms such as Pan-leucogating, which appears to have good agreement with more complex gating methods.

Drive-sense electronics, algorithms, and software may be configured for testing clinical or environmental samples such as simulants and BW agents of a given input sample. The analysis cartridge may allow for the sample preparation (customizing commercially available reagent chemistry) and detection of BW agents in biological samples. The card or cartridge may have a sample inlet and regents-on-card reservoirs. There may also be on the card or cartridge, a waste storage reservoir, a place where the antibodies are mixed with antigens, and a place where the cytometric analysis of biological agents at least in part occurs.

Figure 34:
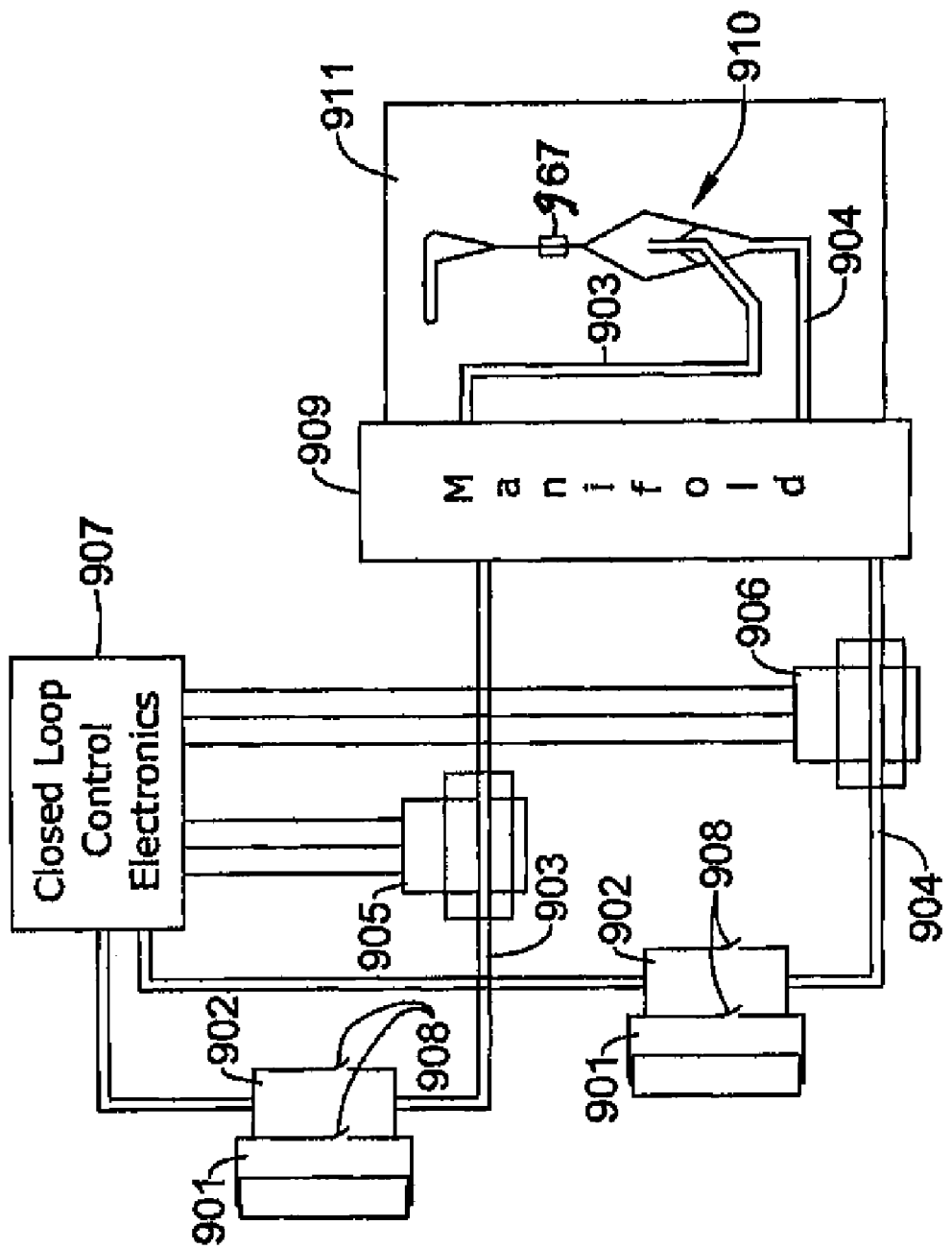
FIG. 34 shows a closed loop pumping system for a point of care instrument such as a hematology analyzer and flow cytometer.

Pumping may be a factor to note relative to POC analyzer instruments. The pumping system in some hematology analyzers and flow cytometers may be based on volume-controlled flow generated by syringe pumps that are driven by stepper motors. Such systems may be precise but bulky/power hungry and not suitable for use in POC instruments. As part of the POC hematology analyzer development, a miniaturized pressure-driven (as opposed to volume-driven) pumping system that operates in a closed loop may be used as shown in FIG. 34. The pump system may have high and low pressure chambers 901 and 902, along with microvalves 908 for providing the sample 903 and sheath fluid 904, respectively. The amounts of flow of sample 903 and sheath fluid 904 may be determined by flow sensors 905 and 906, respectively. The flow indications may go to a control loop control electronics 907. Electronics 907 may send signals, based on indications from flow sensors 905 and 906, to the pump system to control the flow of fluids 903 and 904 at certain desired levels. Sample fluid 903 and sheath fluid 904 may be pumped into a manifold 909. From manifold 909, sample 903 and sheath 904 may enter cytometer 910 and its channel 967 on a fluidic chip 911.

Figure 35A:
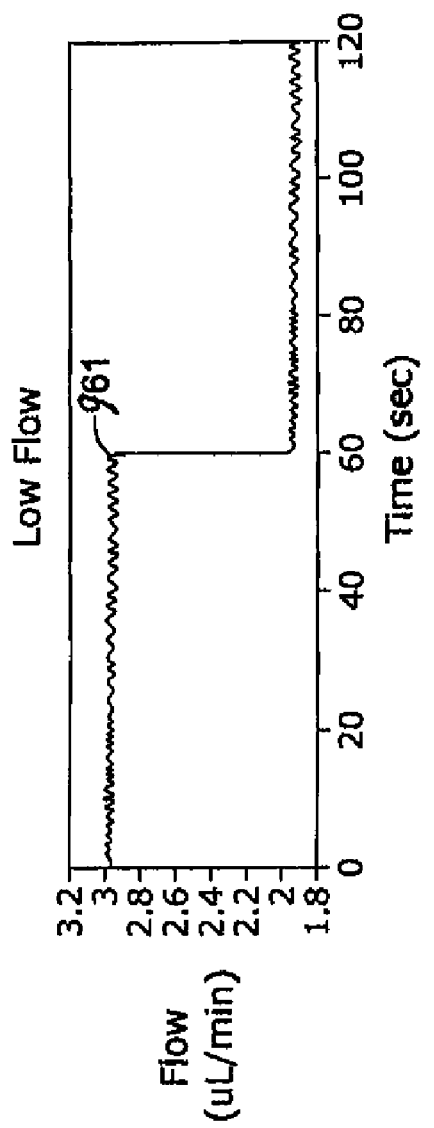
FIGS. 35a and 35b are graphs showing flow rate precision of the closed loop pumping system.
Figure 35B:
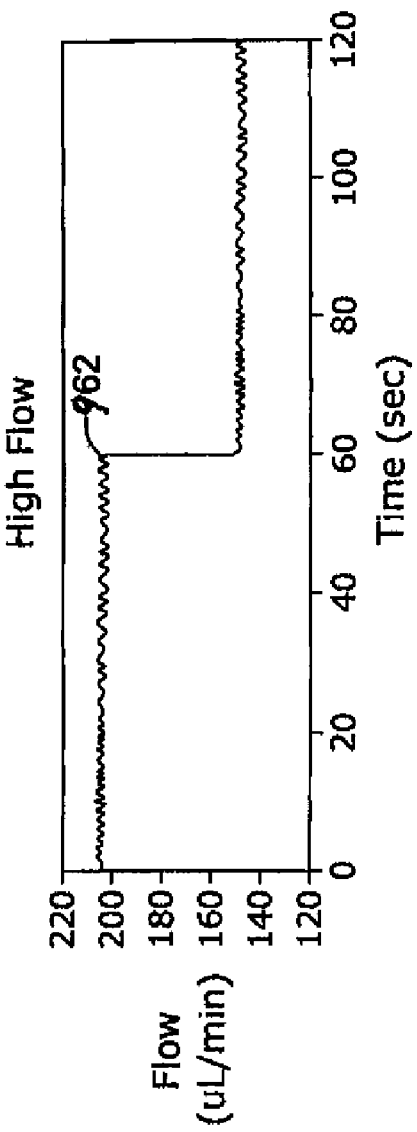

A miniaturized pressure-driven (as opposed to volume-driven) pumping system that operates in a closed loop may be used in the present cytometer. The operating principle of such a pump may involve a high-pressure source of air generated using a micropump; Lower and precisely controlled pressures may be generated from this high-pressure source by using arrays of miniaturized valves. The valves may be used in a closed-loop configuration with micro flow sensors mounted in each flow path to ensure the desired flow rate for each flow channel. Several generations of such pumps have been built, characterized, and shown to work well. The graphs in FIGS. 35a and 35b show the precise low and high flow rates that may be achieved with this technology. These graphs reveal data showing highly precise (one percent accuracy) control of the flow rates of two channels of this pumping system in the flow ranges of 2-3 μL/min shown by plot 961 of FIG. 35a and 150-200 μL/min shown by plot 962 of FIG. 35b. The high accuracy in the control of the flow rate of the various reagents and blood sample implies a high accuracy for the measured counts of blood cells. The present POC cytometer may use this closed-loop pumping technology with minor modifications of additional flow channels as necessary for the AIDS and malaria assays.

For various assays, a microfluidics-based assay on a cartridge 952 (cartridge) may have many advantages over a benchtop cytometer (benchtop) as shown in FIG. 36. The cartridge requires only about 12 μL of a whole blood sample whereas the benchtop requires about 100 μL. Four dilution steps are used with the benchtop and none is used with the cartridge. In view of the difficulty of reasonably obtaining monoclonal antibodies, only 0.6 μL (not optimized) is needed for the cartridge whereas 5 μL are needed for the benchtop. For the cartridge, the number and duration of incubation steps are two with one for 20 seconds at room temperature and the other also for 20 seconds at room temperature. For the benchtop, the incubation steps include one for 30 minutes at 40 degrees C. and another for 5 minutes at room temperature, The amounts of lysing solution used are 500 μL and 1.4 mL in the cartridge and the benchtop, respectively. The cytometric measure time is about 2-3 minutes for both the cartridge and the benchtop.

In the cytometer, there may be an on-cartridge reagent storage 979 and embedded micro flow sensors 975 (FIGS. 30, 31, 33). The card 952 may use a stored liquid solution of CD4 and CD45 antibodies (stored at 0°-4° C.). There may be a process for printing dried CD4 and CD45 antibodies directly into a microfluidic channel within the card. One may deposit nanoliter volumes of biological reagents onto plastic surfaces. Once the reagents are dried into a microchannel, the channels may be sealed using a cold lamination process. The reagents may then be rehydrated with a buffer (also stored on the card) so that they retain their biological activity to label the correct cells, and mixed with blood on the card during use. A control card may be run with nondried reagents in a similar card as a reference. There may be protocols for drying the reagents in microchannels and for rehydrating the dried reagents so that they retain their biological activity to label the correct cells.

There may be a systematic approach to producing integrated plastic disposable cards 952 for point-of-care diagnostics applications. Multiple mircrofluidic functions for a given application may be reduced to the simplest form (called subcircuits). For example, proper alignment and capture of a drop of reagent into a card may be an initial subcircuit in the card. The card may permit a user to apply a drop of blood (obtained from a finger prick) and then draw (via aspiration) a small amount (~10-30 μL) of the sample into the card using finger pressure. There may be micro-check valves that permit air and liquid to pass unidirectionally in a microfluidic channel. These valves, when used in conjunction with a flexible air bladder that may be incorporated into the card, may permit the end user to easily acquire a measured volume of reagent; The subcircuits may be integrated into an operational card.

Ultra low autofluorescence materials may be used for disposable analysis cartridges 952. A cyclic olefin copolymer (COC) based plastic may have autofluorescence properties as good as or better than glass at 488 nm and also be a very good moisture barrier. The glass transition temperature of this material may be about 70 to 180 degrees C., depending on the grade. The COC polymer may have a very high light transmission (>95 percent) at 488 nm.

Identified may be low cost plastics that have glass-like autofluorescence properties at 488 nm and could be used to form optical windows and/or lens (e.g., lens 992 of FIG. 33) on disposable analysis cards 952. A specific family of plastics may include COC (Topas™) and other such polymers. Additionally, these optical windows may also be made of quartz, Pyrex™ and other glass or glass-like materials. Since various COCs may have very low levels of autofluorescence, they may be very well suited for use in disposable microfluidic cards for fluorescence flow cytometry. COC plastics may be easily incorporated into the card manufacturing process unlike other glass materials. The birefringence of these plastics may be lower than polycarbonate, polystyrene and acrylic. The COC plastics appear to have very good chemical resistance properties, are lightweight, resist shattering, and are biocompatible. They may have a transmission of about 92 percent at visible wavelengths, a refractive index of about 1.533, and an Abbe number of 56. Those plastics may also have good dimensional stability and a high glass transition temperature.

Figure 37:
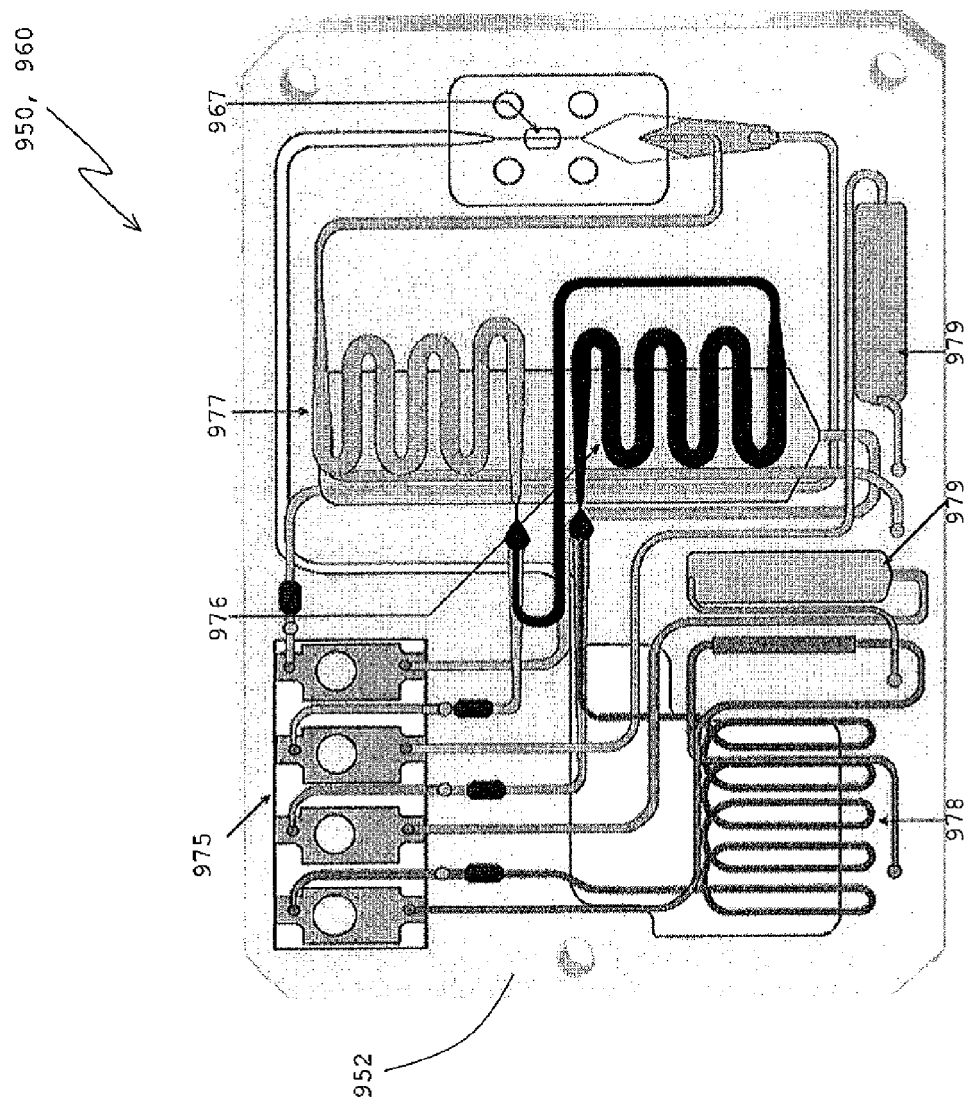
FIG. 37 is a diagram of a miniaturized cartridge layout for providing an AIDS (CD4) assay.
Figure 38:
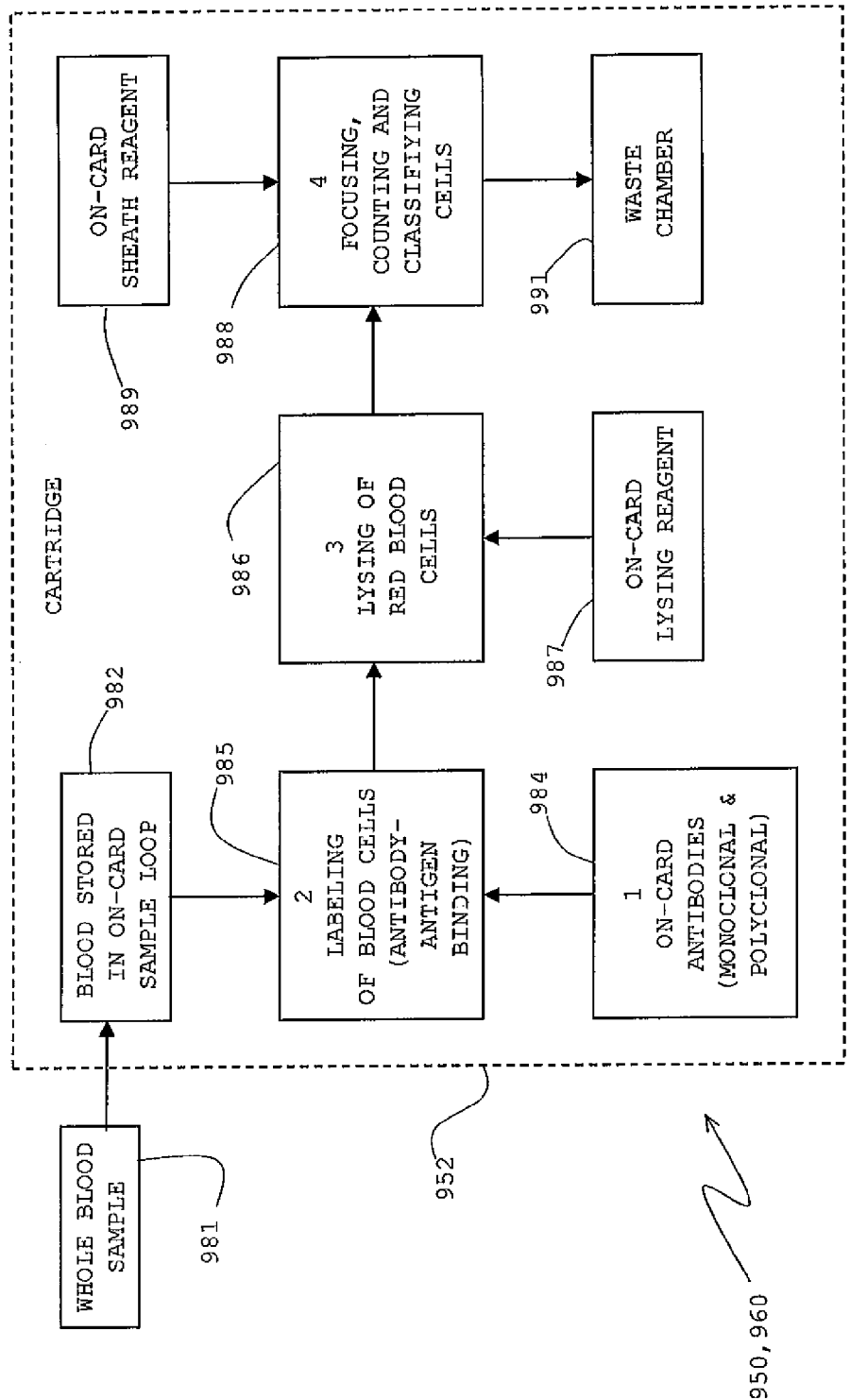
FIG. 38 is a diagram showing an operating sequence of a miniaturized cartridge having application for immunoassays and hematology tests.

For flow cytometry tests, the card 952 may process a sample ~10 μL of whole blood, stain the white blood cells with CD4 and CD45 antibody antigen capture, lyse the red blood cells, and focus the remaining cells into an on-card cytometer channel for presentation and cytometric analysis by the POC cytometer 950. The credit card sized disposable cartridge 952 for the AIDS (CD4) assay and its operating sequence are shown in FIGS. 37 and 38, respectively. Card 952 may have flow sensors 975, lyse on-the-fly loop 976, stain on-the fly loop 977, channel 967, blood storage 978 and reagent storage 979.

FIG. 38 shows a process diagram for the operating sequence within the disposable and/or microfluidic cartridge 952 of system 950, 960. A whole blood sample may be acquired by a finger prick at block 981. The blood may be stored in an on-card sample loop at block 982. Section 984 may provide on-card antibodies (monoclonal and polyclonal) to section 985. Also, blood from block 982 may go to section 985 where a labeling of blood cells (i.e., antibody-antigen binding) occurs. From section 985, the blood may go to section 986 where the red blood cells encounter a lysing with an on-card lysing reagent from block 987. The lysed blood may go on to section 988 where the cells 973 are focused in single file as a core stream 974 in channel 967 (FIG. 33) with an on-card sheath reagent from block 989. The cells may be counted and classified. After various items of information about the cells 973 are attained, the blood may go to an on-card waste chamber in block 991.

Material selection may be significant in the card 952 fabrication process to ensure a good functioning card. Given the breadth of possible applications, chemistries, and other components that may be integrated for optimal performance, no universal plastic appears to exist that meets the needs of every card design. Rather, there are a variety of plastics and adhesives that may be balanced with the specifications of the desired card's functionality. Various candidate plastic films may be assessed for material opaqueness suitable at 488 nm (blue) and 630 nm (red). In addition, one may note plastics with very good moisture barrier properties, such as Honeywell's Aclar™ film. The barrier properties of the films may play a critical role in preventing liquids from drying out ($H_2O$ migration), as well as preventing pH drift (minimizing migration of $O_2$ and $CO_2$). Material selection may be of particular importance given the objective that the commercial disposable card should be stable at ambient temperature for up to a year and be suitable for use in remote regions of the developing world.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A point of care analyzer comprising:
a portable cartridge holding instrument; and
a microfluidic cartridge insertable in the portable cartridge holding instrument, wherein the cartridge is credit-card sized; and
wherein:
the microfluidic cartridge comprises:
a cytometry flow channel having transparent windows;
an intersecting region having an output connected to the cytometry flow channel;
a sample channel connected to a first input of the intersecting region;
a sheath fluid channel connected to a second input of the intersecting region;
a sheath fluid reservoir connected to the sheath fluid channel; and
a waste reservoir connected to the cytometry flow channel;
the intersecting region is for hydrofocusing a sample having particles from the sample channel with a sheath fluid into a single file core of particles;
the cytometry flow channel is for conveying the single file of particles with the sheath fluid through the transparent windows of the cytometry flow channel and to the waste reservoir;
when the microfluidic cartridge is inserted in the portable cartridge holding instrument, the transparent windows are aligned with one or more light sources and one or more detectors in the portable cartridge holding instrument to form both a scattering optical channel and a fluorescence optical channel; and
the microfluidic cartridge is disposable upon at least a partial filling of the waste reservoir with particles from the cytometry flow channel.

2. The analyzer of claim 1, wherein the particles in the waste reservoir are regarded as biological waste.

3. The analyzer of claim 2, wherein the cartridge having the waste reservoir containing the biological waste is disposable in accordance with applicable health regulations.

4. The analyzer of claim 1, further comprising:
a second intersecting region having an output connected to the sample channel;
a blood reservoir having an output connected to the second intersecting region; and
a lysing reagent reservoir having an output connected to the second intersecting region.

5. The analyzer of claim 4, further comprising an input port connected to the blood reservoir.

6. The analyzer of claim 5, wherein:
the sample having particles is blood; and
the lysing reagent is for lysing red blood cells in the blood.

7. The analyzer of claim 6, wherein the lysing red blood cells occurs in the second intersecting region and/or the sample channel.

8. The analyzer of claim 7, wherein the lysing red cells in the second intersecting region and/or the sample channel comprises lysing-on-the-fly.

9. The analyzer of claim 1, further comprising:
a second intersecting region having an output connected to the sample channel;
a blood reservoir having an output connected to the second intersecting region; and
a sphering reagent reservoir having an output connected to the second intersecting region.

10. The analyzer of claim 9, wherein:
the sample having particles is blood; and
the sphering reagent is for sphering red blood cells in the blood.

11. The analyzer of claim 10, wherein the sphering red blood cells occurs in the second intersecting region and/or the sample channel.

12. The analyzer of claim 11, wherein the sphering red cells in the second intersecting region and/or the sample channel comprises sphering-on-the-fly.

13. The analyzer of claim 1, wherein a first optical circuit comprises the transparent windows of the cytometry flow channel, and at least one of the one or more light sources and at least one of the one or more detectors of the cartridge holding instrument aligned with the transparent windows.

14. The analyzer of claim 13, wherein a second optical circuit comprises the transparent windows of the cytometry flow channel, and at least one of the one or more light sources and at least one of the one or more detectors of the cartridge holding instrument aligned with the transparent windows.

15. The analyzer of claim 14, wherein the sample having particles is blood:
the first optical circuit comprises at least one scattering optical channel for determining a count and/or properties of particles of the blood sample; and
the second optical circuit comprises at least one fluorescent optical channel for detecting and identifying markers on particles of the blood sample for an immunoassay.

16. The analyzer of claim 15, wherein the scattering optical channel is for detecting light scattered by particles of the sample at various angles.

17. The analyzer of claim 16, wherein light scattered by the particles is for the determining a count and/or properties of particles of the blood sample.

18. The analyzer of claim 15, wherein the immunoassay is for detecting particles of the blood sample that are at least one of a group of CD4, CD45, CDX, CDXX, *p. falciparum, p. vivax*, and various other pathogens.

19. The analyzer of claim 18, wherein the pathogens can effect AIDS, malaria, HIV, or TB.

20. The analyzer of claim 18, wherein the immunoassay comprises:
incubating and tagging particles with fluorescent antibodies;
impinging the particles with light;
detecting fluorescence emitted from the tagged particles;
detecting light scattered by the particles; and
determining CDXX and/or pathogen data from fluorescence emitted from the tagged particles and/or light scattered by the particles.

21. The system of claim 1, wherein the cartridge is a microfluidic cartridge comprising plastic type and/or glass type materials having autofluoresence properties as good or better than glass at 488 nm.

22. The system of claim 1, wherein the cartridge comprises a cyclic olefin copolymer based plastic material structure.

23. The system of claim 1, wherein the cartridge is a laminated structure with etched channels for microfluidic circuits.

24. The system of claim 1, wherein the cartridge has a molded structure containing channels for microfluidic circuits.

25. A point of care analyzer comprising:
a portable cartridge holding instrument; and
a microfluidic cartridge insertable in the portable cartridge holding instrument, wherein the cartridge is credit-card sized; and
wherein:
the microfluidic cartridge comprises:
- a first cytometry flow channel having transparent windows;
- a first intersecting region having an output connected to the first cytometry flow channel;
- a first sample channel connected to a first input of the first intersecting region;
- a first sheath fluid channel connected to a second input of the first intersecting region;
- a first sheath fluid reservoir connected to the first sheath fluid channel; and
- a first waste reservoir connected to the an output of the first cytometry flow channel;
- a second intersecting region having an output connected to the first sample channel;
- a first blood reservoir having an output connected to the second intersecting region;
- a lysing reagent reservoir having an output connected to the second intersecting region
- a second cytometry flow channel having transparent windows;
- a third intersecting region having an output connected to the second cytometry flow channel;
- a second sample channel connected to a first input of the third intersecting region;
- a second sheath fluid channel connected to a second input of the third intersecting region;
- a second sheath fluid reservoir connected to the second sheath fluid channel;
- a second waste reservoir connected to an output of the second cytometry flow channel;
- a fourth intersecting region having an output connected to the second sample channel;
- a second blood reservoir having an output connected to the fourth intersecting region; and
- a sphering reagent reservoir having an output connected to the fourth intersecting region, wherein when the microfluidic cartridge is inserted in the portable cartridge holding instrument, the transparent windows are aligned with one or more light sources and one or more detectors in the portable cartridge holding instrument to form both a scattering optical channel and a fluorescence optical channel.

26. The analyzer of claim 25, wherein:
the first intersecting region is for hydrofocusing a sample having particles from the first sample channel with a sheath fluid into a first single file core of particles;
the first cytometry flow channel is for conveying the first single file of particles with the sheath fluid by the transparent windows of the first cytometry flow channel and then to the first waste reservoir;
the third intersecting region is for hydrofocusing a sample having particles from the second sample channel with a sheath fluid into a second single file core of particles; and
the second cytometry flow channel is for conveying the second single file of particles with the sheath fluid by the transparent windows of the second cytometry flow channel and then to the second waste reservoir.

27. The analyzer of claim 26, wherein:
when the microfluidic cartridge is inserted in the portable cartridge holding instrument, the transparent windows of the cytometry flow channels are aligned with one or more light sources and one or more detectors in the portable cartridge holding instrument; and
the microfluidic cartridge is disposable upon a partial filling of the first waste reservoir with particles from the first cytometry flow channel.

28. The analyzer of claim 27, wherein particles from a cytometry flow channel to the waste reservoir are to be regarded as biological waste.

29. The analyzer of claim 28, wherein the cartridge containing the waste in the waste reservoir is disposed in accordance with applicable health regulations.

30. The analyzer of claim 27, wherein a first optical circuit comprises the transparent windows of a cytometry flow channel, and at least one of the one or more light sources and at least one of the one or more detectors of the cartridge holding instrument aligned with the transparent windows.

31. The analyzer of claim 30, wherein a second optical circuit comprises the transparent windows of a cytometry flow channel, and at least one of the one or more light sources and at least one of the one or more detectors of the portable cartridge holding instrument aligned with the transparent windows.

32. The analyzer of claim 31, wherein the first and second sample channels transport a blood sample there through:
the first optical circuit comprises at least one scattering optical channel for determining a count and/or properties of particles of the blood sample;
the second optical circuit comprises at least one fluorescent optical channel for detecting and identifying markers on particles of the blood sample for an immunoassay;
the immunoassay is for detecting particles of the blood sample that are at least one of a group of CD4, CD45, CDX, CDXX, *p. falciparum*, *p. vivax*, and various other pathogens; and
light scattered by the particles is for the determining a count and/or properties of particles of the blood sample.

33. A point of care analyzer comprising:
a portable cartridge holding instrument; and
a microfluidic cartridge insertable in the portable cartridge holding instrument, wherein the cartridge is credit-card sized; and
wherein:
the microfluidic cartridge comprises:
- a cytometry flow channel having transparent windows;
- an intersecting region having an output connected to the cytometry flow channel;
- a sample channel connected to a first input of the intersecting region;
- a sheath fluid channel connected to a second input of the intersecting region;
- a sheath fluid reservoir connected to the sheath fluid channel; and
- a waste reservoir connected to the cytometry flow channel;
the intersecting region is for hydrofocusing a sample having particles from the sample channel with a sheath fluid into a single file core of particles;
the cytometry flow channel is for conveying the single file of particles with the sheath fluid through the transparent windows of the cytometry flow channel and to the waste reservoir;
when the microfluidic cartridge is inserted in the portable cartridge holding instrument, the transparent windows are aligned with one or more light sources and one or more detectors in the portable cartridge holding instrument to form both a scattering optical channel and a fluorescence optical channel; and the microfluidic cartridge is disposable after an entry of any particles and/or sheath fluid from the cytometry flow channel to the waste reservoir.

34. The system of claim 33, wherein the cartridge comprises a cyclic olefin copolymer based plastic material structure.

* * * * *